United States Patent
Raeber et al.

(10) Patent No.: US 7,939,637 B2
(45) Date of Patent: May 10, 2011

(54) INSULIN-LIKE GROWTH FACTOR ANTIBODIES AND USES THEREOF

(75) Inventors: Olivia Raeber, Redwood City, CA (US); Gadi Gazit-Bornstein, Cambridge, MA (US); Xiaodong Yang, Palo Alto, CA (US); Susan Ann Cartlidge, Macclesfield (GB); David William Tonge, Macclesfield (GB)

(73) Assignee: MedImmune Limited, Cambridge (GB)

( * ) Notice: Subject to any disclaimer, the term of this patent is extended or adjusted under 35 U.S.C. 154(b) by 0 days.

(21) Appl. No.: 11/608,705

(22) Filed: Dec. 8, 2006

(65) Prior Publication Data

US 2007/0196376 A1 Aug. 23, 2007

Related U.S. Application Data

(60) Provisional application No. 60/750,085, filed on Dec. 13, 2005, provisional application No. 60/750,772, filed on Dec. 14, 2005, provisional application No. 60/774,747, filed on Feb. 17, 2006, provisional application No. 60/808,183, filed on May 24, 2006.

(51) Int. Cl.
*A61K 39/395* (2006.01)
*C07H 21/04* (2006.01)
*C12P 21/06* (2006.01)
*C07K 16/26* (2006.01)

(52) U.S. Cl. ............ 530/387.1; 424/141.1; 424/145.1; 435/335; 530/388.1; 530/388.23

(58) Field of Classification Search ............... None
See application file for complete search history.

(56) References Cited

U.S. PATENT DOCUMENTS 6,632,927 B2 * 10/2003 Adair et al. ............ 530/387.3
2006/0193772 A1    8/2006 Ochiai et al.

FOREIGN PATENT DOCUMENTS

| EP | 492552 A1 | 7/1992 |
| EP | 1 505 075 * | 9/2005 |
| WO | WO 02/053596 * | 7/2002 |
| WO | WO 03/93317 | 11/2003 |
| WO | 2005/016970 A2 | 2/2005 |
| WO | WO 2005/018671 | 3/2005 |
| WO | WO 2005/028515 | 3/2005 |
| WO | 2007/022172 A2 | 2/2007 |

OTHER PUBLICATIONS

Holliger et al., Engineered antibody fragments and the rise of single domains, 2005, Nature Biotechnology, vol. 23, Issue 9, pp. 1126-1136.*
Amit et al., 1986, Science, vol. 233, No. 4765, pp. 747-753.*
Panka et al., 1988, Proc. Natl. Acad. Sci. USA, vol. 85, pp. 3080-3084.*
Rudikoff et al., 1982, Proc. Natl. Acad. Sci. USA, vol. 79, pp. 1979-1983.*
Benini et al. *Clin. Cancer Res.* 7:1790-1797 (2001).
Burtrum et al. *Cancer Res.* 63:8912-8921 (2003).
Cohen et al. *Clin. Cancer Res.* 11:2063-2073 (2005).
Garcia-Echeverria et al. *Cancer Cell.* 5:231-239 (2004).
Goetsch et al. *Int. J. Cancer.* 113:316-328 (2005).
Goya et al. *Cancer Res.* 64:6252-6258 (2004).
Hailey et al. *Mol. Cancer Ther.* 1:1349-1353 (2002).
Maloney et al. *Cancer Res.* 63:5073-5083 (2003).
Mitsiades et al. *Cancer Cell.* 5:221-230 (2004).
Miyamoto et al. *Clin. Cancer Res.* 11(9):3494-3502 (2005).
Sachdev et al. *Cancer Res.* 63:627-635 (2003).
Wu et al. *Cancer Res.* 63:4384-4388 (2003).
Yakar et al. *Proc. Natl. Acad. Sci. USA.* 96:7324-7329 (1999).
Enjoh T et al, Characterization of New Monoclonal Antibodies to Human Insulin-Like Growth Factor-II and Their Application in Western Immunoblot Analysis, Journal of Clinical Endocrinology and Metabolism, 1993, 510-517, 77.
Manes S et al, Functional Epitope Mapping of Insulin-Like Growth Factor I (IGF-I) by Anti-IGF-I Monoclonal Antibodies, Endocrinology, 1997, 905-915, 138.
Russel W E et al, Inhibition of the mitogenic effects of plasma by a monoclonal antibody to stomatomedin C, Proceedings of the national academy of science, 1984, 2389-2392, 81.
Van Wuk Judson J et al, Molecular Basis for Species and Ligand Specificity of a Monoclonal Antibody Raised Against Human IGIF-I, Endocrinology, 1997, 4521-4523, 138.
Cartlidge Susan A et al, MEDI-573-A fully human antibody to IGF-I and IGF-II for the treatment of solid tumor and hematological diseases, American Association for Cancer Research 100th Annual Meeting, Denver, Apr. 2009.
International Search Report, PCT/ISA/210, WIPO, Apr. 2005.
Masaharu Takigawa et. al, "Insulin-Like Growth Factors I and II Are Autocrine Factors in Stimulating Proteoglycan Synthesis, a Marker of Differentiated Chondrocytes,Acting through Their Respective Receptors on a Clonal Human Chondrosarcoma-Derived Chondrocyte Cell Line, HCS-2/8", Endocrinology, vol. 138,No. 10, pp. 4390-4400, 1997.
Raffaele Zarrilli et al., "Constitutive Insulin-like Growth Factor-II Expression Interferes with the Enterocyte-like Differentiation of CaCo-2 Cells", The Journal of Biological Chemistry,vol. 271, No. 14, pp. 8108-8114,1996.
Blakey David, Development of a Portfolio of Antibody Based Therapeutics for Cancer Therapy, ELRIG (2009) European Laboratory Robotics Interest Group—Drug Discovery 2009, Sep. 7-8, 2009, Liverpool, UK, (presentation).
Blakey David, Development of a Portfolio of Antibody Based Therapeutics for Oncology, Pre-Clinical/Clinical Development of Therapeutic Antibodies, PEGS (2009) Protein Engineering Summit—5th Annual, Apr. 6-7, 2009, Boston, (presentation).

(Continued)

*Primary Examiner* — Robert Landsman
*Assistant Examiner* — Ian Dang
(74) *Attorney, Agent, or Firm* — MedImmune

(57) ABSTRACT

Binding proteins, such as antibodies directed to IGF-II with cross-reactivity to IGF-I and uses of such antibodies are described. In particular, fully human monoclonal antibodies directed to the IGF-II with cross-reactivity to IGF-I are disclosed. Also discussed are nucleotide sequences encoding, and amino acid sequences comprising, heavy and light chain immunoglobulin molecules, particularly sequences corresponding to contiguous heavy and light chain sequences spanning the framework regions and/or complementarity determining regions (CDR's), specifically from FR1 through FR4 or CDR1 through CDR3.

18 Claims, 3 Drawing Sheets

OTHER PUBLICATIONS

Blakey David, Development of novel human therapeutic antibodies targeting the IGF and PDGF signalling pathways for cancer therapy, ICRA (2009) International Congress on Recombinant Antibodies—Jun. 8, 15-19, 2009, Cologne, (presentation).

Blakey David, Identification and preclinical anti-tumour activity of human antibodies targeting growth factor and angiogenic ligands, WBF (2009) World Biopharm Forum—Cancer Biologics and Therapy, (presentation).

Bosslet K. et al., The Development of Therapeutic antibodies for Cancer Therapy, VP Oncology Research MedImmune, Bio (2009) Bionnale, Apr. 29, 2009(presentation).

Cartlidge S. et al., A fully human antibody to IGF-I and IGF-II for the treatment of solid tumour and haematological diseases, AACR (2009) American Association for Cancer Research—100th Annual Meeting.

Cheesebrough et al., In vivo pharmacology of MEDI-573, an anti-IGF-I and IGF-II antibody that targets the IGF-1R and IR-A signaling pathways, AACR (2009) American Association for Cancer Research—100th Annual Meeting, Apr. 18-22, 2008, Denver, CO.

Zusmanovich M et al., A Pharmacokinetic/Pharmacodynamic Study of Medi-573, a Fully Human IgG2 Monoclonal Antibody against Insulin-like Growth Factors, in Male Cynomolgus Monkeys Following Intravenous Administration, AAPS (2009) American Association of Pharmaceutical Scientists—2009 Annual Meeting & Exposition, Nov. 8-12, 2009, Los Angeles, CA, (presentation).

* cited by examiner

SEQUENCE LISTING

<160> NUMBER OF SEQ ID NOS: 102

<210> SEQ ID NO 1
<211> LENGTH: 372
<212> TYPE: DNA
<213> ORGANISM: Human

<400> SEQUENCE: 1
cagctgcagc tgcaggagtc gggcccagga ctggtgaagc cttcggagac cctgtccctc      60
acctgcactg tctctggtgg ctccatcagg agtagtagtt actactgggg ctggatccgc     120
cagcccccag ggaaggggct ggagtggatt ggggggtatct attatagtgg gagcacctac    180
tacaacccgt ctctcaagag tcgagtcacc atgtccgtag acacgtccaa gaaccagttc     240
tccctgaagc tgagctccgt gaccgccgca gacacggctg tgtattactg tgcgagacaa     300
aggggtcata gcagtggctg gtggtacttc gatctctggg gccgtggcac cctggtcact     360
gtctcctcag cc                                                         372

<210> SEQ ID NO 2
<211> LENGTH: 124
<212> TYPE: PRT
<213> ORGANISM: Human

<400> SEQUENCE: 2

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Gly Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Arg Gly His Ser Ser Gly Trp Trp Tyr Phe Asp Leu
            100                 105                 110

Trp Gly Arg Gly Thr Leu Val Thr Val Ser Ser Ala
        115                 120

<210> SEQ ID NO 3
<211> LENGTH: 324
<212> TYPE: DNA
<213> ORGANISM: Human

<400> SEQUENCE: 3
gacatccaga tgacccagtc tccatcttcc gtgtctgcat ctgtaggaga cagtgtcacc      60
atcacttgtc gggcgagtca gggtattagc agctacttag cctggtatca gcagaaacca     120
gggaaagccc ctaaactcct gatctatgct gcatccagtt tgcaaagtgg ggtcccatca     180
aggttcagcg gcaatggatc tgggacagat ttcactctca ccatcagcag cctgcagcct     240
gaagattttg caacttacta ttgtcaacag gctaacaatt tcccattcac tttcggccct     300
gggaccaaag tggatatcaa acga                                            324

```
<210> SEQ ID NO 4
<211> LENGTH: 108
<212> TYPE: PRT
<213> ORGANISM: Human

<400> SEQUENCE: 4

Asp Ile Gln Met Thr Gln Ser Pro Ser Ser Val Ser Ala Ser Val Gly
 1               5                  10                  15

Asp Ser Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Asn Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Phe
                85                  90                  95

Thr Phe Gly Pro Gly Thr Lys Val Asp Ile Lys Arg
            100                 105

<210> SEQ ID NO 5
<211> LENGTH: 363
<212> TYPE: DNA
<213> ORGANISM: Human

<400> SEQUENCE: 5
caggtgcagc tggtgcagtc tggggctgag gtgaagaagc ctggggcctc agtgaaggtc    60
tcctgcaagg cttctggata caccttcacc agttatgata tcaactgggt gcgacaggcc   120
actggacaag gcttgagtg gatgggatgg atgaaccta acagtggtaa cacaggctat    180
gcacagaagt tccagggcag agtcaccatg accaggaaca cctccataag cacagcctac   240
atggagctga gcagcctgag atctgaggac acggccgtgt attactgtgc gagagaccct   300
tactactact actacggtat ggacgtctgg ggccaaggga ccacggtcac cgtctcctca   360
gcc                                                                363

<210> SEQ ID NO 6
<211> LENGTH: 121
<212> TYPE: PRT
<213> ORGANISM: Human

<400> SEQUENCE: 6

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Asp Pro Tyr Tyr Tyr Tyr Gly Met Asp Val Trp Gly Gln
            100                 105                 110

Gly Thr Thr Val Thr Val Ser Ser Ala
            115                 120

<210> SEQ ID NO 7
<211> LENGTH: 336
<212> TYPE: DNA
<213> ORGANISM: Human

<400> SEQUENCE: 7
cagtctgtgt tgacgcagcc gccctcagtc tctgcggccc caggacagaa ggtcaccatc     60
tcctgctctg gaagcagctc caacattgag aataatcatg tatcctggta ccagcagctc    120
ccaggaacag cccccaaact cctcatttat gacaataata gcgaccctca gggattcct    180 gaccgattct ctggctccaa gtctggcacg tcagccaccc tgggcatcac cggactccag    240
actggggacg aggccgatta ttactgcgaa acatgggata ccagcctgag tgctggccgg    300
gtattcggcg agggaccaa gctgaccgtc ctaggt                               336

<210> SEQ ID NO 8
<211> LENGTH: 112
<212> TYPE: PRT
<213> ORGANISM: Human

<400> SEQUENCE: 8

Gln Ser Val Leu Thr Gln Pro Ser Val Ser Ala Ala Pro Gly Gln
 1               5                  10                  15

Lys Val Thr Ile Ser Cys Ser Gly Ser Ser Asn Ile Glu Asn Asn
                20                  25                  30

His Val Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Glu Thr Trp Asp Thr Ser Leu
                 85                 90                  95

Ser Ala Gly Arg Val Phe Gly Gly Gly Thr Lys Leu Thr Val Leu Gly
            100                 105                 110

<210> SEQ ID NO 9
<211> LENGTH: 360
<212> TYPE: DNA
<213> ORGANISM: Human

<400> SEQUENCE: 9
caggtgcagc tgcaggagtc gggcccagga ctggtgaagc cttcggagac cctgtccctc     60
acctgcactg tctctggtgg ctccatcagt agttactact ggagctggat ccggcagccc    120
ccagggaggg gactggagtg gattggctat ttcttttaca gtgggtacac caactacaac    180
ccctccctca gagtcgcgt caccatgtca gttgacacgt ccaagaacca gttctctctg    240
aagctgagct ctgtgaccgc tgcggacacg gccgtgtatt actgtgcgtg tataactgga    300
acgacgaagg ggggtatgga cgtctggggc caaggggcca cggtcaccgt ctcctcagcc    360

<210> SEQ ID NO 10
<211> LENGTH: 120
<212> TYPE: PRT
<213> ORGANISM: Human

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Arg Gly Leu Glu Trp Ile
        35                  40                  45

Gly Tyr Phe Phe Tyr Ser Gly Tyr Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Cys Ile Thr Gly Thr Thr Lys Gly Gly Met Asp Val Trp Gly Gln Gly
            100                 105                 110

Ala Thr Val Thr Val Ser Ser Ala
            115                 120

<210> SEQ ID NO 11
<211> LENGTH: 336
<212> TYPE: DNA
<213> ORGANISM: Human

<400> SEQUENCE: 11
cagtctgtgc tgacgcaggc gccctcagtg tctggggccc cagggcagag ggtcaccatc      60
tcctgcactg ggagaagttc aacatcgggg caggttatg atgtacactg gtaccagcag     120
tttccaggaa cagccccaa actcctcatc tatggtaaca gcaatcggcc ctcaggggtc     180
cctgaccgat tctctggctc caagtctggc acctcagcct ccctggccat cactgggctc     240
caggctgagg atgaggctga ttattactgc cagtcctatg acagcagtct gagtggttcg     300
gtattcggcg agggaccaa gctgaccgtc ctaggt                               336

<210> SEQ ID NO 12
<211> LENGTH: 112
<212> TYPE: PRT
<213> ORGANISM: Human

<400> SEQUENCE: 12

Gln Ser Val Leu Thr Gln Ala Pro Ser Val Ser Gly Ala Pro Gly Gln
1               5                   10                  15

Arg Val Thr Ile Ser Cys Thr Gly Arg Ser Ser Asn Ile Gly Ala Gly
            20                  25                  30

Tyr Asp Val His Trp Tyr Gln Gln Phe Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

<210> SEQ ID NO 13
<211> LENGTH: 360
<212> TYPE: DNA
<213> ORGANISM: Human

<400> SEQUENCE: 13

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat ttcttttaca gtgggtacac caactacaac   180
ccctccctca gagtcgagt caccatatca gtagacacgt ccaagaacca gttctccctg   240
aagctgagct ctgtgaccgc tgcggacacg gccgtgtatt actgtgcgtg tataactgga   300
acgacgaagg ggggtatgga cgtctggggc caagggacca cggtcaccgt ctcctcagcc   360
```

<210> SEQ ID NO 14
<211> LENGTH: 120
<212> TYPE: PRT
<213> ORGANISM: Human

<400> SEQUENCE: 14

Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Phe Phe Tyr Ser Gly Tyr Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Cys Ile Thr Gly Thr Thr Lys Gly Gly Met Asp Val Trp Gly Gln Gly
            100                 105                 110
Thr Thr Val Thr Val Ser Ser Ala
        115                 120

<210> SEQ ID NO 15
<211> LENGTH: 336
<212> TYPE: DNA
<213> ORGANISM: Human

<400> SEQUENCE: 15

```
cagtctgtac tgacgcagcc gccctcagtg tctggggccc cagggcagag ggtcaccatc    60
tcctgcactg ggagcagctc caacatcggg gcaggttatg atgtacactg gtaccagcag   120
cttccaggaa cagcccccaa gctcctcatc tatggtaaca acaatcggcc ctcaggggtc   180
cctgaccgat tctctggctc caagtctggc acctcagcct ccctggccat cactgggctc   240
caggctgatg atgaggctga ttattactgc cagtcctttg acagcagtct gagtggttcg   300
gtattcggcg agggaccaa gctgaccgtc ctaggt                              336
```

<210> SEQ ID NO 16
<211> LENGTH: 112
<212> TYPE: PRT
<213> ORGANISM: Human

<400> SEQUENCE: 16

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Phe Asp Ser Ser
                85                  90                  95

Leu Ser Gly Ser Val Phe Gly Gly Gly Thr Lys Leu Thr Val Leu Gly
                100                 105                 110

<210> SEQ ID NO 17
<211> LENGTH: 372
<212> TYPE: DNA
<213> ORGANISM: Human

<400> SEQUENCE: 17
cagctgcagc tgcaggagtc gggcccagga ctggtgaagc cttcggagac cctgtccctc      60
acctgcactg tctctggtgg ctccatcaac agtagtagta actactgggg ctggatccgc     120
cagcccccag ggaagggact ggcgtggatt ggggggcatct attatagtgg gagcacctac    180
tacaacccgt ccctcaggag tcgagtcacc atgtccgtag acacgtccaa gaaccagttc     240
tccctgaagc tgagctctgt gaccgccgca gacacggctg tatattactg tgcgagacaa     300
aggggtcata gcagtggctg gtggtacttc gatctctggg gccgtggcac cctggtcact     360
gtctcctcag cc                                                         372

<210> SEQ ID NO 18
<211> LENGTH: 124
<212> TYPE: PRT
<213> ORGANISM: Human

<400> SEQUENCE: 18

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Asn Ser Ser
            20                  25                  30

Ser Asn Tyr Trp Gly Trp Ile Arg Gln Pro Pro Gly Lys Gly Leu Ala
        35                  40                  45

Trp Ile Gly Gly Ile Tyr Tyr Ser Gly Ser Thr Tyr Tyr Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Arg Gly His Ser Ser Gly Trp Trp Tyr Phe Asp Leu
                100                 105                 110

Trp Gly Arg Gly Thr Leu Val Thr Val Ser Ser Ala
            115                 120

<210> SEQ ID NO 19
<211> LENGTH: 324
<212> TYPE: DNA
<213> ORGANISM: Human

<400> SEQUENCE: 19
gacatccaga tgacccagtc tccatcttcc gtgtctgcat ctgtaggaga cagagtcacc      60
atcacttgtc gggcgagtcg gggtattagc agctggttag cctggtatca gcagagacca    120

```
gggaaagccc ctaagctcct gatctatact gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt tcccattcac tttcggccct    300
gggaccaaag tggatatcaa acga                                           324
```

<210> SEQ ID NO 20
<211> LENGTH: 108
<212> TYPE: PRT
<213> ORGANISM: Human

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Arg Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg
            100                 105

<210> SEQ ID NO 21
<211> LENGTH: 5
<212> TYPE: PRT
<213> ORGANISM: Human

<400> SEQUENCE: 21

Ser Tyr Tyr Trp Ser
1               5

<210> SEQ ID NO 22
<211> LENGTH: 16
<212> TYPE: PRT
<213> ORGANISM: Human

<400> SEQUENCE: 22

Tyr Phe Phe Tyr Ser Gly Tyr Thr Asn Tyr Asn Pro Ser Leu Lys Ser
1               5                   10                  15

<210> SEQ ID NO 23
<211> LENGTH: 11
<212> TYPE: PRT
<213> ORGANISM: Human

<400> SEQUENCE: 23

Ile Thr Gly Thr Thr Lys Gly Gly Met Asp Val
1               5                   10

<210> SEQ ID NO 24
<211> LENGTH: 14
<212> TYPE: PRT
<213> ORGANISM: Human

<400> SEQUENCE: 24

Thr Gly Ser Ser Ser Asn Ile Gly Ala Gly Tyr Asp Val His
1               5                   10

```
<210> SEQ ID NO 25
<211> LENGTH: 7
<212> TYPE: PRT
<213> ORGANISM: Human

<400> SEQUENCE: 25

Gly Asn Asn Asn Arg Pro Ser
1               5

<210> SEQ ID NO 26
<211> LENGTH: 11
<212> TYPE: PRT
<213> ORGANISM: Human

<400> SEQUENCE: 26

Gln Ser Phe Asp Ser Ser Leu Ser Gly Ser Val
1               5                   10

<210> SEQ ID NO 27
<211> LENGTH: 5
<212> TYPE: PRT
<213> ORGANISM: Human

<400> SEQUENCE: 27

Ser Tyr Tyr Trp Ser
1               5

<210> SEQ ID NO 28
<211> LENGTH: 16
<212> TYPE: PRT
<213> ORGANISM: Human

<400> SEQUENCE: 28

Tyr Phe Phe Tyr Ser Gly Tyr Thr Asn Tyr Asn Pro Ser Leu Lys Ser
1               5                   10                  15

<210> SEQ ID NO 29
<211> LENGTH: 11
<212> TYPE: PRT
<213> ORGANISM: Human

<400> SEQUENCE: 29

Ile Thr Gly Thr Thr Lys Gly Gly Met Asp Val
1               5                   10

<210> SEQ ID NO 30
<211> LENGTH: 14
<212> TYPE: PRT
<213> ORGANISM: Human

<400> SEQUENCE: 30

Thr Gly Arg Ser Ser Asn Ile Gly Ala Gly Tyr Asp Val His
1               5                   10

<210> SEQ ID NO 31
<211> LENGTH: 7
<212> TYPE: PRT
<213> ORGANISM: Human

<400> SEQUENCE: 31

Gly Asn Ser Asn Arg Pro Ser
1               5
```

```
<210> SEQ ID NO 32
<211> LENGTH: 11
<212> TYPE: PRT
<213> ORGANISM: Human

<400> SEQUENCE: 32

Gln Ser Tyr Asp Ser Ser Leu Ser Gly Ser Val
 1               5                  10

<210> SEQ ID NO 33
<211> LENGTH: 5
<212> TYPE: PRT
<213> ORGANISM: Human

<400> SEQUENCE: 33

Ser Tyr Asp Ile Asn
 1               5

<210> SEQ ID NO 34
<211> LENGTH: 17
<212> TYPE: PRT
<213> ORGANISM: Human

<400> SEQUENCE: 34

Trp Met Asn Pro Asn Ser Gly Asn Thr Gly Tyr Ala Gln Lys Phe Gln
 1               5                  10                  15

Gly

<210> SEQ ID NO 35
<211> LENGTH: 11
<212> TYPE: PRT
<213> ORGANISM: Human

<400> SEQUENCE: 35

Asp Pro Tyr Tyr Tyr Tyr Tyr Gly Met Asp Val
 1               5                  10

<210> SEQ ID NO 36
<211> LENGTH: 13
<212> TYPE: PRT
<213> ORGANISM: Human

<400> SEQUENCE: 36

Ser Gly Ser Ser Ser Asn Ile Glu Asn Asn His Val Ser
 1               5                  10

<210> SEQ ID NO 37
<211> LENGTH: 7
<212> TYPE: PRT
<213> ORGANISM: Human

<400> SEQUENCE: 37

Asp Asn Asn Lys Arg Pro Ser
 1               5

<210> SEQ ID NO 38
<211> LENGTH: 12
<212> TYPE: PRT
<213> ORGANISM: Human

<400> SEQUENCE: 38

Glu Thr Trp Asp Thr Ser Leu Ser Ala Gly Arg Val
 1               5                  10
```

<210> SEQ ID NO 39
<211> LENGTH: 594
<212> TYPE: DNA
<213> ORGANISM: Human

<400> SEQUENCE: 39

```
accatgaaac atctgtggtt cttcctcctg ctggtggcgg ctcccagatg ggtcctgtcc    60
cagctgcagc tgcaggagtc gggcccagga ctggtgaagc cttcggagac cctgtccctc   120
acctgcactg tctctggtgg ctccatcagg agtagtagtt actactgggg ctggatccgc   180
cagcccccag ggaaggggct ggagtggatt gggggtatct attatagtgg gagcacctac   240
tacaacccgt ctctcaagag tcgagtcacc atgtccgtag acacgtccaa gaaccagttc   300
tccctgaagc tgagctccgt gaccgccgca gacacggctg tgtattactg tgcgagacaa   360
aggggtcata gcagtggctg gtggtacttc gatctctggg gccgtggcac cctggtcact   420
gtctcctcag cctccaccaa gggcccatcg gtcttccccc tggcgccctg ctccaggagc   480
acctccgaga gcacagcggc cctgggctgc ctggtcaagg actacttccc cgaaccggtg   540
acggtgtcgt ggaactcagg cgctctgacc agcggcgtgc acaccttccc agct          594
```

<210> SEQ ID NO 40
<211> LENGTH: 198
<212> TYPE: PRT
<213> ORGANISM: Human

<400> SEQUENCE: 40

Thr Met Lys His Leu Trp Phe Phe Leu Leu Val Ala Ala Pro Arg
 1               5                  10                  15
Trp Val Leu Ser Gln Leu Gln Leu Gln Glu Ser Gly Pro Gly Leu Val
            20                  25                  30
Lys Pro Ser Glu Thr Leu Ser Leu Thr Cys Thr Val Ser Gly Gly Ser
        35                  40                  45
Ile Arg Ser Ser Ser Tyr Tyr Trp Gly Trp Ile Arg Gln Pro Pro Gly
    50                  55                  60
Lys Gly Leu Glu Trp Ile Gly Gly Ile Tyr Tyr Ser Gly Ser Thr Tyr
65                  70                  75                  80
Tyr Asn Pro Ser Leu Lys Ser Arg Val Thr Met Ser Val Asp Thr Ser
                85                  90                  95
Lys Asn Gln Phe Ser Leu Lys Leu Ser Ser Val Thr Ala Ala Asp Thr
            100                 105                 110
Ala Val Tyr Tyr Cys Ala Arg Gln Arg Gly His Ser Ser Gly Trp Trp
        115                 120                 125
Tyr Phe Asp Leu Trp Gly Arg Gly Thr Leu Val Thr Val Ser Ser Ala
    130                 135                 140
Ser Thr Lys Gly Pro Ser Val Phe Pro Leu Ala Pro Cys Ser Arg Ser
145                 150                 155                 160
Thr Ser Glu Ser Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala
        195

<210> SEQ ID NO 41
<211> LENGTH: 419
<212> TYPE: DNA
<213> ORGANISM: Human

<400> SEQUENCE: 41

```
atgagggtcc ctgctcagct cctggggctc ctgctgctct ggttcccagg ttccagatgc    60
gacatccaga tgacccagtc tccatcttcc gtgtctgcat ctgtaggaga cagtgtcacc   120
atcacttgtc gggcgagtca gggtattagc agctacttag cctggtatca gcagaaacca   180
gggaaagccc ctaaactcct gatctatgct gcatccagtt tgcaaagtgg ggtcccatca   240
aggttcagcg gcaatggatc tgggacagat ttcactctca ccatcagcag cctgcagcct   300
gaagattttg caacttacta ttgtcaacag gctaacaatt tcccattcac tttcggccct   360
gggaccaaag tggatatcaa acgaactgtg gctgcaccat ctgtcttcat cttcccgcc    419
```

<210> SEQ ID NO 42
<211> LENGTH: 139
<212> TYPE: PRT
<213> ORGANISM: Human

<400> SEQUENCE: 42

Met Arg Val Pro Ala Gln Leu Leu Gly Leu Leu Leu Leu Trp Phe Pro
 1               5                  10                  15
Gly Ser Arg Cys Asp Ile Gln Met Thr Gln Ser Pro Ser Ser Val Ser
            20                  25                  30
Ala Ser Val Gly Asp Ser Val Thr Ile Thr Cys Arg Ala Ser Gln Gly
        35                  40                  45
Ile Ser Ser Tyr Leu Ala Trp Tyr Gln Gln Lys Pro Gly Lys Ala Pro
    50                  55                  60
Lys Leu Leu Ile Tyr Ala Ala Ser Ser Leu Gln Ser Gly Val Pro Ser
65                  70                  75                  80
Arg Phe Ser Gly Asn Gly Ser Gly Thr Asp Phe Thr Leu Thr Ile Ser
                85                  90                  95
Ser Leu Gln Pro Glu Asp Phe Ala Thr Tyr Tyr Cys Gln Gln Ala Asn
            100                 105                 110
Asn Phe Pro Phe Thr Phe Gly Pro Gly Thr Lys Val Asp Ile Lys Arg
        115                 120                 125
Thr Val Ala Ala Pro Ser Val Phe Ile Phe Pro
    130                 135

<210> SEQ ID NO 43
<211> LENGTH: 437
<212> TYPE: DNA
<213> ORGANISM: Human

<400> SEQUENCE: 43

```
accatggact ggacctggag gatcctcttc ttggtggcag cagctacaag tgcccactcc    60
caggtgcagc tggtgcagtc tggggctgag gtgaagaagc ctggggcctc agtgaaggtc   120
tcctgcaagg cttctggata caccttcacc agttatgata tcaactgggt gcgacaggcc   180
actggacaag gcttgagtg gatgggatgg atgaaccta cagtggtaa cacaggctat     240
gcacagaagt tccagggcag agtcaccatg accaggaaca cctccataag cacagcctac   300
atggagctga gcagcctgag atctgaggac acggccgtgt attactgtgc gagagaccct   360
tactactact actacggtat ggacgtctgg ggccaaggga ccacggtcac cgtctcctca   420
gcctccacca agggccc                                                  437
```

<210> SEQ ID NO 44
<211> LENGTH: 145
<212> TYPE: PRT
<213> ORGANISM: Human

<400> SEQUENCE: 44

Thr Met Asp Trp Thr Trp Arg Ile Leu Phe Leu Val Ala Ala Ala Thr
1               5                   10                  15

Ser Ala His Ser Gln Val Gln Leu Val Gln Ser Gly Ala Glu Val Lys
            20                  25                  30

Lys Pro Gly Ala Ser Val Lys Val Ser Cys Lys Ala Ser Gly Tyr Thr
        35                  40                  45

Phe Thr Ser Tyr Asp Ile Asn Trp Val Arg Gln Ala Thr Gly Gln Gly
    50                  55                  60

Leu Glu Trp Met Gly Trp Met Asn Pro Asn Ser Gly Asn Thr Gly Tyr
65                  70                  75                  80

Ala Gln Lys Phe Gln Gly Arg Val Thr Met Thr Arg Asn Thr Ser Ile
                85                  90                  95

Ser Thr Ala Tyr Met Glu Leu Ser Ser Leu Arg Ser Glu Asp Thr Ala
            100                 105                 110

Val Tyr Tyr Cys Ala Arg Asp Pro Tyr Tyr Tyr Tyr Gly Met Asp
        115                 120                 125

Val Trp Gly Gln Gly Thr Thr Val Thr Val Ser Ser Ala Ser Thr Lys
    130                 135                 140

Gly
145

<210> SEQ ID NO 45
<211> LENGTH: 460
<212> TYPE: DNA
<213> ORGANISM: Human

<400> SEQUENCE: 45
atggcctggt ctcctctcct cctcacccct ctcattcact gcacagggtc ctgggcccag      60
tctgtgttga cgcagccgcc ctcagtctct gcggccccag gacagaaggt caccatctcc     120
tgctctggaa gcagctccaa cattgagaat aatcatgtat cctggtacca gcagctccca     180
ggaacagccc ccaaactcct catttatgac aataataagc gaccctcagg gattcctgac     240
cgattctctg gctccaagtc tggcacgtca gccaccctgg gcatcaccgg actccagact     300
ggggacgagg ccgattatta ctgcgaaaca tgggatacca gcctgagtgc tggcgggta     360 ttcggcggag ggaccaagct gaccgtccta ggtcagccca aggctgcccc ctcggtcact     420
ctgttcccac cctcctctga ggagctccaa gccaacaagg                           460

<210> SEQ ID NO 46
<211> LENGTH: 153
<212> TYPE: PRT
<213> ORGANISM: Human

<400> SEQUENCE: 46

Met Ala Trp Ser Pro Leu Leu Leu Thr Leu Leu Ile His Cys Thr Gly
1               5                   10                  15

Ser Trp Ala Gln Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Glu Asn Asn His Val Ser Trp Tyr Gln Gln Leu Pro Gly Thr Ala Pro
    50                  55                  60

Lys Leu Leu Ile Tyr Asp Asn Asn Lys Arg Pro Ser Gly Ile Pro Asp
65                  70                  75                  80

```
Arg Phe Ser Gly Ser Lys Ser Gly Thr Ser Ala Thr Leu Gly Ile Thr
                85                  90                  95
Gly Leu Gln Thr Gly Asp Glu Ala Asp Tyr Tyr Cys Glu Thr Trp Asp
                100                 105                 110
Thr Ser Leu Ser Ala Gly Arg Val Phe Gly Gly Gly Thr Lys Leu Thr
                115                 120                 125
Val Leu Gly Gln Pro Lys Ala Ala Pro Ser Val Thr Leu Phe Pro Pro
            130                 135                 140
Ser Ser Glu Glu Leu Gln Ala Asn Lys
145                 150
```

<210> SEQ ID NO 47
<211> LENGTH: 613
<212> TYPE: DNA
<213> ORGANISM: Human

<400> SEQUENCE: 47

```
accatgaaac atctgtggtt cttccttctc ctggtggcag ctcccagatg ggtcctgtcc      60
caggtgcagc tgcaggagtc gggcccagga ctggtgaagc cttcggagac cctgtccctc     120
acctgcactg tctctggtgg ctccatcagt agttactact ggagctggat ccggcagccc     180
ccagggaggg gactggagtg gattggctat ttcttttaca gtgggtacac caactacaac     240
ccctccctca gagtcgcgt caccatgtca gttgacacgt ccaagaacca gttctctctg     300
aagctgagct ctgtgaccgc tgcggacacg gccgtgtatt actgtgcgtg tataactgga     360
acgacgaagg ggggtatgga cgtctggggc caaggggcca cggtcaccgt ctcctcagcc     420
tccaccaagg gcccatcggt cttccccctg gcgccctgct ccaggagcac ctccgagagc     480
acagcggccc tgggctgcct ggtcaaggac tacttccccg aaccggtgac ggtgtcgtgg     540
aactcaggcg ctctgaccag cggcgtgcac accttcccag ctgtcctaca gtcctcagga     600
ctctactccc tca                                                        613
```

<210> SEQ ID NO 48
<211> LENGTH: 204
<212> TYPE: PRT
<213> ORGANISM: Human

<400> SEQUENCE: 48

```
Thr Met Lys His Leu Trp Phe Phe Leu Leu Leu Val Ala Ala Pro Arg
 1               5                  10                  15
Trp Val Leu Ser Gln Val Gln Leu Gln Glu Ser Gly Pro Gly Leu Val
                20                  25                  30
Lys Pro Ser Glu Thr Leu Ser Leu Thr Cys Thr Val Ser Gly Gly Ser
            35                  40                  45
Ile Ser Ser Tyr Tyr Trp Ser Trp Ile Arg Gln Pro Pro Gly Arg Gly
        50                  55                  60
Leu Glu Trp Ile Gly Tyr Phe Phe Tyr Ser Gly Tyr Thr Asn Tyr Asn
65                  70                  75                  80
Pro Ser Leu Lys Ser Arg Val Thr Met Ser Val Asp Thr Ser Lys Asn
                85                  90                  95
Gln Phe Ser Leu Lys Leu Ser Ser Val Thr Ala Ala Asp Thr Ala Val
                100                 105                 110
Tyr Tyr Cys Ala Cys Ile Thr Gly Thr Thr Lys Gly Gly Met Asp Val
            115                 120                 125
Trp Gly Gln Gly Ala Thr Val Thr Val Ser Ser Ala Ser Thr Lys Gly
        130                 135                 140
```

```
Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu
        195                 200
```

<210> SEQ ID NO 49
<211> LENGTH: 432
<212> TYPE: DNA
<213> ORGANISM: Human

<400> SEQUENCE: 49

```
cctctgctcc tcactctcct cgctcactgc acagggtcct gggcccagtc tgtgctgacg      60
caggcgccct cagtgtctgg ggccccaggg cagagggtca ccatctcctg cactgggaga     120
agttccaaca tcggggcagg ttatgatgta cactggtacc agcagtttcc aggaacagcc     180
cccaaactcc tcatctatgg taacagcaat cggccctcag gggtccctga ccgattctct     240
ggctccaagt ctggcacctc agcctccctg gccatcactg gctccaggc tgaggatgag      300
gctgattatt actgccagtc ctatgacagc agtctgagtg gttcggtatt cggcggaggg     360
accaagctga ccgtcctagg tcagcccaag gctgccccct cggtcactct gttcccgccc     420
tcctctgagg ag                                                          432
```

<210> SEQ ID NO 50
<211> LENGTH: 144
<212> TYPE: PRT
<213> ORGANISM: Human

<400> SEQUENCE: 50

```
Pro Leu Leu Leu Thr Leu Leu Ala His Cys Thr Gly Ser Trp Ala Gln
1               5                   10                  15

Ser Val Leu Thr Gln Ala Pro Ser Val Ser Gly Ala Pro Gly Gln Arg
            20                  25                  30

Val Thr Ile Ser Cys Thr Gly Arg Ser Ser Asn Ile Gly Ala Gly Tyr
        35                  40                  45

Asp Val His Trp Tyr Gln Gln Phe Pro Gly Thr Ala Pro Lys Leu Leu
    50                  55                  60

Ile Tyr Gly Asn Ser Asn Arg Pro Ser Gly Val Pro Asp Arg Phe Ser
65                  70                  75                  80

Gly Ser Lys Ser Gly Thr Ser Ala Ser Leu Ala Ile Thr Gly Leu Gln
                85                  90                  95

Ala Glu Asp Glu Ala Asp Tyr Tyr Cys Gln Ser Tyr Asp Ser Ser Leu
            100                 105                 110

Ser Gly Ser Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140
```

<210> SEQ ID NO 51
<211> LENGTH: 543
<212> TYPE: DNA
<213> ORGANISM: Human

-continued

<400> SEQUENCE: 51

| | |
|---|---|
| atgaagcatc tgtggttctt ccttctcctg gtggcagctc ccagatgggt cctgtcccag | 60 |
| gtgcagctgc aggagtcggg cccaggactg gtgaagcctt cggagaccct gtccctcacc | 120 |
| tgcactgtct ctggtggctc catcagtagt tactactgga gctggatccg gcagccccca | 180 |
| gggaagggac tggagtggat tgggtatttc ttttacagtg gtacaccaa ctacaacccc | 240 |
| tccctcaaga gtcgagtcac catatcagta gacacgtcca agaaccagtt ctccctgaag | 300 |
| ctgagctctg tgaccgctgc ggacacggcc gtgtattact gtgcgtgtat aactggaacg | 360 |
| acgaagggg gtatggacgt ctggggccaa gggaccacgg tcaccgtctc ctcagcctcc | 420 |
| accaagggcc catcggtctt ccccctggcg ccctgctcca ggagcacctc cgagagcaca | 480 |
| gcggccctgg gctgcctggt caaggactac ttccccgaac cggtgacggt gtcgtggaac | 540 |
| tca | 543 |

<210> SEQ ID NO 52
<211> LENGTH: 181
<212> TYPE: PRT
<213> ORGANISM: Human

<400> SEQUENCE: 52

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Tyr Tyr Trp Ser Trp Ile Arg Gln Pro Pro Gly Lys Gly Leu
    50                  55                  60

Glu Trp Ile Gly Tyr Phe Phe Tyr Ser Gly Tyr Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Cys Ile Thr Gly Thr Thr Lys Gly Gly Met Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser
            180
```

<210> SEQ ID NO 53
<211> LENGTH: 451
<212> TYPE: DNA
<213> ORGANISM: Human

<400> SEQUENCE: 53

| | |
|---|---|
| tcctctgctc ctcactctcc tcgctcactg cacagggtcc tgggcccagt ctgtactgac | 60 |
| gcagccgccc tcagtgtctg gggccccagg gcagagggtc accatctcct gcactgggag | 120 |
| cagctccaac atcggggcag gttatgatgt acactggtac cagcagcttc caggaacagc | 180 |

-continued

```
cccaagctc ctcatctatg gtaacaacaa tcggccctca ggggtccctg accgattctc    240
tggctccaag tctggcacct cagcctccct ggccatcact gggctccagg ctgatgatga    300
ggctgattat tactgccagt cctttgacag cagtctgagt ggttcggtat tcggcggagg    360
gaccaagctg accgtcctag gtcagcccaa ggctgccccc tcggtcactc tgttcccgcc    420
ctcctctgag gagctccaag ccaacaagga a                                   451
```

<210> SEQ ID NO 54
<211> LENGTH: 145
<212> TYPE: PRT
<213> ORGANISM: Human

<400> SEQUENCE: 54

```
Pro Leu Leu Leu Thr Leu Leu Ala His Cys Thr Gly Ser Trp Ala Gln
 1               5                  10                  15

Ser Val Leu Thr Gln Pro Pro Ser Val Ser Gly Ala Pro Gly Gln Arg
             20                  25                  30

Val Thr Ile Ser Cys Thr Gly Ser Ser Ser Asn Ile Gly Ala Gly Tyr
         35                  40                  45

Asp Val His Trp Tyr Gln Gln Leu Pro Gly Thr Ala Pro Lys Leu Leu
     50                  55                  60

Ile Tyr Gly Asn Asn Asn Arg Pro Ser Gly Val Pro Asp Arg Phe Ser
 65                  70                  75                  80

Gly Ser Lys Ser Gly Thr Ser Ala Ser Leu Ala Ile Thr Gly Leu Gln
                 85                  90                  95

Ala Asp Asp Glu Ala Asp Tyr Tyr Cys Gln Ser Phe Asp Ser Ser Leu
            100                 105                 110

Ser Gly Ser Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu
145
```

<210> SEQ ID NO 55
<211> LENGTH: 559
<212> TYPE: DNA
<213> ORGANISM: Human

<400> SEQUENCE: 55

```
accatgaaac atctgtggtt cttcctcctg ctggtggcgg ctcccagatg ggtcctgtcc     60
cagctgcagc tgcaggagtc gggcccagga ctggtgaagc cttcggagac cctgtccctc    120
acctgcactg tctctggtgg ctccatcaac agtagtagta actactgggg ctggatccgc    180
cagcccccag ggaagggact ggcgtggatt ggggggcatct attatagtgg gagcacctac    240
tacaacccgt ccctcaggag tcgagtcacc atgtccgtag acacgtccaa gaaccagttc    300
tccctgaagc tgagctctgt gaccgccgca gacacggctg tatattactg tgcgagacaa    360
aggggtcata gcagtggctg gtggtacttc gatctctggg gccgtggcac cctggtcact    420
gtctcctcag cctccaccaa gggcccatcg gtcttccccc tggcgccctg ctccaggagc    480
acctccgaga gcacagcggc cctgggctgc ctggtcaagg actacttccc cgaaccggtg    540
acggtgtcgt ggaactcag                                                  559
```

```
<210> SEQ ID NO 56
<211> LENGTH: 186
<212> TYPE: PRT
<213> ORGANISM: Human

<400> SEQUENCE: 56

Thr Met Lys His Leu Trp Phe Phe Leu Leu Val Ala Ala Pro Arg
 1               5                  10                  15

Trp Val Leu Ser Gln Leu Gln Leu Gln Glu Ser Gly Pro Gly Leu Val
             20                  25                  30

Lys Pro Ser Glu Thr Leu Ser Leu Thr Cys Thr Val Ser Gly Gly Ser
             35                  40                  45

Ile Asn Ser Ser Ser Asn Tyr Trp Gly Trp Ile Arg Gln Pro Pro Gly
     50                  55                  60

Lys Gly Leu Ala Trp Ile Gly Ile Tyr Tyr Ser Gly Ser Thr Tyr
 65              70                  75                  80

Tyr Asn Pro Ser Leu Arg Ser Arg Val Thr Met Ser Val Asp Thr Ser
                 85                  90                  95

Lys Asn Gln Phe Ser Leu Lys Leu Ser Ser Val Thr Ala Ala Asp Thr
             100                 105                 110

Ala Val Tyr Tyr Cys Ala Arg Gln Arg Gly His Ser Ser Gly Trp Trp
             115                 120                 125

Tyr Phe Asp Leu Trp Gly Arg Gly Thr Leu Val Thr Val Ser Ser Ala
     130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                 165                 170                 175

Pro Glu Pro Val Thr Val Ser Trp Asn Ser
             180                 185

<210> SEQ ID NO 57
<211> LENGTH: 532
<212> TYPE: DNA
<213> ORGANISM: Human

<400> SEQUENCE: 57
atgagggtcc ccgctcagct cctggggctc ctgctgctct ggttcccagg ttccagatgc      60
gacatccaga tgacccagtc tccatcttcc gtgtctgcat ctgtaggaga cagagtcacc     120
atcacttgtc gggcgagtcg gggtattagc agctggttag cctggtatca gcagagacca     180
gggaaagccc ctaagctcct gatctatact gcatccagtt tgcaaagtgg ggtcccatca     240
aggttcagcg gcagtggatc tgggacagat ttcactctca ccatcagcag cctgcagcct     300
gaagattttg caacttacta ttgtcaacag gctaacagtt tcccattcac tttcggccct     360
gggaccaaag tggatatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg ataacgccc tccaatcggg ta               532

<210> SEQ ID NO 58
<211> LENGTH: 177
<212> TYPE: PRT
<213> ORGANISM: Human
```

<400> SEQUENCE: 58

Met Arg Val Pro Ala Gln Leu Leu Gly Leu Leu Leu Trp Phe Pro
1               5                   10                  15

Gly Ser Arg Cys Asp Ile Gln Met Thr Gln Ser Pro Ser Val Ser
            20                  25                  30

Ala Ser Val Gly Asp Arg Val Thr Ile Thr Cys Arg Ala Ser Arg Gly
        35                  40                  45

Ile Ser Ser Trp Leu Ala Trp Tyr Gln Gln Arg Pro Gly Lys Ala Pro
    50                  55                  60

Lys Leu Leu Ile Tyr Thr Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ser Phe Pro Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly

<210> SEQ ID NO 59
<211> LENGTH: 594
<212> TYPE: DNA
<213> ORGANISM: Human

<400> SEQUENCE: 59
accatgaaac atctgtggtt cttcctcctg ctggtggcgg ctcccagatg ggtcctgtcc      60
cagctgcagc tgcaggagtc gggcccagga ctggtgaagc cttcggagac cctgtccctc    120
acctgcactg tctctggtgg ctccatcagc agtagtagtt actactgggg ctggatccgc    180
cagcccccag ggaaggggct ggagtggatt gggggtatct attatagtgg gagcacctac    240
tacaacccgt ctctcaagag tcgagtcatc atgtccgtag acacgtccaa gaaccagttc    300
tccctgaagc tgagctccgt gaccgccgca gacacggctg tgtattactg tgcgagacaa    360 agggtcata gcagtggctg gtggtacttc gatctctggg gccgtggcac cctggtcact    420
gtctcctcag cctccaccaa gggcccatcg gtcttccccc tggcgccctg ctccaggagc    480
acctccgaga gcacagcggc cctgggctgc ctggtcaagg actacttccc cgaaccggtg    540
acggtgtcgt ggaactcagg cgctctgacc agcggcgtgc acaccttccc agct           594

<210> SEQ ID NO 60
<211> LENGTH: 198
<212> TYPE: PRT
<213> ORGANISM: Human

<400> SEQUENCE: 60

Thr Met Lys His Leu Trp Phe Phe Leu Leu Leu Val Ala Ala Pro Arg
1               5                   10                  15

Trp Val Leu Ser Gln Leu Gln Leu Gln Glu Ser Gly Pro Gly Leu Val
            20                  25                  30

```
Lys Pro Ser Glu Thr Leu Ser Leu Thr Cys Thr Val Ser Gly Gly Ser
            35                  40                  45

Ile Ser Ser Ser Ser Tyr Tyr Trp Gly Trp Ile Arg Gln Pro Pro Gly
 50                      55                  60

Lys Gly Leu Glu Trp Ile Gly Gly Ile Tyr Tyr Ser Gly Ser Thr Tyr
 65                  70                  75                  80

Tyr Asn Pro Ser Leu Lys Ser Arg Val Thr Ile Ser Val Asp Thr Ser
                 85                  90                  95

Lys Asn Gln Phe Ser Leu Lys Leu Ser Ser Val Thr Ala Ala Asp Thr
            100                 105                 110

Ala Val Tyr Tyr Cys Ala Arg Gln Arg Gly His Ser Ser Gly Trp Trp
            115                 120                 125

Tyr Phe Asp Leu Trp Gly Arg Gly Thr Leu Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala
            195

<210> SEQ ID NO 61
<211> LENGTH: 419
<212> TYPE: DNA
<213> ORGANISM: Human

<400> SEQUENCE: 61
atgagggtcc ctgctcagct cctggggctc ctgctgctct ggttcccagg ttccagatgc     60
gacatccaga tgacccagtc tccatcttcc gtgtctgcat ctgtaggaga cagagtcacc    120
atcacttgtc gggcgagtca gggtattagc agctacttag cctggtatca gcagaaacca    180
gggaaagccc ctaaactcct gatctatgct gcatccagtt tgcaaagtgg ggtcccatca    240
aggttcagcg gcagtggatc tgggacagat ttcactctca ccatcagcag cctgcagcct    300
gaagattttg caacttacta ttgtcaacag gctaacaatt tcccattcac tttcggccct    360
gggaccaaag tggatatcaa acgaactgtg gctgcaccat ctgtcttcat cttcccgcc    419

<210> SEQ ID NO 62
<211> LENGTH: 139
<212> TYPE: PRT
<213> ORGANISM: Human

<400> SEQUENCE: 62

Met Arg Val Pro Ala Gln Leu Leu Gly Leu Leu Leu Leu Trp Phe Pro
 1               5                  10                  15

Gly Ser Arg Cys Asp Ile Gln Met Thr Gln Ser Pro Ser Ser Val Ser
            20                  25                  30

Ala Ser Val Gly Asp Arg Val Thr Ile Thr Cys Arg Ala Ser Gln Gly
            35                  40                  45

Ile Ser Ser Tyr Leu Ala Trp Tyr Gln Gln Lys Pro Gly Lys Ala Pro
 50                      55                  60

Lys Leu Leu Ile Tyr Ala Ala Ser Ser Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95
```

```
Ser Leu Gln Pro Glu Asp Phe Ala Thr Tyr Tyr Cys Gln Gln Ala Asn
            100                 105                 110

Asn Phe Pro Phe Thr Phe Gly Pro Gly Thr Lys Val Asp Ile Lys Arg
        115                 120                 125

Thr Val Ala Ala Pro Ser Val Phe Ile Phe Pro
    130                 135
```

<210> SEQ ID NO 63
<211> LENGTH: 437
<212> TYPE: DNA
<213> ORGANISM: Human

<400> SEQUENCE: 63

```
accatggact ggacctggag gatcctcttc ttggtggcag cagctacaag tgcccactcc      60
caggtgcagc tggtgcagtc tggggctgag gtgaagaagc ctggggcctc agtgaaggtc     120
tcctgcaagg cttctggata caccttcacc agttatgata tcaactgggt gcgacaggcc     180
actggacaag gcttgagtg gatgggatgg atgaaccta acagtggtaa cacaggctat      240
gcacagaagt tccagggcag agtcaccatg accaggaca cctccataag cacagcctac      300
atggagctga gcagcctgag atctgaggac acggccgtgt attactgtgc gagagaccct     360
tactactact actacggtat ggacgtctgg ggccaaggga ccacggtcac cgtctcctca     420
gcctccacca agggccc                                                    437
```

<210> SEQ ID NO 64
<211> LENGTH: 145
<212> TYPE: PRT
<213> ORGANISM: Human

<400> SEQUENCE: 64

```
Thr Met Asp Trp Thr Trp Arg Ile Leu Phe Leu Val Ala Ala Ala Thr
  1               5                  10                  15

Ser Ala His Ser Gln Val Gln Leu Val Gln Ser Gly Ala Glu Val Lys
             20                  25                  30

Lys Pro Gly Ala Ser Val Lys Val Ser Cys Lys Ala Ser Gly Tyr Thr
         35                  40                  45

Phe Thr Ser Tyr Asp Ile Asn Trp Val Arg Gln Ala Thr Gly Gln Gly
     50                  55                  60

Leu Glu Trp Met Gly Trp Met Asn Pro Asn Ser Gly Asn Thr Gly Tyr
 65                  70                  75                  80

Ala Gln Lys Phe Gln Gly Arg Val Thr Met Thr Arg Asp Thr Ser Ile
                 85                  90                  95

Ser Thr Ala Tyr Met Glu Leu Ser Ser Leu Arg Ser Glu Asp Thr Ala
            100                 105                 110

Val Tyr Tyr Cys Ala Arg Asp Pro Tyr Tyr Tyr Tyr Gly Met Asp
        115                 120                 125

Val Trp Gly Gln Gly Thr Thr Val Thr Val Ser Ser Ala Ser Thr Lys
    130                 135                 140

Gly
145
```

<210> SEQ ID NO 65
<211> LENGTH: 460
<212> TYPE: DNA
<213> ORGANISM: Human

-continued

```
<400> SEQUENCE: 65
atggcctggt ctcctctcct cctcacccct ctcattcact gcacagggtc ctgggcccag      60
tctgtgttga cgcagccgcc ctcagtctct gcggccccag gacagaaggt caccatctcc     120
tgctctggaa gcagctccaa cattgagaat aatcatgtat cctggtacca gcagctccca     180
ggaacagccc ccaaactcct catttatgac aataataagc gaccctcagg gattcctgac     240
cgattctctg ctccaagtc tggcacgtca gccaccctgg gcatcaccgg actccagact      300
ggggacgagg ccgattatta ctgcgaaaca tgggatacca gcctgagtgc tggccgggta     360
ttcggcggag ggaccaagct gaccgtccta ggtcagccca aggctgcccc ctcggtcact     420
ctgttcccac cctcctctga ggagctccaa gccaacaagg                           460

<210> SEQ ID NO 66
<211> LENGTH: 153
<212> TYPE: PRT
<213> ORGANISM: Human

<400> SEQUENCE: 66

Met Ala Trp Ser Pro Leu Leu Leu Thr Leu Leu Ile His Cys Thr Gly
 1               5                  10                  15

Ser Trp Ala Gln Ser Val Leu Thr Gln Pro Pro Ser Val Ser Ala Ala
             20                  25                  30

Pro Gly Gln Lys Val Thr Ile Ser Cys Ser Gly Ser Ser Ser Asn Ile
         35                  40                  45

Glu Asn Asn His Val Ser Trp Tyr Gln Gln Leu Pro Gly Thr Ala Pro
     50                  55                  60

Lys Leu Leu Ile Tyr Asp Asn Asn Lys Arg Pro Ser Gly Ile Pro Asp
 65                  70                  75                  80

Arg Phe Ser Gly Ser Lys Ser Gly Thr Ser Ala Thr Leu Gly Ile Thr
                 85                  90                  95

Gly Leu Gln Thr Gly Asp Glu Ala Asp Tyr Tyr Cys Glu Thr Trp Asp
            100                 105                 110

Thr Ser Leu Ser Ala Gly Arg Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys
145                 150

<210> SEQ ID NO 67
<211> LENGTH: 613
<212> TYPE: DNA
<213> ORGANISM: Human

<400> SEQUENCE: 67
accatgaaac atctgtggtt cttccttctc ctggtggcag ctcccagatg gtcctgtcc       60
caggtgcagc tgcaggagtc gggcccagga ctggtgaagc cttcggagac cctgtccctc    120
acctgcactg tctctggtgg ctccatcagt agttactact ggagctggat ccggcagccc    180
ccagggaagg gactggagtg gattggctat ttcttttaca gtgggtacac caactacaac    240
ccctccctca gagtcgcgt caccatctca gttgacacgt ccaagaacca gttctctctg    300
aagctgagct ctgtgaccgc tgcggacacg gccgtgtatt actgtgcgcg tataactgga    360
acgacgaagg ggggtatgga cgtctggggc caagggacca cggtcaccgt ctcctcagcc    420
tccaccaagg gcccatcggt cttccccctg gcgccctgct ccaggagcac ctccgagagc    480
```

```
acagcggccc tgggctgcct ggtcaaggac tacttccccg aaccggtgac ggtgtcgtgg      540
aactcaggcg ctctgaccag cggcgtgcac accttcccag ctgtcctaca gtcctcagga      600
ctctactccc tca                                                        613
```

<210> SEQ ID NO 68
<211> LENGTH: 204
<212> TYPE: PRT
<213> ORGANISM: Human

<400> SEQUENCE: 68

| Thr | Met | Lys | His | Leu | Trp | Phe | Phe | Leu | Leu | Val | Ala | Ala | Pro | Arg |
|---|---|---|---|---|---|---|---|---|---|---|---|---|---|---|
| 1 | | | | 5 | | | | | 10 | | | | | 15 |

| Trp | Val | Leu | Ser | Gln | Val | Gln | Leu | Gln | Glu | Ser | Gly | Pro | Gly | Leu | Val |
|---|---|---|---|---|---|---|---|---|---|---|---|---|---|---|---|
| | | | 20 | | | | | 25 | | | | | 30 | | |

Lys Pro Ser Glu Thr Leu Ser Leu Thr Cys Thr Val Ser Gly Gly Ser
             35                  40                  45

Ile Ser Ser Tyr Tyr Trp Ser Trp Ile Arg Gln Pro Pro Gly Lys Gly
         50                  55                  60

Leu Glu Trp Ile Gly Tyr Phe Phe Tyr Ser Gly Tyr Thr Asn Tyr Asn
65                  70                  75                  80

Pro Ser Leu Lys Ser Arg Val Thr Ile Ser Val Asp Thr Ser Lys Asn
                 85                  90                  95

Gln Phe Ser Leu Lys Leu Ser Ser Val Thr Ala Ala Asp Thr Ala Val
            100                 105                 110

Tyr Tyr Cys Ala Arg Ile Thr Gly Thr Thr Lys Gly Gly Met Asp Val
        115                 120                 125

Trp Gly Gln Gly Thr Thr Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu
        195                 200

<210> SEQ ID NO 69
<211> LENGTH: 432
<212> TYPE: DNA
<213> ORGANISM: Human

<400> SEQUENCE: 69

```
cctctgctcc tcactctcct cgctcactgc acagggtcct gggcccagtc tgtgctgacg      60
cagccgccct cagtgtctgg ggccccaggg cagagggtca ccatctcctg cactgggaga      120
agttccaaca tcggggcagg ttatgatgta cactggtacc agcagttgcc aggaacagcc      180
cccaaactcc tcatctatgg taacagcaat cggccctcag gggtccctga ccgattctct      240
ggctccaagt ctggcacctc agcctccctg gccatcactg gctccaggc tgaggatgag      300 gctgattatt actgccagtc ctatgacagc agtctgagtg ttcggtatt cggcggaggg      360 accaagctga ccgtcctagg tcagcccaag gctgccccct cggtcactct gttcccgccc      420
tcctctgagg ag                                                         432
```

<210> SEQ ID NO 70
<211> LENGTH: 144
<212> TYPE: PRT
<213> ORGANISM: Human

<400> SEQUENCE: 70

Pro Leu Leu Leu Thr Leu Leu Ala His Cys Thr Gly Ser Trp Ala Gln
1               5                   10                  15

Ser Val Leu Thr Gln Pro Pro Ser Val Ser Gly Ala Pro Gly Gln Arg
            20                  25                  30

Val Thr Ile Ser Cys Thr Gly Arg Ser Ser Asn Ile Gly Ala Gly Tyr
        35                  40                  45

Asp Val His Trp Tyr Gln Gln Leu Pro Gly Thr Ala Pro Lys Leu Leu
    50                  55                  60

Ile Tyr Gly Asn Ser Asn Arg Pro Ser Gly Val Pro Asp Arg Phe Ser
65                  70                  75                  80

Gly Ser Lys Ser Gly Thr Ser Ala Ser Leu Ala Ile Thr Gly Leu Gln
                85                  90                  95

Ala Glu Asp Glu Ala Asp Tyr Tyr Cys Gln Ser Tyr Asp Ser Ser Leu
            100                 105                 110

Ser Gly Ser Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

<210> SEQ ID NO 71
<211> LENGTH: 543
<212> TYPE: DNA
<213> ORGANISM: Human

<400> SEQUENCE: 71
atgaagcatc tgtggttctt ccttctcctg gtggcagctc ccagatgggt cctgtcccag      60
gtgcagctgc aggagtcggg cccaggactg gtgaagcctt cggagaccct gtccctcacc     120
tgcactgtct ctggtggctc catcagtagt tactactgga gctggatccg gcagccccca     180
gggaagggac tggagtggat tgggtatttc ttttacagtg gtacaccaa ctacaacccc      240 tccctcaaga gtcgagtcac catatcagta gacacgtcca agaaccagtt ctccctgaag     300
ctgagctctg tgaccgctgc ggacacggcc gtgtattact gtgcgcgtat aactggaacg     360
acgaaggggg gtatgacgt ctggggccaa gggaccacgg tcaccgtctc ctcagcctcc      420
accaagggcc catcggtctt ccccctggcg ccctgctcca ggagcacctc cgagagcaca     480
gcggccctgg gctgcctggt caaggactac ttccccgaac cggtgacggt gtcgtggaac     540
tca                                                                  543

<210> SEQ ID NO 72
<211> LENGTH: 181
<212> TYPE: PRT
<213> ORGANISM: Human

<400> SEQUENCE: 72

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

```
Ser Ser Tyr Tyr Trp Ser Trp Ile Arg Gln Pro Pro Gly Lys Gly Leu
 50                  55                  60

Glu Trp Ile Gly Tyr Phe Phe Tyr Ser Gly Tyr Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Ala Arg Ile Thr Gly Thr Thr Lys Gly Gly Met Asp Val Trp
            115                 120                 125

Gly Gln Gly Thr Thr Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
            165                 170                 175

Val Ser Trp Asn Ser
            180

<210> SEQ ID NO 73
<211> LENGTH: 451
<212> TYPE: DNA
<213> ORGANISM: Human

<400> SEQUENCE: 73
tcctctgctc ctcactctcc tcgctcactg cacagggtcc tgggcccagt ctgtactgac      60
gcagccgccc tcagtgtctg ggccccagg gcagagggtc accatctcct gcactgggag     120
cagctccaac atcggggcag gttatgatgt acactggtac cagcagcttc caggaacagc     180
ccccaagctc ctcatctatg gtaacaacaa tcggccctca ggggtccctg accgattctc     240
tggctccaag tctggcacct cagcctccct ggccatcact gggctccagg ctgaagatga     300
ggctgattat tactgccagt cctttgacag cagtctgagt ggttcggtat tcggcggagg     360
gaccaagctg accgtcctag gtcagcccaa ggctgccccc tcggtcactc tgttcccgcc     420
ctcctctgag gagctccaag ccaacaagga a                                    451

<210> SEQ ID NO 74
<211> LENGTH: 145
<212> TYPE: PRT
<213> ORGANISM: Human

<400> SEQUENCE: 74

Pro Leu Leu Leu Thr Leu Leu Ala His Cys Thr Gly Ser Trp Ala Gln
  1               5                  10                  15

Ser Val Leu Thr Gln Pro Pro Ser Val Ser Gly Ala Pro Gly Gln Arg
                 20                  25                  30

Val Thr Ile Ser Cys Thr Gly Ser Ser Ser Asn Ile Gly Ala Gly Tyr
            35                  40                  45

Asp Val His Trp Tyr Gln Gln Leu Pro Gly Thr Ala Pro Lys Leu Leu
 50                  55                  60

Ile Tyr Gly Asn Asn Asn Arg Pro Ser Gly Val Pro Asp Arg Phe Ser
 65                  70                  75                  80

Gly Ser Lys Ser Gly Thr Ser Ala Ser Leu Ala Ile Thr Gly Leu Gln
                 85                  90                  95

Ala Glu Asp Glu Ala Asp Tyr Tyr Cys Gln Ser Phe Asp Ser Ser Leu
            100                 105                 110
```

```
Ser Gly Ser Val Phe Gly Gly Thr Lys Leu Thr Val Leu Gly Gln
        115                 120                 125

Pro Lys Ala Ala Pro Ser Val Thr Leu Phe Pro Pro Ser Ser Glu Glu
    130                 135                 140

Leu
145

<210> SEQ ID NO 75
<211> LENGTH: 119
<212> TYPE: PRT
<213> ORGANISM: Human

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser Ala
        115

<210> SEQ ID NO 76
<211> LENGTH: 110
<212> TYPE: PRT
<213> ORGANISM: Human

<400> SEQUENCE: 76

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Phe Gly Gly Gly Thr Lys Leu Thr Val Leu Gly
            100                 105                 110

<210> SEQ ID NO 77
<211> LENGTH: 118
<212> TYPE: PRT
<213> ORGANISM: Human
```

<400> SEQUENCE: 77

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Ser Trp Tyr Phe Asp Leu Trp Gly Arg Gly Thr Leu
            100                 105                 110

Val Thr Val Ser Ser Ala
        115

<210> SEQ ID NO 78
<211> LENGTH: 108
<212> TYPE: PRT
<213> ORGANISM: Human

<400> SEQUENCE: 78

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg
            100                 105

<210> SEQ ID NO 79
<211> LENGTH: 117
<212> TYPE: PRT
<213> ORGANISM: Human

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ile Thr Gly Thr Gly Met Asp Val Trp Gly Gln Gly Thr Thr Val
                100                 105                 110

Thr Val Ser Ser Ala
        115

<210> SEQ ID NO 80
<211> LENGTH: 112
<212> TYPE: PRT
<213> ORGANISM: Human

<400> SEQUENCE: 80

Gln Ser Val Leu Thr Gln Pro Pro Ser Val Ser Gly Ala Pro Gly Gln
  1               5                  10                  15

Arg Val Thr Ile Ser Cys Thr Gly Ser Ser Asn Ile Gly Ala Gly
                 20                  25                  30

Tyr Asp Val His Trp Tyr Gln Gln Leu Pro Gly Thr Ala Pro Lys Leu
                 35                  40                  45

Leu Ile Tyr Gly Asn Ser Asn Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Thr Lys Leu Thr Val Leu Gly
                100                 105                 110

<210> SEQ ID NO 81
<211> LENGTH: 7
<212> TYPE: PRT
<213> ORGANISM: Human

<400> SEQUENCE: 81

Ser Ser Ser Tyr Tyr Trp Gly
  1               5

<210> SEQ ID NO 82
<211> LENGTH: 16
<212> TYPE: PRT
<213> ORGANISM: Human

<400> SEQUENCE: 82

Gly Ile Tyr Tyr Ser Gly Ser Thr Tyr Tyr Asn Pro Ser Leu Lys Ser
  1               5                  10                  15

<210> SEQ ID NO 83
<211> LENGTH: 13
<212> TYPE: PRT
<213> ORGANISM: Human

<400> SEQUENCE: 83

Gln Arg Gly His Ser Ser Gly Trp Tyr Phe Asp Leu
  1               5                  10

<210> SEQ ID NO 84
<211> LENGTH: 11
<212> TYPE: PRT
<213> ORGANISM: Human

<400> SEQUENCE: 84

Arg Ala Ser Gln Gly Ile Ser Ser Tyr Leu Ala
  1               5                  10

```
<210> SEQ ID NO 85
<211> LENGTH: 7
<212> TYPE: PRT
<213> ORGANISM: Human

<400> SEQUENCE: 85

Ala Ala Ser Ser Leu Gln Ser
1               5

<210> SEQ ID NO 86
<211> LENGTH: 9
<212> TYPE: PRT
<213> ORGANISM: Human

<400> SEQUENCE: 86

Gln Gln Ala Asn Asn Phe Pro Phe Thr
1               5

<210> SEQ ID NO 87
<211> LENGTH: 7
<212> TYPE: PRT
<213> ORGANISM: Human

<400> SEQUENCE: 87

Ser Ser Ser Asn Tyr Trp Gly
1               5

<210> SEQ ID NO 88
<211> LENGTH: 16
<212> TYPE: PRT
<213> ORGANISM: Human

<400> SEQUENCE: 88

Gly Ile Tyr Tyr Ser Gly Ser Thr Tyr Tyr Asn Pro Ser Leu Arg Ser
1               5                   10                  15

<210> SEQ ID NO 89
<211> LENGTH: 13
<212> TYPE: PRT
<213> ORGANISM: Human

<400> SEQUENCE: 89

Gln Arg Gly His Ser Ser Gly Trp Trp Tyr Phe Asp Leu
1               5                   10

<210> SEQ ID NO 90
<211> LENGTH: 11
<212> TYPE: PRT
<213> ORGANISM: Human

<400> SEQUENCE: 90

Arg Ala Ser Arg Gly Ile Ser Ser Trp Leu Ala
1               5                   10

<210> SEQ ID NO 91
<211> LENGTH: 7
<212> TYPE: PRT
<213> ORGANISM: Human

<400> SEQUENCE: 91

Thr Ala Ser Ser Leu Gln Ser
1               5
```

```
<210> SEQ ID NO 92
<211> LENGTH: 9
<212> TYPE: PRT
<213> ORGANISM: Human

<400> SEQUENCE: 92

Gln Gln Ala Asn Ser Phe Pro Phe Thr
1               5

<210> SEQ ID NO 93
<211> LENGTH: 25
<212> TYPE: PRT
<213> ORGANISM: Human

<400> SEQUENCE: 93

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 94
<211> LENGTH: 10
<212> TYPE: PRT
<213> ORGANISM: Human

<400> SEQUENCE: 94

Gly Tyr Thr Phe Thr Ser Tyr Asp Ile Asn
1               5                   10

<210> SEQ ID NO 95
<211> LENGTH: 25
<212> TYPE: PRT
<213> ORGANISM: Human

<400> SEQUENCE: 95

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 96
<211> LENGTH: 12
<212> TYPE: PRT
<213> ORGANISM: Human

<400> SEQUENCE: 96

Gly Gly Ser Ile Arg Ser Ser Tyr Tyr Trp Gly
1               5                   10

<210> SEQ ID NO 97
<211> LENGTH: 25
<212> TYPE: PRT
<213> ORGANISM: Human

<400> SEQUENCE: 97

Gln Leu Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 98
<211> LENGTH: 12
<212> TYPE: PRT
<213> ORGANISM: Human
```

```
<400> SEQUENCE: 98

Gly Gly Ser Ile Asn Ser Ser Ser Asn Tyr Trp Gly
1               5                   10

<210> SEQ ID NO 99
<211> LENGTH: 25
<212> TYPE: PRT
<213> ORGANISM: Human

<400> SEQUENCE: 99

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 100
<211> LENGTH: 10
<212> TYPE: PRT
<213> ORGANISM: Human

<400> SEQUENCE: 100

Gly Gly Ser Ile Ser Ser Tyr Tyr Trp Ser
1               5                   10

<210> SEQ ID NO 101
<211> LENGTH: 25
<212> TYPE: PRT
<213> ORGANISM: Human

<400> SEQUENCE: 101

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 102
<211> LENGTH: 10
<212> TYPE: PRT
<213> ORGANISM: Human

<400> SEQUENCE: 102

Gly Gly Ser Ile Ser Ser Tyr Tyr Trp Ser
1               5                   10
```

INSULIN-LIKE GROWTH FACTOR ANTIBODIES AND USES THEREOF

CROSS-REFERENCE TO RELATED APPLICATIONS

This application claims priority under 35 U.S.C. §119 to U.S. Provisional Application Ser. No. 60/750,085, filed Dec. 13, 2005; U.S. Provisional Application Ser. No. 60/750,772, filed Dec. 14, 2005; U.S. Provisional Application Ser. No. 60/774,747, filed Feb. 17, 2005; and U.S. Provisional Application Ser. No. 60/808,183, filed May 24, 2006, each of which is incorporated herein by reference in its entirety.

REFERENCE TO SEQUENCE LISTING

The present application is being filed along with a Sequence Listing in electronic format. The Sequence Listing is provided as a file entitled ABXAZ.004A.TXT, created Dec. 8, 2006, which is 65 Kb in size. The information in the electronic format of the Sequence Listing is incorporated herein by reference in its entirety:

BACKGROUND OF THE INVENTION

1. Field of the Invention

The invention relates to binding proteins that bind to insulin-like growth factor-2 (IGF-II) with cross-reactivity to insulin-like growth factor-1 (IGF-I) and uses of such binding proteins. More specifically, the invention relates to monoclonal antibodies directed to IGF-II with cross-reactivity to IGF-I and uses of these antibodies. Aspects of the invention also relate to hybridomas or other cell lines expressing such antibodies.

2. Description of the Related Art

Insulin-like growth factor IGF-I and IGF-II are small polypeptides involved in regulating cell proliferation, survival, differentiation and transformation. IGFs exert their various actions by primarily interacting with a specific cell surface receptor, the IGF-I receptor (IGF-IR) and activating various intracellular signaling cascades. IGFs circulate in serum mostly bound to IGF-binding proteins (IGFBP-1 to 6). The interaction of IGFs with the IGF-IR is regulated by the IGFBPs, and IGFs can only bind to the IGF-IR once released from the IGFBPs (mostly by proteolysis of the IGFBPs). IGF-I can also bind to a hybrid receptor comprised of IGF-IR and insulin receptor (IR) subunits. IGF-II has been shown to bind to the "A" isoform of the insulin receptor.

Malignant transformation involves the imbalance of diverse processes such as cell growth, differentiation, apoptosis, and transformation. IGF-I and IGF-II have been implicated in the pathophysiology of a wide range of conditions, and are thought to play a role in tumorigenesis due to the mitogenic and antiapoptotic properties mediated by the receptor IGF-IR. LeRoith and Roberts, *Cancer Lett.* 195:127-137 (2003).

IGF-I was discovered as a growth factor produced by the liver under the regulatory control of pituitary growth hormone and was originally designated somatomedin-C. Salmon et al., *J. Lab. Clin. Med.* 49:825-826 (1957). Both IGF-I and IGF-II are expressed ubiquitously and act as endocrine, paracrine, and autocrine growth factors, through their interaction with the IGF-IR, a trans-membrane tyrosine kinase that is structurally and functionally related to the insulin receptor (IR). IGF-I functions primarily by activating the IGF-IR, whereas IGF-II can act through either the IGF-IR or through the IR-A isoform. LeRoith and Roberts, Cancer Lett. 195:127-137 (2003). Additionally, the interaction of both IGF-I and IGF-II with the IGF-binding proteins may affect the half-life and bioavailability of the IGFs, as well as their direct interaction with receptors in some cases. Rajaram et al., *Endocr. Rev.* 18:801-831 (1997).

IGF-I has a long-term impact on cell proliferation, differentiation, and apoptosis. Experiments in cultured osteosarcoma and breast cancer cells suggested that IGF-I is a potent mitogen and exerts its mitogenic action by increasing DNA synthesis and by stimulating the expression of cyclin DI, which accelerates progression of the cell cycle from $G_1$ to S phase. Furlanetto et al., *Mol. Endocrinol.* 8:510-517 (1994); Dufourny et al., *J. Biol. Chem.* 272:311663-31171 (1997). Suppression of cyclin D1 expression in pancreatic cancer cells abolished the mitogenic effect of IGF-I. Kornmann et al., *J. Clin. Invest.* 101:344-352 (1998). In addition to stimulating cell cycle progression, IGF-I also inhibits apoptosis. IGF-I was shown to stimulate the expression of Bcl proteins and to suppress expression of Bax, which results in an increase in the relative amount of the Bcl/Bax heterodimer, thereby blocking initiation of the apoptotic pathway. Minshall et al., *J. Immunol.* 159:1225-1232 (1997); Parrizas et al., *Endocrinology* 138:1355-1358 (1997); Wang et al., *Endocrinology* 139:1354-1360 (1998).

Like IGF-I, IGF-II also has mitogenic and antiapoptotic actions and regulates cell proliferation and differentiation. Compared with IGF-I, high concentrations of IGF-II circulate in serum. High serum IGF-II concentrations have been found in patients with colorectal cancer, with a trend towards higher concentrations in advanced disease. Renehan et al., *Br. J. Cancer* 83:1344-1350. Additionally, most primary tumors and transformed cell lines overexpress IGF-II MRNA and protein. Werner and LeRoith *Adv. Cancer Res.* 68:183-223 (1996). Overexpression of IGF-II in colon cancer is associated with an aggressive phenotype, and the loss of imprinting (loss of allele-specific expression) of the IGF-II gene may be important in colorectal carcinogenesis. Michell et al., *Br. J. Cancer* 76:60-66 (1997); Takano et al., *Oncology* 59:210-216 (2000). Cancer cells with a strong tendency to metastasize have four-fold higher levels of IGF-II expression than those cells with a low ability to metastasize. Guerra et al., *Int. J. Cancer* 65:812-820 (1996).

Research and clinical studies have highlighted the role of the IGF family members in the development, maintenance and progression of cancer. Many cancer cells have been shown to overexpress the IGF-IR and/or the IGF ligands. For example, IGF-I and IGF-II are strong mitogens for a wide variety of cancer cell lines, including sarcoma, leukemia, and cancers of the prostate, breast, lung, colon, stomach, esophagus, liver, pancreas, kidney, thyroid, brain, ovary, and uterus. Macaulay et al., *Br. J. Cancer* 65:311-320 (1992); Oku et al., *Anticancer Res.* 11: 1591-1595 (1991); LeRoith et al., *Ann. Intern. Med.* 122:54-59 (1995); Yaginuma et al., *Oncology* 54:502-507 (1997); Singh et al., *Endocrinology* 137:1764-1774 (1996); Frostad et al., *Eur. J. Haematol* 62:191-198 (1999). When IGF-I was administered to malignant colon cancer cells, they became resistant to cytokine-induced apoptosis. Remacle-Bonnet et al., *Cancer Res.* 60:2007-2017 (2000).

The role of IGFs in cancer is also supported by epidemiologic studies, which showed that high levels of circulating IGF-I and low levels of IGFBP-3 are associated with an increased risk for development of several common cancers (prostate, breast, colorectal and lung). Mantzoros et al., *Br. J. Cancer* 76:1115-1118 (1997); Hankinson et al., *Lancet* 351: 1393-1396 (1998); Ma et al., *J. Natl. Cancer Inst.* 91:620-625 (1999); Karasik et al., *J. Clin. Endocrinol Metab.* 78:271-276

(1994). These results suggest that IGF-I and IGF-II act as powerful mitogenic and anti-apoptotic signals, and that their overexpression correlates with poor prognosis in patients with several types of cancer.

Using knockout mouse models, several studies have further established the role of IGFs in tumor growth. With the development of the technology for tissue specific, conditional gene deletion, a mouse model of liver IGF-I deficiency (LID) was developed. Liver-specific deletion of the igf1 gene abrogated expression of IGF-I mRNA and caused a dramatic reduction in circulating IGF-I levels. Yakar. et al., *Proc. Natl. Acad. Sci. USA* 96:7324-7329 (1999). When mammary tumors were induced in the LID mouse, reduced circulating IGF-1 levels resulted in significant reductions in cancer development, growth, and metastases, whereas increased circulating IGF-1 levels were associated with enhanced tumor growth. Wu et al., *Cancer Res.* 63:4384-4388 (2003).

Several papers have reported that inhibition of IGF-IR expression and/or signaling leads to inhibition of tumor growth, both in vitro and in vivo. Inhibition of IGF signaling has also been shown to increase the susceptibility of tumor cells to chemotherapeutic agents. A variety of strategies (antisense oligonucleotides, soluble receptor, inhibitory peptides, dominant negative receptor mutants, small molecules inhibiting the kinase activity and anti-hIGF-IR antibodies) have been developed to inhibit the IGF-IR signaling pathway in tumor cells. One approach has been to target the kinase activity of IGF-IR with small molecule inhibitors. Two compounds were recently identified as small molecule kinase inhibitors capable of selectively inhibiting the IGF-IR. Garcia-Echeverria et al., *Cancer Cell* 5:231-239 (2004); Mitsiades et al., *Cancer Cell* 5:221-230 (2004). Inhibition of IGF-IR kinase activity abrogated IGF-I-mediated survival and colony formation in soft agar of MCF-7 human breast cancer cells. Garcia-Echeverria et al., *Cancer Cell* 5:231-239 (2004). When an IGF-IR kinase inhibitor was administered to mice bearing tumor xenografts, IGF-IR signaling in tumor xenografts was inhibited and the growth of IGF-IR-driven fibrosarcomas was significantly reduced. Garcia-Echeverria et al., *Cancer Cell* 5:231-239 (2004). A similar effect was observed on hematologic malignancies, especially multiple myeloma. In multiple myeloma cells, a small molecule IGF-IR kinase inhibitor demonstrated a >16-fold greater potency against the IGF-1R, as compared to the insulin receptor, and was similarly effective in inhibiting cell growth and survival. Mitsiades et al., *Cancer Cell* 5:221-230 (2004). The same compound was injected intraperitoneally into mice and inhibited multiple myeloma cell growth and enhanced survival of the mice. Mitsiades et al., *Cancer Cell* 5:221-230 (2004). When combined with other chemotherapeutics at subtherapeutic doses, inhibition of IGF-IR kinase activity synergistically reduced tumor burden. Mitsiades et al., *Cancer Cell* 5:221-230 (2004).

Another approach to inhibit IGF signaling has been the development of neutralizing antibodies directed against the receptor IGF-IR. Various groups have developed antibodies to IGF-IR that inhibit receptor IGF-I-stimulated autophosphorylation, induce receptor internalization and degradation, and reduce proliferation and survival of diverse human cancer cell lines. Hailey et al., *Mol Cancer Ther.* 1:1349-1353 (2002); Maloney et al., *Cancer Res.* 63:5073-5083 (2003); Benini et al., *Clin. Cancer Res.* 7:1790-1797 (2001); Burtrum et al., *Cancer Res.* 63:8912-8921 (2003). Additionally, in xenograft tumor models, IGF-IR blockade resulted in significant growth inhibition of breast, renal and pancreatic tumors in vivo. Burtrum et al., *Cancer Res.* 63:8912-8921 (2003); Maloney et al., *Cancer Res.* 63:5073-5083 (2003). Experiments utilizing chimeric humanized IGF-IR antibodies yielded similar results, inhibiting growth of breast cancer cells in vitro and in tumor xenografts. Sachdev et al., *Cancer Res.* 63:627-635 (2003). Other humanized IGF-IR antibodies blocked IGF-I-induced tyrosine phosphorylation and growth inhibition in breast and non small cell lung tumors, as well as in vivo. Cohen et al., *Clin. Cancer Res.* 11:2063-2073 (2005); Goetsch et al., *Int. J. Cancer* 113:316-328 (2005).

Increased IGF-I levels have also been associated with several non-cancerous pathological conditions, including acromegaly and gigantism (Barkan, Cleveland Clin. J. Med. 65: 343, 347-349, 1998), while abnormal IGF-I/IGF-II receptor function has been implicated in psoriasis (Wraight et al., Nat. Biotech. 18: 521-526, 2000), atherosclerosis and smooth muscle restenosis of blood vessels following angioplasty (Bayes-Genis et al., Circ. Res. 86: 125-130, 2000). Increased IGF-I levels have been implicated in diabetes or in complications associated with diabetes, such as microvascular proliferation (Smith et al., Nat. Med. 5: 1390-1395, 1999).

Antibodies to IGF-I and IGF-II have been disclosed in the art. See, for example, Goya et al., *Cancer Res.* 64:6252-6258 (2004); Miyamoto et al., *Clin. Cancer Res.* 11:3494-3502 (2005). Additionally, see WO 05/18671, WO 05/28515 and WO 03/93317.

SUMMARY

Embodiments of the invention relate to binding proteins that specifically bind to insulin-like growth factors and reduce tumor growth. In one embodiment, the binding proteins are fully human monoclonal antibodies, or binding fragments thereof that specifically bind to insulin-like growth factors and reduce tumor growth. Mechanisms by which this can be achieved can include and are not limited to either inhibition of binding of IGF-I/II to its receptor IGF-IR, inhibition of IGF-I/II-induced IGF-IR signaling, or increased clearance of IGF-I/II, therein reducing the effective concentration of IGF-I/II.

Thus, some embodiments provide a fully human isolated specific binding protein that preferentially binds to insulin-like growth factor-II (IGF-II) with cross-reactivity to insulin-like growth factor I (IGF-I) and neutralizes IGF-I and IGF-II activity. In certain aspects, the binding protein binds to IGF-II with at least 2.5 times greater affinity than to IGF-I. In other aspects, the binding protein binds to IGF-II with at least 3, at least 4, at least 5, at least 7, at least 10, at least 50, at least 60, at least 100 or at least 150 times greater affinity than to IGF-I.

In some embodiments, the specific binding protein has an $EC_{50}$ of no more than 15 nM for inhibiting IGF-I-dependent IGF-I receptor phosphorylation in NIH3T3 cells expressing IGF-IR ectopically. In some aspects, the specific binding protein has an $EC_{50}$ of no more than 15 nM, no more than 10 nM, or no more than 8 nM for inhibiting IGF-I-dependent IGF-I receptor phosphorylation in NIH3T3 cells expressing IGF-1R ectopically.

In some embodiments, the specific binding protein has an $EC_{50}$ of no more than 5 WM, no more than 4 nM, or no more than 3 nM for inhibiting IGF-II-dependent IGF-I receptor phosphorylation in NIH3T3 cells expressing IGF-1R ectopically.

In other embodiments, the specific binding protein inhibits greater than 70% of IGF-IL dependent proliferation of NIH3T3 cells that express recombinant hIGF-IR with an $EC_{50}$ of no more than 25 nM, no more than 20 nM, no more than 15 nM, or no more than 10 nM.

In other embodiments, the specific binding protein inhibits greater than 70% of IGF-I dependent proliferation of NIH3T3 cells that express recombinant hIGF-IR with an $EC_{50}$ of no more than 40 nM, no more than 30 nM, or no more than 25 nM.

In certain embodiments, the specific binding protein competes for binding with a monoclonal antibody comprising a variable heavy chain sequence selected from the group consisting of SEQ ID NO.: 2, SEQ ID NO.: 6, SEQ ID NO.: 10, SEQ ID NO.: 14 and SEQ ID NO.: 18, and comprising a variable light chain sequence selected from the group consisting of SEQ ID NO.: 4, SEQ ID NO.: 8, SEQ ID NO.: 12 and SEQ ID NO.: 16.

One embodiment of the invention is a fully human antibody that binds to IGF-I with a Kd less than 500 picomolar (pM). More preferably, the antibody binds with a Kd less than 450 picomolar (pM). More preferably, the antibody binds with a Kd less than 410 picomolar (pM). More preferably, the antibody binds with a $K_d$ of less than 350 pM. Even more preferably, the antibody binds with a $K_d$ of less than 300 pM. Affinity and/or avidity measurements can be measured by BIACORE®, as described herein.

Yet another embodiment of the invention is a fully human monoclonal antibody that binds to IGF-II with a $K_d$ of less than 175 picomolar (pM). More preferably, the antibody binds with a Kd less than 100 picomolar (pM). More preferably, the antibody binds with a Kd less than 50 picomolar (pM). More preferably, the antibody binds with a Kd less than 5 picomolar (pM). Even more preferably, the antibody binds with a $K_d$ of less than 2 pM.

In certain embodiments, the specific binding protein is a fully human monoclonal antibody or a binding fragment of a fully human monoclonal antibody. The binding fragments can include fragments such as Fab, Fab' or F(ab')$_2$ and Fv.

One embodiment of the invention comprises fully human monoclonal antibodies 7.251.3 (ATCC Accession Number PTA-7422), 7.34.1 (ATCC Accession Number PTA-7423) and 7.159.2 (ATCC Accession Number PTA-7424) which specifically bind to IGF-I/II, as discussed in more detail below. The hybridoma producing monoclonal antibody 7.159.2 was deposited on Mar. 7, 2006 at the American Type Culture Collection, 10801 University Boulevard, Manassas, Va. 20110-2209, U.S.A. and has been assigned a deposit number PTA-7424.

In some embodiments the specific binding protein that binds to insulin-like growth factor-II (IGF-II) with cross-reactivity to insulin-like growth factor-I (IGF-I), or binding fragment thereof can include a heavy chain polypeptide having the sequence of SEQ ID NO.: 6, and a light chain polypeptide having the sequence of SEQ ID NO.: 8.

The specific binding protein can include a heavy chain polypeptide having the sequence of SEQ ID NO.: 10, and a light chain polypeptide having the sequence of SEQ IDNO.: 12.

The specific binding protein of the invention can include heavy chain polypeptide having the sequence of SEQ ID NO.: 14 and a light chain polypeptide having the sequence of SEQ ID NO.: 16.

In certain embodiments, .the specific binding protein can be in a mixture with a pharmaceutically acceptable carrier.

Another embodiment includes isolated nucleic acid molecules encoding any of the specific binding proteins described herein, vectors having isolated nucleic acid molecules encoding the specific binding proteins, or a host cell transformed with any of such nucleic acid molecules and vectors.

In certain embodiments the specific binding protein that binds to insulin-like growth factor-II (IGF-II) with cross-reactivity to insulin-like growth factor-I (IGF-I), or binding fragment thereof does not bind specifically to IGF-II or IGF-I proteins when said proteins are bound to Insulin Growth Factor Binding Proteins.

Further embodiments include methods of determining the level of insulin-like growth factor-II (IGF-II) and insulin-like growth factor I (IGF-I) in a patient sample. These methods can include providing a patient sample; contacting the sample with a specific binding protein that binds to insulin-like growth factor-II (IGF-II) with cross-reactivity to insulin-like growth factor-I (IGF-I), or binding fragment thereof; and determining the level of IGF-I and IGF-II in said sample. In some aspects, the patient sample is blood.

Additional embodiments include methods of treating a malignant tumor in a mammal. These methods can include selecting a mammal in need of treatment for a malignant tumor; and administering to the mammal a therapeutically effective dose of a specific binding protein that binds to insulin-like growth factor-II (IGF-II) with cross-reactivity to insulin-like growth factor-I (IGF-I), or binding fragment thereof. In some aspects the animal is human. In some aspects the binding protein is a fully human monoclonal antibody, and is selected from the group consisting of mAb 7.251.3 (ATCC Accession Number PTA-7422), mAb 7.34.1 (ATCC Accession Number PTA-7423), and mAb 7.159.2 (ATCC Accession Number PTA-7424).

Treatable diseases can include melanoma, non-small cell lung cancer, glioma, hepatocellular (liver) carcinoma, thyroid tumor, gastric (stomach) cancer, prostrate cancer, breast cancer, ovarian cancer, bladder cancer, lung cancer, glioblastoma, endometrial cancer, kidney cancer, colon cancer, pancreatic cancer, and epidermoid carcinoma.

Additional embodiments include methods of treating a growth factor-dependent disease in a mammal. These methods include selecting a mammal in need of treatment for a growth factor-dependent disease; and administering to said mammal a therapeutically effective dose of a specific binding protein that binds to insulin-like growth factor-II (IGF-II) with cross-reactivity to insulin-like growth factor-I (IGF-I), or binding fragment thereof In some aspects, the mammal can be human. In some aspects the binding protein is a fully human monoclonal antibody, and is selected from the group consisting of mAb 7.251.3 (ATCC Accession Number PTA-7422), mAb 7.34.1 (ATCC Accession Number PTA-7423), and mAb 7.159.2 (ATCC Accession Number PTA-7424).

Treatable growth factor-dependent diseases can include osteoporosis, diabetes, and cardiovascular diseases. Other treatable disease conditions include acromegaly and gigantism, psoriasis, atherosclerosis and smooth muscle restenosis of blood vessels, as well as diabetes.

Additional embodiments include a conjugate comprising a fully human monoclonal antibody that binds to insulin-like growth factor-II (IGF-II) with cross-reactivity to insulin-like growth factor-I (IGF-I), or a binding fragment thereof and a therapeutic agent. In some aspects the therapeutic agent can be a toxin, a radioisotope, or a pharmaceutical composition.

In other embodiments, the invention provides fully human monoclonal antibodies, or binding fragment thereof, that bind to insulin-like growth factor-II (IGF-II) with cross-reactivity to insulin-like growth factor-I (IGF-I), and comprise a heavy chain complementarity determining region 1 (CDR1) having the amino acid sequence of "Ser Tyr Tyr Trp Ser" (SEQ ID NO: 21); a heavy chain complementarity determining region 2 (CDR2) having the amino acid sequence of "Tyr Phe Phe Tyr Ser Gly Tyr Thr Asn Tyr Asn Pro Ser Leu Lys Ser" (SEQ ID NO: 22); and a heavy chain complementarity determining region 3 (CDR3) having the amino acid sequence. of "Ile Thr Gly Thr Thr Lys Gly Gly Met Asp Val" (SEQ ID NO: 23).

Further embodiments include fully human monoclonal antibodies, or binding fragment thereof, having a light chain complementarity determining region 1 (CDR1) having the amino acid sequence of "Thr Gly Ser Ser Ser Asn Ile Gly Ala Gly Tyr Asp Val His" (SEQ ID NO: 24). Antibodies herein can also include a light chain complementarity determining region 2 (CDR2) having the amino acid sequence of "Gly Asn Asn Asn Arg Pro Ser" (SEQ ID NO: 25); and a light chain complementarity determining region 3 (CDR3) having the amino acid sequence of "Gln Ser Phe Asp Ser Ser Leu Ser Gly Ser Val" (SEQ ID NO: 26).

In other embodiments, the invention provides fully human monoclonal antibodies, or binding fragment thereof, that bind to insulin-like growth factor-II (IGF-II) with cross-reactivity to insulin-like growth factor-I (IGF-I), and comprise a heavy chain complementarity determining region 1 (CDR1) having the amino acid sequence of "Ser Tyr Tyr Trp Ser" (SEQ ID NO: 27); a heavy chain complementarity determining region 2 (CDR2) having the amino acid sequence of "Tyr Phe Phe Tyr Ser Gly Tyr Thr Asn Tyr Asn Pro Ser Leu Lys Ser" (SEQ ID NO: 28); and a heavy chain complementarity determining region 3 (CDR3) having the amino acid sequence of "Ile Thr Gly Thr Thr Lys Gly Gly Met Asp Val" (SEQ ID NO: 29).

Further embodiments include fully human monoclonal antibodies, or binding fragment thereof, having a light chain complementarity determining region 1 (CDR1) having the amino acid sequence of "Thr Gly Arg Ser Ser Asn Ile Gly Ala Gly Tyr Asp Val His" (SEQ ID NO: 30); a light chain complementarity determining region 2 (CDR2) having the amino acid sequence of "Gly Asn Ser Asn Arg Pro Ser" (SEQ ID NO: 31); and a light chain complementarity determining region 3 (CDR3) having the amino acid sequence of "Gln Ser Tyr Asp Ser Ser Leu Ser Gly Ser Val" (SEQ ID NO: 32).

In other embodiments, the invention provides fully human monoclonal antibodies, or binding fragment thereof, that bind to insulin-like growth factor-II (IGF-II) with cross-reactivity to insulin-like growth factor-I (IGF-I), and comprise a heavy chain complementarity determining region 1 (CDR1) having the amino acid sequence of "Ser Tyr Asp Ile Asn" (SEQ ID NO: 33); a heavy chain complementarity determining region 2 (CDR2) having the amino acid sequence of "Trp Met Asn Pro Asn Ser Gly Asn Thr Gly Tyr Ala Gln Lys Phe Gln Gly" (SEQ ID NO: 34); and a heavy chain complementarity determining region 3 (CDR3) having the amino acid sequence of "Asp Pro Tyr Tyr Tyr Tyr Tyr Gly Met Asp Val" (SEQ ID NO: 35).

Further embodiments include fully human monoclonal antibodies, or binding fragment thereof, having a light chain complementarity determining region 1 (CDR1) having the amino acid sequence of "Ser Gly Ser Ser Ser Asn Ile Glu Asn Asn His Val Ser" (SEQ ID NO: 36); a light chain complementarity determining region 2 (CDR2) having the amino acid sequence of "Asp Asn Asn Lys Arg Pro Ser" (SEQ ID NO: 37); and a light chain complementarity determining region 3 (CDR3) having the amino acid sequence of "Glu Thr Trp Asp Thr Ser Leu Ser Ala Gly Arg Val" (SEQ ID NO: 38).

In other embodiments, the invention provides fully human monoclonal antibodies, or binding fragment thereof, that bind to insulin-like growth factor-II (IGF-II) with cross-reactivity to insulin-like growth factor-I (IGF-I), and comprise a heavy chain complementarity determining region I (CDR1) having the amino acid sequence of "Ser Ser Ser Tyr Tyr Trp Gly" (SEQ ID NO: 81); a heavy chain complementarity determining region 2 (CDR2) having the amino acid sequence of "Gly Ile Tyr Tyr Ser Gly Ser Thr Tyr Tyr Asn Pro Ser Leu Lys Ser" (SEQ ID NO: 82); and a heavy chain complementarity determining region 3 (CDR3) having the amino acid sequence of "Gln Arg Gly His Ser Ser Gly Trp Trp Tyr Phe Asp Leu" (SEQ ID NO: 83).

Further embodiments include fully human monoclonal antibodies, or binding fragment thereof, having a light chain complementarity determining region 1 (CDR1) having the amino acid sequence of "Arg Ala Ser Gln Gly Ile Ser Ser Tyr Leu Ala" (SEQ ID NO: 84); a light chain complementarity determining region 2 (CDR2) having the amino acid sequence of "Ala Ala Ser Ser Leu Gln Ser" (SEQ ID NO: 85); and a light chain complementarity determining region 3 (CDR3) having the amino acid sequence of "Gln Gln Ala Asn Asn Phe Pro Phe Thr" (SEQ ID NO: 86).

In other embodiments, the invention provides fully human monoclonal antibodies, or binding fragment thereof, that bind to insulin-like growth factor-II (IGF-II) with cross-reactivity to insulin-like growth factor-I (IGF-I), and comprise a heavy chain complementarity determining region 1 (CDR1) having the amino acid sequence of "Ser Ser Ser Asn Tyr Trp Gly" (SEQ ID NO: 87); a heavy chain complementarity determining region 2 (CDR2) having the amino acid sequence of "Gly Ile Tyr Tyr Ser Gly Ser Thr Tyr Tyr Asn Pro Ser Leu Arg Ser" (SEQ ID NO: 88); and a heavy chain complementarity determining region 3 (CDR3) having the amino acid sequence of "Gln Arg Gly His Ser Ser Gly Trp Trp Tyr Phe Asp Leu" (SEQ ID NO: 89).

Further embodiments include fully human monoclonal antibodies, or binding fragment thereof, having a light chain complementarity determining region 1 (CDR1) having the amino acid sequence of "Arg Ala Ser Arg Gly Ile Ser Ser Trp Leu Ala" (SEQ ID NO: 90); a light chain complementarity determining region 2 (CDR2) having the amino acid sequence of "Thr Ala Ser Ser Leu Gln Ser" (SEQ ID NO: 91); and a light chain complementarity determining region 3 (CDR3) having the amino acid sequence of "Gln Gln Ala Asn Ser Phe Pro Phe Thr" (SEQ ID NO: 92).

Some embodiments provide the use of the specific binding proteins described herein in the preparation of a medicament for the treatment of a malignant tumor. In some aspects, the specific binding protein can be a fully human monoclonal antibody. In certain aspects, the binding protein is mAb 7.251.3 (ATCC Accession Number PTA-7422) or mAb 7.34.1 (ATCC Accession Number PTA-7423) or mAb 7.159.2 (ATCC Accession Number PTA-7424). In some aspects, the medicament is for use in combination with a second anti-neoplastic agent selected from the group consisting of an antibody, a chemotherapeutic agent, and a radioactive drug. In some aspects, the medicament is for use in conjunction with or following a conventional surgery, a bone marrow stem cell transplantation or a peripheral stem cell transplantation.

The malignant tumor can be melanoma, non-small cell lung cancer, glioma, hepatocellular (liver) carcinoma, thyroid tumor, gastric (stomach) cancer, prostrate cancer, breast cancer, ovarian cancer, bladder cancer, lung cancer, glioblastoma, endometrial cancer, kidney cancer, colon cancer, pancreatic cancer, and epidermoid carcinoma, for example.

Other embodiments provide the use of the specific binding proteins described herein in the preparation of a medicament for the treatment of a growth factor-dependent disease. In some aspects, the specific binding protein is a fully human monoclonal antibody and can be selected from the group consisting of mAb 7.251.3 (ATCC Accession Number PTA-7422), mAb 7.34.1 (ATCC Accession Number PTA-7423), and mAb 7.159.2 (ATCC Accession Number PTA-7424).

The growth factor-dependent disease can be osteoporosis, diabetes, and cardiovascular diseases, for example.

Preferably, the antibody comprises a heavy chain amino acid sequence having a complementarity determining region (CDR) with one or more of the sequences shown in Table 11. For example, the antibody can comprise a heavy chain amino acid sequence having the CDR1, CDR2, or CDR3 of one or more of the sequences shown in Table 11, or a combination thereof It is noted that those of ordinary skill in the art can readily accomplish CDR determinations. See for example, Kabat et al., *Sequences of Proteins of Immunological Interest*, Fifth Edition, NIH Publication 91-3242, Bethesda Md. (1991), vols. 1-3.

Embodiments of the invention described herein relate to monoclonal antibodies that bind IGF-I/II and affect IGF-I/II function. Other embodiments relate to fully human anti-IGF-I/II antibodies and anti-IGF-I/II antibody preparations with desirable properties from a therapeutic perspective, including high binding affinity for IGF-I/II, the ability to neutralize IGF-I/II in vitro and in vivo, and the ability to inhibit IGF-I/II induced cell proliferation.

DETAILED DESCRIPTION

Figure 1:
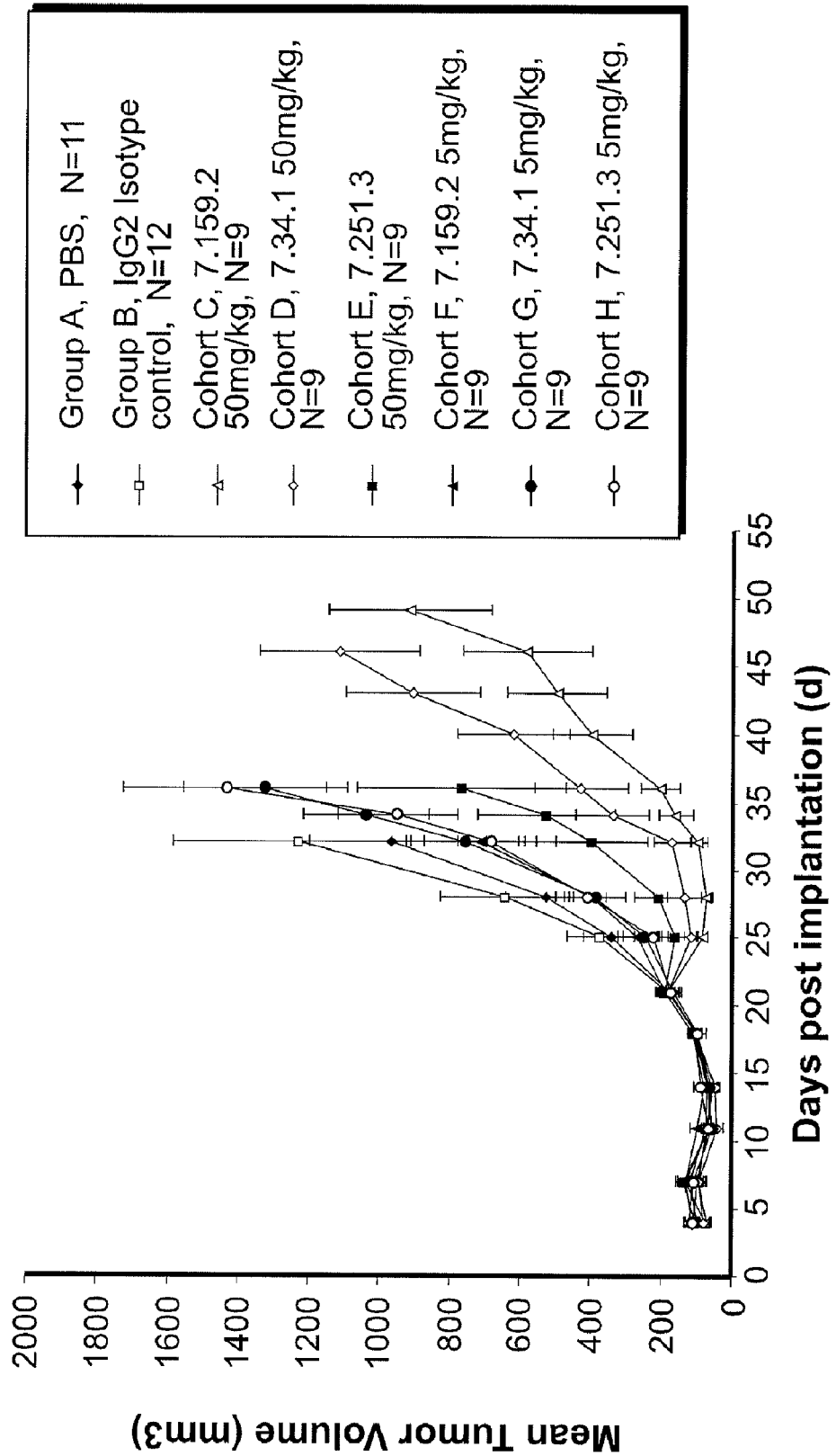
FIG. 1 is a graph showing inhibition of xenograft tumor growth in nude mice of NIH3T3 cells expressing IGF-II and IGF-IR (Clone 32 cells) with mAbs 7.159.2, 7.34.1, 7.251.3 compared to IgG2 and PBS controls. Mean tumor volume is shown on the y-axis and time after implantation is shown on the x-axis.

Embodiments of the invention described herein relate to binding proteins that specifically bind to IGF-II with cross reactivity to IGF-I (referred to herein as "IGFI/II"). In some embodiments, the binding proteins are antibodies, or binding fragments thereof, and bind to IGF-II with cross-reactivity to IGF-I and inhibit the binding of these proteins to their receptor, IGF-IR. Other embodiments of the invention include fully human neutralizing anti-IGF-I/II antibodies, and antibody preparations that are therapeutically useful and bind both insulin-like growth factors. Such anti-IGF-I/II antibody preparations preferably have desirable therapeutic properties, including strong binding affinity for IGF-I/II, the ability to neutralize IGF-I/II in vitro, and the ability to inhibit IGF-I/II-induced cell proliferation in vivo.

Embodiments of the invention also include isolated binding fragments of anti-IGF-/II antibodies. Preferably, the binding fragments are derived from fully human anti-IGF-I/II antibodies. Exemplary fragments include Fv, Fab' or other well know antibody fragments, as described in more detail below. Embodiments of the invention also include cells that express fully human antibodies against IGF-I/II. Examples of cells include hybridomas, or recombinantly created cells, such as Chinese hamster ovary (CHO) cells that produce antibodies against IGF-I/II.

In addition, embodiments of the invention include methods of using these antibodies for treating diseases. Anti-IGF-I/II antibodies are useful for preventing IGF-I/II mediated IGF-I/II signal transduction, thereby inhibiting cell proliferation. The mechanism of action of this inhibition may include inhibition of IGF-I/II from binding to its receptor, IGF-IR, inhibition of IGF-I/II induced IGF-IR signaling, or enhanced clearance of IGF-I/II therein lowering the effective concentration of IGF-I/II for binding to IGF-IR. Diseases that are treatable through this inhibition mechanism include, but are not limited to, neoplastic diseases, such as, melanoma, non-small cell lung cancer, glioma, hepatocellular (liver) carcinoma, gynecologic tumors, head and neck cancer, esophageal cancer, glioblastoma, and cancers and tumors of the thyroid, stomach, prostrate, breast, ovary, bladder, lung, uterus, kidney, colon, and pancreas, salivary gland, and colorectum.

Other embodiments of the invention include diagnostic assays for specifically determining the quantity of IGF-I/II in a biological sample. The assay kit can include anti-IGF-I/II antibodies along with the necessary labels for detecting such antibodies. These diagnostic assays are useful to screen for growth factor-related diseases including, but not limited to, neoplastic diseases, such as, melanoma, non-small cell lung cancer, glioma, hepatocellular (liver) carcinoma, gynecologic tumors, head and neck cancer, esophageal cancer, glioblastoma, and carcinoma of the thyroid, stomach, prostrate, breast, ovary, bladder, lung, uterus, kidney, colon, and pancreas, salivary gland, and colorectum. Other non-neoplastic disease conditions may include acromegaly and gigantism, psoriasis, osteoporosis, atherosclerosis and smooth muscle restenosis of blood vessels, as well as diabetes.

Further embodiments, features, and the like regarding anti-IGF-I/II antibodies are provided in additional detail below.

Sequence Listing

Embodiments of the invention include the specific anti-IGF-I/II antibodies listed below in Table 1. This table reports the identification number of each anti-IGF-I/II antibody, along with the SEQ ID number of the corresponding heavy chain and light chain genes. Further, the germline sequences from which each heavy chain and light chain derive are also provided below in Table 1.

Each antibody has been given an identification number that includes either two or three numbers separated by one or two decimal points. In some cases, several clones of one antibody were prepared. Although the clones have the identical nucleic acid and amino acid sequences as the parent sequence, they may also be listed separately, with the clone number indicated by the number to the right of a second decimal point. Thus, for example, the nucleic acid and amino acid sequences of antibody 7.159.2 are identical to the sequences of antibody 7.159.1.

As can be seen by comparing the sequences in the sequence listing, SEQ ID NOs.: 1-20 differ from SEQ ID NOs.: 39-58 because SEQ ID NOs.: 39-58 include the untranslated, signal peptide, and constant domain regions for each sequenced heavy or light chain.

TABLE 1

| mAb ID No.: | Sequence | SEQ ID NO: |
|---|---|---|
| 7.158.1 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |
| 7.159.2 | Nucleotide sequence encoding the variable region of the heavy chain | 5 |
| | Amino acid sequence encoding the variable region of the heavy chain | 6 |
| | Nucleotide sequence encoding the variable region of the light chain | 7 |
| | Amino acid sequence encoding the variable region of the light chain | 8 |
| 7.34.1 | Nucleotide sequence encoding the variable region of the heavy chain | 9 |
| | Amino acid sequence encoding the variable region of the heavy chain | 10 |
| | Nucleotide sequence encoding the variable region of the light chain | 11 |
| | Amino acid sequence encoding the variable region of the light chain | 12 |
| 7.251.3 | Nucleotide sequence encoding the variable region of the heavy chain | 13 |
| | Amino acid sequence encoding the variable region of the heavy chain | 14 |
| | Nucleotide sequence encoding the variable region of the light chain | 15 |
| | Amino acid sequence encoding the variable region of the light chain | 16 |
| 7.234.1 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 7.158.1 | Nucleotide sequence encoding the variable region of the heavy chain | 39 |
| | Amino acid sequence encoding the variable region of the heavy chain | 40 |
| | Nucleotide sequence encoding the variable region of the light chain | 41 |
| | Amino acid sequence encoding the variable region of the light chain | 42 |
| 7.159.2 | Nucleotide sequence encoding the variable region of the heavy chain | 43 |
| | Amino acid sequence encoding the variable region of the heavy chain | 44 |
| | Nucleotide sequence encoding the variable region of the light chain | 45 |
| | Amino acid sequence encoding the variable region of the light chain | 46 |
| 7.34.1 | Nucleotide sequence encoding the variable region of the heavy chain | 47 |
| | Amino acid sequence encoding the variable region of the heavy chain | 48 |
| | Nucleotide sequence encoding the variable region of the light chain | 49 |
| | Amino acid sequence encoding the variable region of the light chain | 50 |
| 7.251.3 | Nucleotide sequence encoding the variable region of the heavy chain | 51 |
| | Amino acid sequence encoding the variable region of the heavy chain | 52 |
| | Nucleotide sequence encoding the variable region of the light chain | 53 |
| | Amino acid sequence encoding the variable region of the light chain | 54 |
| 7.234.1 | Nucleotide sequence encoding the variable region of the heavy chain | 55 |
| | Amino acid sequence encoding the variable region of the heavy chain | 56 |
| | Nucleotide sequence encoding the variable region of the light chain | 57 |
| | Amino acid sequence encoding the variable region of the light chain | 58 |
| Germline (7.158.1) | Nucleotide sequence encoding the variable region of the heavy chain | 59 |
| | Amino acid sequence encoding the variable region of the heavy chain | 60 |
| | Nucleotide sequence encoding the variable region of the light chain | 61 |
| | Amino acid sequence encoding the variable region of the light chain | 62 |
| Germline (7.159.1) | Nucleotide sequence encoding the variable region of the heavy chain | 63 |
| | Amino acid sequence encoding the variable region of the heavy chain | 64 |
| | Nucleotide sequence encoding the variable region of the light chain | 65 |
| | Amino acid sequence encoding the variable region of the light chain | 66 |
| Germline (7.34.1) | Nucleotide sequence encoding the variable region of the heavy chain | 67 |
| | Amino acid sequence encoding the variable region of the heavy chain | 68 |
| | Nucleotide sequence encoding the variable region of the light chain | 69 |
| | Amino acid sequence encoding the variable region of the light chain | 70 |
| Germline (7.251.3) | Nucleotide sequence encoding the variable region of the heavy chain | 71 |
| | Amino acid sequence encoding the variable region of the heavy chain | 72 |
| | Nucleotide sequence encoding the variable region of the light chain | 73 |
| | Amino acid sequence encoding the variable region of the light chain | 74 |

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "IGF-I" refers to the molecule Insulin-like growth factor-I, and the term "IGF-II" refers to the molecule Insulin-like growth factor-II. The term "IGF-I/II" refers to both molecules Insulin-like growth factors-I and -II, and relates to the preferential binding to IGF-II with cross-reactivity to IGF-I. Thus, an antibody that binds to IGF-I/II will preferentially bind to IGF-II, but would cross-react with IGF-I, binding to IGF-II with higher affinity than to IGF-I. For example, the antibody can bind to IGF-II with 2.5 times greater affinity than to IGF-I. In certain embodiments, the antibody can bind to IGF-II with at least 5, at least 10, at least 25, at least 50 or at least 150 times greater affinity than to IGF-I.

The term "neutralizing" when referring to an antibody relates to the ability of an antibody to eliminate, or significantly reduce, the activity of a target antigen. Accordingly, a "neutralizing" anti-IGF-I/II antibody is capable of eliminating or significantly reducing the activity of IGF-I/II. A neutralizing IGF-I/II antibody may, for example, act by blocking the binding of IGF-I/II to its receptor IGF-IR. By blocking this binding, the IGF-IR mediated signal transduction is significantly, or completely, eliminated. Ideally, a neutralizing antibody against IGF-I/II inhibits cell proliferation.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M.O., in *Atlas of Protein Sequence and Structure*, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison. A reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least about 18 contiguous nucleotide positions or about 6 amino acids wherein the polynucleotide sequence or amino acid sequence is compared to a reference sequence of at least 18 contiguous nucleotides or 6 amino acid sequences and wherein the portion of the polynucleotide sequence in the comparison window may include additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), GENEWORKS™, or MACVECTOR® software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence.identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W. H. Freeman and Company, New York (1984)); Introduction to Protein Structure (C. Branden and J. Tooze, eds., Garland Publishing, New York, N.Y. (1991)); and Thornton et at. *Nature* 354:105 (1991), which are each incorporated herein by reference.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to IGF-I/II, under suitable binding conditions, (2) ability to block appropriate IGF-I/II binding, or (3) ability to inhibit IGF-I/II activity. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15:29 (1986); Veber and Freidinger *TINS* p.392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —$CH=CH$— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

As used herein, the term "antibody" refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site.

"Binding fragments" of an antibody are produced by recombinant DNA techniques, or by enzymatic or chemical cleavage of intact antibodies. Binding fragments include Fab, Fab', F(ab')$_2$, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counterreceptor by at least about 20%, 40%, 60% or 80%, and more usually greater than about 85% (as measured in an in vitro competitive binding assay).

As used herein, a "binding protein" or a "specific binding protein" are proteins that specifically bind to a target molecule. Antibodies, and binding fragments of antibodies, are binding proteins.

The term "epitope" includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leq 1$ μM, preferably $\leq 100$ nM and most preferably $\leq 10$ nM.

The term "agent" is used herein to denote a chemical compound, a mixture of chemical compounds, a biological macromolecule, or an extract made from biological materials.

"Active" or "activity" in regard to an IGF-I/II polypeptide refers to a portion of an IGF-I/II polypeptide that has a biological or an immunological activity of a native IGF-I/II polypeptide. "Biological" when used herein refers to a biological function that results from the activity of the native IGF-I/II polypeptide. A preferred IGF-I/II biological activity includes, for example, IGF-I/II induced cell proliferation.

"Mammal" when used herein refers to any animal that is considered a mammal. Preferably, the mammal is human.

Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in the a F(ab')$_2$ fragment in which the two arms of the antibody molecule remain linked and comprise two-antigen binding sites. The F(ab')$_2$ fragment has the ability to crosslink antigen.

"Fv" when used herein refers to the minimum fragment of an antibody that retains both antigen-recognition and antigen-binding sites.

"Fab" when used herein refers to a fragment of an antibody that comprises the constant domain of the light chain and the CH1 domain of the heavy chain.

The term "mAb" refers to monoclonal antibody.

"Liposome" when used herein refers to a small vesicle that may be useful for delivery of drugs that may include the IGF-I/II polypeptide of the invention or antibodies to such an IGF-I/II polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include $^{3}$H, $^{14}$C, $^{15}$N, $^{35}$S, $^{90}$Y, $^{99}$Tc, $^{111}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" includes human and veterinary subjects.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal procedures fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. *Nature Genetics* 15:146-156 (1997) and Green and Jakobovits *J. Exp. Med.* 188:483-495 (1998). The XenoMouse® (strains of mice that have been engineered to contain up to but less than 1000 kb-sized germline configured fragments of the human heavy chain locus and kappa light chain locus) strains are available from Abgenix, Inc. (Fremont, Calif.).

The production of the XenoMouse® (strains of mice that have been engineered to contain up to but less than 1000 kb-sized germline configured fragments of the human heavy chain locus and kappa light chain locus) strains of mice is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, filed Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, Ser. No. 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023,010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KM™—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

Preparation of Antibodies

Antibodies, as described herein, were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. *Nature Genetics* 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. IGF-I/II), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to IGF-I/II. Further, provided herein are characterization of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the IGF-I/II immunogen. The supernatants might also be screened for immunoreactivity against fragments of IGF-I/II to further map the different antibodies for binding to domains of functional interest on IGF-I/II. The antibodies may also be screened against other related human chemokines and against the rat, the mouse, and non-human primate, such as cynomolgus monkey, orthologues of IGF-I/II, the last to determine species cross-reactivity. B cells from wells containing antibodies of interest may be immortalized by various methods including fusion to make hybridomas either from individual or from pooled wells, or by infection with EBV or transfection by known immortalizing genes and then plating in suitable medium. Alternatively, single plasma cells secreting antibodies with the desired specificities are then isolated using an IGF-I/II-specific hemolytic plaque assay (Babcook et al., *Proc. Natl. Acad. Sci. USA* 93:7843-48 (1996)). Cells targeted for lysis are preferably sheep red blood cells (SRBCs) coated with the IGF-I/II antigen.

In the presence of a B-cell culture containing plasma cells secreting the immunoglobulin of interest and complement, the formation of a plaque indicates specific IGF-I/II-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

In general, antibodies produced by the fused hybridomas were human IgG2 heavy chains with fully human kappa or lambda light chains. Antibodies described herein possess human IgG4 heavy chains as well as IgG2 heavy chains. Antibodies can also be of other human isotypes, including IgG1. The antibodies possessed high affinities, typically possessing a Kd of from about $10^{-6}$ through about $10^{-12}$ M or below, when measured by solid phase and solution phase techniques. Antibodies possessing a KD of at least $10^{-11}$ M are preferred to inhibit the activity of IGF-I/II.

As will be appreciated, anti-IGF-I/II antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive IGF-I/II binding properties.

Anti-IGF-I/II antibodies are useful in the detection of IGF-I/II in patient samples and accordingly are useful as diagnostics for disease states as described herein. In addition, based on their ability to significantly neutralize IGF-I/II activity (as demonstrated in the Examples below), anti-IGF-I/II antibodies have therapeutic effects in treating symptoms and conditions resulting from IGF-I/II expression. In specific embodiments, the antibodies and methods herein relate to the treatment of symptoms resulting from IGF-I/II induced cell proliferation. Further embodiments involve using the antibodies and methods described herein to treat diseases including neoplastic diseases, such as, melanoma, non-small cell lung cancer, glioma, hepatocellular (liver) carcinoma, thyroid tumor, gastric (stomach) cancer, prostrate cancer, breast cancer, ovarian cancer, bladder cancer, lung cancer, glioblastoma, endometrial cancer, kidney cancer, colon cancer, gynecologic tumors, head and neck cancer, esophageal cancer, and pancreatic cancer. Other non-neoplastic disease conditions may include acromegaly and gigantism, psoriasis, osteoporosis, atherosclerosis and smooth muscle restenosis of blood vessels, as well as diabetes.

Therapeutic Administration and Formulations

Embodiments of the invention include sterile pharmaceutical formulations of anti-IGF-I/II antibodies that are useful as treatments for diseases. Such formulations would inhibit the binding of IGF-I/II to its receptor IGF-IR, thereby effectively treating pathological conditions where, for example, serum or tissue IGF-I/II is abnormally elevated. Anti-IGF-I/II antibodies preferably possess adequate affinity to potently neutralize IGF-I/II, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in *Remington: The Science and Practice of Pharmacy* (20$^{th}$ ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., *J. Biomed Mater. Res.*, (1981) 15:167-277 and Langer, *Chem. Tech.*, (1982) 12:98-105, or poly(vinylalcohol)), polylactides (U.S. Pat. No. 3,773,919, EP 58,481), copolymers of L-glutamic acid and gamma ethyl-L-glutamate (Sidman et al., *Biopolymers*, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitoneally can produce a sustained release effect. Other compositions also include liposomally entrapped antibodies. Liposomes containing such antibodies are prepared by methods known per se: U.S. Pat. No. DE 3,218,121; Epstein et al., *Proc. Natl. Acad Sci. USA*, (1985) 82:3688-3692; Hwang et al., *Proc. Natl. Acad. Sci. USA*, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." *Regul. Toxicol. Pharmacol.* 32(2): 210-8 (2000), Wang W. "Lyophilization and development of solid protein pharmaceuticals." *Int. J. Pharm.* 203(1-2): 1-60 (2000), Charman WN "Lipids, lipophilic drugs, and oral drug delivery-some emerging concepts." *J. Pharm Sci.* 89(8):967-78 (2000), Powell et al. "Compendium of excipients for parenteral formulations" *PDA J Pharm Sci Technol.* 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to IGF-I/II, the design of other therapeutic modalities is facilitated and disclosed to one of skill in the art. Such modalities include, without limitation, advanced antibody therapeutics, such as bispecific antibodies, immunotoxins, radiolabeled therapeutics, and single antibody V domains, antibody-like binding agent based on other than V region scaffolds, generation of peptide therapeutics, gene therapies, particularly intrabodies, antisense therapeutics, and small molecules.

In connection with the generation of advanced antibody therapeutics, where complement fixation is a desirable attribute, it can be possible to sidestep the dependence on complement for cell killing through the use of bispecifics, immunotoxins, or radiolabels, for example.

For example, bispecific antibodies can be generated that comprise (i) two antibodies, one with a specificity to IGF-I/II and another to a second molecule, that are conjugated together, (ii) a single antibody that has one chain specific to IGF-I/II and a second chain specific to a second molecule, or (iii) a single chain antibody that has specificity to both IGF-I/II and the other molecule. Such bispecific antibodies can be generated using techniques that are well known; for example, in connection with (i) and (ii) see e.g., Fanger et al. *Immunol Methods* 4:72-81 (1994) and Wright and Harris, supra. and in connection with (iii) see e.g., Traunecker et al. *Int. J. Cancer (Suppl.)* 7:51-52 (1992). In each case, the second specificity can be made as desired. For example, the second specificity can be made to the heavy chain activation receptors, including, without limitation, CD16 or CD64 (see e.g., Deo et al. 18:127 (1997)) or CD89 (see e.g., Valerius et al. *Blood* 90:4485-4492 (1997)).

Antibodies can also be modified to act as immunotoxins utilizing techniques that are well known in the art. See e.g., Vitetta *Immunol Today* 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in *Cancer Chemotherapy and Biotherapy* 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing the desired multimeric enzyme subunit oligomerization domain. In some embodiments, a pharmaceutical composition comprising an effective amount of the antibody in association with a pharmaceutically acceptable carrier or diluent is provided.

In some embodiments, an anti-IGF-I/II antibody is linked to an agent (e.g., radioisotope, pharmaceutical composition, or a toxin). Preferably, such antibodies can be used for the treatment of diseases, such diseases can relate to cells expressing IGF-I/II or cells overexpressing IGF-I/II. For example, it is contemplated that the drug possesses the pharmaceutical property selected from the group of antimitotic, alkylating, antimetabolite, antiangiogenic, apoptotic, alkaloid, COX-2, and antibiotic agents and combinations thereof The drug can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof.

Examples of toxins further include gelonin, Pseudomonas exotoxin (PE), PE40, PE38, diphtheria toxin, ricin, ricin, abrin, alpha toxin, saporin, ribonuclease (RNase), DNase I, Staphylococcal enterotoxin-A, pokeweed antiviral protein, gelonin, Pseudomonas endotoxin, as well as derivatives, combinations and modifications thereof Examples of radioisotopes include gamma-emitters, positron-emitters, and x-ray emitters that can be used for localization aznd/or therapy, and beta-emitters and alpha-emitters that can be used for therapy. The radioisotopes described previously as useful for diagnostics, prognostics and staging are also useful for therapeutics. Non-limiting examples of anti-cancer or anti-leukemia agents include anthracyclines such as doxorubicin (adriamycin), daunorubicin (daunomycin), idarubicin, detorubicin, carminomycin, epirubicin, esorubicin, and morpholino and substituted derivatives, combinations and modifications thereof. Exemplary pharmaceutical agents include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof Preferably, the anti-cancer or anti-leukemia is doxorubicin, morpholinodoxorubicin, or morpholinodaunorubicin.

As will be appreciated by one of skill in the art, in the above embodiments, while affinity values can be important, other factors can be as important or more so, depending upon the particular function of the antibody. For example, for an immunotoxin (toxin associated with an antibody), the act of binding of the antibody to the target can be useful; however, in some embodiments, it is the internalization of the toxin into the cell that is the desired end result. As such, antibodies with a high percent internalization can be desirable in these situations. Thus, in one embodiment, antibodies with a high efficiency in internalization are contemplated. A high efficiency of internalization can be measured as a percent internalized antibody, and can be from a low value to 100%. For example, in varying embodiments, 0.1-5, 5-10, 10-20, 20-30, 30-40, 40-45, 45-50, 50-60, 60-70, 70-80, 80-90, 90-99, and 99-100% can be a high efficiency. As will be appreciated by one of skill in the art, the desirable efficiency can be different in different embodiments, depending upon, for example, the associated agent, the amount of antibody that can be administered to an area, the side effects of the antibody-agent complex, the type (e.g., cancer type) and severity of the problem to be treated.

In other embodiments, the antibodies disclosed herein provide an assay kit for the detection of IGF-I/II expression in mammalian tissues or cells in order to screen for a disease or disorder associated with changes in expression of IGF-I/II. The kit comprises an antibody that binds IGF-I/II and means for indicating the reaction of the antibody with the antigen, if present.

In some embodiments, an article of manufacture is provided comprising a container, comprising a composition containing an anti-IGF-I/II antibody, and a package insert or label indicating that the composition can be used to treat disease mediated by IGF-I/II expression. Preferably a mammal, and more preferably, a human, receives the anti-IGF-I/II antibody.

Combinations

The anti-IGF-I/II antibodies defined hereinbefore may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, MEK inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function, angiostatin and inhibitors of the action of angiopoietins e.g angiopoietin 1 and angiopoietin 2);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(x) cell cycle inhibitors including for example CDK inhibitors (eg flavopiridol) and other inhibitors of cell cycle checkpoints (eg checkpoint kinase); inhibitors of aurora kinase and other kinases involved in mitosis and cytdkinesis regulation (eg mitotic kinesins); and histone deacetylase inhibitors;

(xi) endothelin antagonists, including endothelin A antagonists, endothelin B antagonists and endothelin A and B antagonists; for example ZD4054 and ZD1611 (WO 96 40681), atrasentan and YM598; and (xii) biotherapeutic therapeutic approaches for example those which use peptides or proteins (such as antibodies or soluble external receptor domain constructions) which either sequest receptor ligands, block ligand binding to receptor or decrease receptor signalling (e.g. due to enhanced receptor degradation or lowered expression levels)

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

EXAMPLES

The following examples, including the experiments conducted and results achieved are provided for illustrative purposes only and are not to be construed as limiting upon the teachings herein.

Example 1

Immunization and TITERING

Immunization

Recombinant human IGF-I and IGF-II obtained from R&D Systems, Inc. (Minneapolis, Minn. Cat. No. 291-G1 and 292-G2 respectively) were used as antigens. Monoclonal antibodies against IGF-I/II were developed by sequentially immunizing XenoMouse® (strains of mice that have been engineered to contain up to but less than 1000 kb-sized germline configured fragments of the human heavy chain locus and kappa light chain locus) mice (XenoMouse® strains XMG2 and XMG4 (3C-1 strain), Abgenix, Inc. Fremont, Calif.). XenoMouse animals were immunized via footpad route for all injections. The total volume of each injection was 50 µl per mouse, 25 µl per footpad. A total of ten (10) mice were immunized in each group. Each injection was with 10 µg per mouse of IGF-I or IGF-II alone or conjugated to Keyhole Limpet Hemocyanin (KLH) antigen as a carrier, as detailed in Table 2. The first injection was made up in Dulbecco's PBS (DPBS) and admixed 1:1 v/v with Titermax Gold Adjuvant (SIGMA Cat. #T2684, lot #K1599). A total of 8 to 11 additional boosts were then administered over a period of 27 to 38 days, admixed with 25 µg of Adju-Phos (aluminum phosphate gel, Catalog # 1452-250, batch #8937, HCl Biosector) and 10 µg CpG (15 µl of ImmunEasy Mouse Adjuvant, catalog # 303101; lot #11553042; Qiagen) per mouse, followed by a final boost of 10 µg of antigen in pyrogen-free DPBS, without adjuvant. For combined immunization (animals immunized with both IGF-I and IGF-II), the second antigen was given in the last two (2) boosts.

TABLE 2

IMMUNIZATION SUMMARY

| Immu-nization Group | Initial Immunogen | Final Immunogen | KLH Conjugated | Isotype of Mice | Fusion Group |
|---|---|---|---|---|---|
| 1 | IGF-1 | IGF-1 | − | IgG2-κλ | 1 |
| 3 | IGF-1 | IGF-1 | − | IgG4-κλ | 1 |
| 5 | IGF-1 | IGF-1 | + | IgG2-κλ | 1 |
| 7 | IGF-1 | IGF-1 | + | IgG4-κλ | 1 |
| 2 | IGF-2 | IGF-2 | − | IgG2-κλ | 2 |
| 4 | IGF-2 | IGF-2 | − | IgG4-κλ | 2 |
| 6 | IGF-2 | IGF-2 | + | IgG2-κλ | 2 |
| 8 | IGF-2 | IGF-2 | + | IgG4-κλ | 2 |
| 9 | IGF-1 | IGF-2 | − | IgG2-κλ | 3 |
| 11 | IGF-1 | IGF-2 | − | IgG4-κλ | 3 |
| 13 | IGF-1 | IGF-2 | + | IgG2-κλ | 3 |
| 15 | IGF-1 | IGF-2 | + | IgG4-κλ | 3 |
| 10 | IGF-2 | IGF-1 | − | IgG2-κλ | 4 |
| 12 | IGF-2 | IGF-1 | − | IgG4-κλ | 4 |
| 14 | IGF-2 | IGF-1 | + | IgG2-κλ | 4 |
| 16 | IGF-2 | IGF-1 | + | IgG4-κλ | 4 |

Example 2

Recovery of Lymphocytes, B-Cell Isolations, Fusions and Generation of Hybridomas Immunized mice were sacrificed by cervical dislocation, and the draining lymph nodes harvested and pooled from each cohort. The lymphoid cells were dissociated by grinding in DMEM to release the cells from the tissues and the cells were suspended in DMEM. The cells were counted, and 0.9 ml DMEM per 100 million lymphocytes added to the cell pellet to resuspend the cells gently but completely. Using 100 µl of CD90+ magnetic beads per 100 million cells, the cells were labeled by incubating the cells with the magnetic beads at 4° C. for 15 minutes. The magnetically labeled cell suspension containing up to $10^8$ positive cells (or up to $2 \times 10^9$ total cells) was loaded onto a LS+ column and the column washed with DMEM. The total effluent was collected as the CD90-negative fraction (most of these cells were expected to be B cells).

The fusion was performed by mixing washed enriched B cells from above and nonsecretory myeloma P3X63Ag8.653 cells purchased from ATCC, cat.# CRL 1580 (Kearney et al, J. Immunol. 123, 1979, 1548-1550) at a ratio of 1:1. The cell mixture was gently pelleted by centrifugation at 800×g. After complete removal of the supernatant, the cells were treated with 2-4 mL of Pronase solution (CalBiochem, cat. # 53702; 0.5 mg/ml in PBS) for no more than 2 minutes. Then 3-5 ml of FBS was added to stop the enzyme activity and the suspension was adjusted to 40 ml total volume using electro cell fusion solution, (ECFS, 0.3M Sucrose, Sigma, Cat# S7903, 0.1 mM Magnesium Acetate, Sigma, Cat#M2545, 0.1 mM Calcium Acetate, Sigma, Cat# C4705). The supernatant was removed after centrifugation and the cells were resuspended in 40 ml ECFS. This wash step was repeated and the cells again were resuspended in ECFS to a concentration of $2 \times 10^6$ cells/ml.

Electro-cell fusion was performed using a fusion generator (model ECM2001, Genetronic, Inc., San Diego, Calif.). The fusion chamber size used was 2.0 ml, using the following instrument settings:

Alignment condition: voltage: 50 V, time: 50 sec.
Membrane breaking at: voltage: 3000 V, time: 30 µsec
Post-fusion holding time: 3 sec After ECF, the cell suspensions were carefully removed from the fusion chamber under sterile conditions and transferred into a sterile tube containing the same volume of Hybridoma Culture Medium (DMEM, JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15-30 minutes at 37° C., and then centrifuged at 400×g (1000 rpm) for five minutes. The cells were gently resuspended in a small volume of Hybridoma Selection Medium (Hybridoma Culture Medium supplemented with 0.5× HA (Sigma, cat. # A9666)), and the volume adjusted appropriately with more Hybridoma Selection Medium, based on a final plating of $5 \times 10^6$ B cells total per 96-well plate and 200 µl per well. The cells were mixed gently and pipetted into 96-well plates and allowed to grow. On day 7 or 10, one-half the medium was removed, and the cells re-fed with Hybridoma Selection Medium.

Example 3

Selection of Candidate Antibodies by Elisa

After 14 days of culture, hybridoma supernatants were screened for IGF-I/II-specific monoclonal antibodies. The ELISA plates (Fisher, Cat. No. 12-565-136) were coated with 50 µl/well of human IGF-I or IGF-II (2 µg/ml) in Coating Buffer (0.1 M Carbonate Buffer, pH 9.6, $NaHCO_3$ 8.4 g/L), then incubated at 4° C. overnight. After incubation, the plates were washed with Washing Buffer (0.05% Tween 20 in PBS) 3 times. 200 µl/well Blocking Buffer (0.5% BSA, 0.1% Tween 20, 0.01% Thimerosal in 1×PBS) were added and the plates incubated at room temperature for 1 hour. After incubation, the plates were washed with Washing Buffer three times. 50 µl/well of hybridoma supernatants, and positive and negative controls were added and the plates incubated at room temperature for 2 hours.

After incubation, the plates were washed three times with Washing Buffer. 100 µl/well of detection antibody goat anti-huIgGFc-HRP (Caltag, Cat. No. H10507), was added and the plates incubated at room temperature for 1 hour. In a secondary screen, the positives in first screening were screened in two sets, one for human IgG (heavy chain) detection and the other for human Ig kappa light chain detection (goat anti-hig kappa-HRP (Southern Biotechnology, Cat. No. 2060-05) in order to demonstrate fully human composition for both IgG and Ig kappa. After incubation, the plates were washed three times with Washing Buffer. 100 µl/well of TMB (BioFX Lab. Cat. No. TMSK-0100-01) were added and the plates allowed to develop for about 10 minutes (until negative control wells barely started to show color). 50 µl/well stop solution (TMB Stop Solution, (BioFX Lab. Cat. No. STPR-0100-01) was then added and the plates read on an ELISA plate reader at 450 nm. As indicated in Table 3, there were a total of 1,233 wells containing antibodies against IGF-I and -II.

All antibodies that bound in the ELISA assay were counter screened for binding to insulin by ELISA in order to exclude those that cross-reacted with insulin. The ELISA plates (Fisher, Cat. No. 12-565-136) were coated with 50 µl/well of recombinant insulin (concentration: 1 µg/ml; Sigma, catalog # I2643) in Coating Buffer (0.1 M Carbonate Buffer, pH 9.6, $NaHCO_3$ 8.4 g/L), then incubated at 4° C. overnight. As detailed in Table 3, a total of 1,122 antibodies from the original 1233 antibodies did cross react with insulin.

TABLE 3

SCREENING SUMMARY

| | | | | Confirmation Screen | | |
|---|---|---|---|---|---|---|
| Fn # | Mouse strain | Immunogen | Target with hG detection | Target with hK + hL detection | IGF-I(+) & IGF-II(+) | IGF-I(+) & IGF-II(+) and hu-Insulin (−) |
| 1 | G2 KL | IGF-I-KLH | IGF-II | IGF-I | 36 | 28 |
| 2 | G4 KL | IGF-I-KLH | IGF-II | IGF-I | 65 | 55 |
| 3 | G2 KL | IGF-II or IGF-II-KLH | IGF-I | IGF-II | 168 | 150 |
| 4 | G4 KL | IGF-II or IGF-II-KLH | IGF-I | IGF-II | 197 | 194 |
| 5 | G2 KL | IGF-I/-II-KLH | IGF-II | IGF-II | 54 | 50 |
| 6 | G4 KL | IGF-I/-II-KLH | IGF-II | IGF-II | 101 | 86 |
| 7 | G2 KL | IGF-II/-I-KLH | IGF-II | IGF-II | 294 | 271 |
| 8 | G4 KL | IGF-II/-I or IGF-II/-I-KLH | IGF-II | IGF-II | 318 | 288 |
| | | Total F1 to F4 | | | 466 | 427 |
| | | Total F5 to F8 | | | 767 | 695 |
| | | Total | | | 1,233 | 1,122 |

Finally, the antibodies that were selected in the counter-screen were then tested by ELISA to confirm binding to mouse IGF-I and IGF-II proteins. A total of 683 hybridoma lines were identified that have cross-reactivity with mouse IGF-I/II. Accordingly, these hybridoma lines expressed antibodies that bound to human IGF-I, human IGF-II, mouse IGF-I and mouse IGF-II, but did not bind to human insulin.

Example 4

Inhibition of IGF-I and IGF-II Binding to IGF-IR

The purpose of this study was to screen the 683 anti-IGF-I/II human IgG2 and IgG4 antibodies at the hybridoma supernatant stage for neutralizing activity, as determined by inhibition of IGF-I and IGF-II binding to the IGF-IR receptor. Thus, a receptor/ligand binding assay was performed with NIH3T3 cells that overexpress the human IGF-IR receptor, as described below.

Briefly, multi-screen filter plates (MultiScreen 0.65 μM 96-well PVDF, Millipore, Cat. No. MADV N0B 10) were blocked with blocking buffer (PBS containing 10% BSA with 0.02% NaN$_3$) at 200 μL/well overnight at 4° C. [$^{125}$I]-labeled IGF (Amersham Life Sciences Cat No. IM172 (IGF-I) or IM238 (IGF-II)) at 100 μCi/ml and 50 nM was diluted to the appropriate concentration (70 pM final for IGF-I and 200 pM final for IGF-II) in binding buffer (PBS containing 2% BSA with 0.02% NaN$_3$). The blocking buffer-coated filter plate was washed once with 200 μL PBS, and 50 μL anti-IGF-I/II Ab supernatants (diluted in binding buffer to 25% final volume) were preincubated with 25 μL of [$^{125}$I]-IGF in the MultiScreen plate for 30-60 minutes on ice. Subconfluent NIH3T3 mouse fibroblasts stably expressing hIGF-IR (obtained from AstraZeneca) were harvested with trypsin and resuspended in cold binding buffer at 6×10$^6$/ml, and 25 μL of cells were added to the plate for a two-hour incubation on ice. The plate was washed four times with 200 μL cold PBS and dried overnight. Twenty-five μL/well of scintillant (SuperMix cocktail, Wallac/Perkin Elmer Cat No. 1200-439) was added and the plates were read using a Microbeta Trilux reader (Wallac).

The following controls were used per screening plate: no antibody (total IGF bound), control neutralizing anti-IGF-I (#05-172, Upstate) or anti-IGF-II (#MAB292, R&D Systems) mAbs at 50 μg/ml (non-specific background) and 0.075 to 0.5 μg/ml (approximate EC50 values of the neutralizing antibodies), and isotype-matched control human IgG2 (PK16.3.1, Abgenix, lot #360-154) or IgG4 (108.2.1, Abgenix, lot#718-53A) mAbs at a concentration of 0.5 μg/ml (approximate EC50 value of neutralizing antibodies). An additional titration of control neutralizing antibodies and isotype-matched control human antibodies was added to one plate per screening assay (1/10 serial dilution from 50 ug/ml (333.3 nM)). All controls with or without antibodies were prepared in binding buffer supplemented with anti-KLH human IgG2 or IgG4 exhaust supernatant at 25% final volume.

The percentage of inhibition was determined as follows:

% Inhibition=([(Mean CPM Total $^{125}$I-IGF bound)−(Mean CPM $^{125}$I-IGF bound in the presence of antibody)]/[(Mean CPM Total $^{125}$I-IGF bound)−(Mean CPM $^{125}$I-IGF bound in the presence of an excess of control neutralizing antibody*)])×100

* the non-specific background was determined as CPM of cells with an excess of control neutralizing anti-IGF Ab (50 ug/ml, 333.3 nM), which was found to be equivalent to an excess of cold IGF (less than or equal to 10% of total CPM)

The anti-IGF-I/II supernatant screening was split by isotype because of radiolabeled ligand availability issues. As shown in Table 4, supernatants from the anti-IGF-I/II antibodies with an IgG2 isotype (293 total) were first screened against radiolabeled IGF-I. A cut-off at 40% inhibition was initially applied to this screening (i.e. hybridoma lines inhibiting at 40% and above were selected), and 111 hits were selected for subsequent screening against IGF-II. Of the 111 hits, a total of 91 lines were found to inhibit IGF-II binding to its receptor with a 50% cut-off. A total of 71 final hits were selected by taking supernatants that neutralized 50% of both IGF-I and IGF-II activity.

All the supernatants expressing IgG4 isotypes (390 total) were initially screened against radiolabeled IGF-II, and 232 hits with a cut-off at 50% inhibition were subsequently screened against IGF-I. A total of 90 lines were able to inhibit IGF-I binding to its receptor with a 50% cut-off. After combining the hits for IgG2 (71) and IgG4 (90), a total of 161 lines were obtained which inhibited IGF-I and IGF-II by 50% or more.

In conclusion, from the 683 original supernatants, 343 (111 IgG2 and 232 IgG4, 50.2%) were selected from the first screening with either IGF-I or IGF-II. A total of 161 final hits were obtained (23.6% of original lines), which are able to block both IGF-I and IGF-II binding to IGF-IR with an overall cut-off criteria of 50% inhibition.

TABLE 4

ANTI-IGF-I/II EXHAUST SUPERNATANT SCREENING SUMMARY (50% CUT-OFF)

| Fusion # | Mouse strain | Immunogen | ESN Activity hIGF-II with hG+/hK+ or hG+/hL+ | R/L Binding Assay IGF-I | IGF-I+ % Total | R/L Binding Assay IGF-II on IGF-I+ | IGF-I/II+ % Total | R/L Binding Assay IGF-II | IGF-II+ % Total | R/L Binding Assay IGF-I on IGF-II+ | IGF-I/II+ % Total |
|---|---|---|---|---|---|---|---|---|---|---|---|
| 1 | G2 KL | IGF-I-KLH | 14 | 12 | 85.7 | 1 | 7.1 | | | | |
| 2 | G4 KL | IGF-I-KLH | 20 | | | | | 4 | 20.0 | 4 | 20.0 |
| 3 | G2 KL | IGF-II or IGF-II-KLH | 49 | 13 | 26.5 | 4 | 8.2 | | | | |
| 4 | G4 KL | IGF-II or IGF-II-KLH | 114 | | | | | 86 | 75.4 | 36 | 31.6 |
| 5 | G2 KL | IGF-I/-II-KLH | 32 | 11 | 34.4 | 7 | 21.9 | | | | |
| 6 | G4 KL | IGF-I/-II-KLH | 47 | | | | | 21 | 44.7 | 8 | 17.0 |
| 7 | G2 KL | IGF-II/-I-KLH | 198 | 75 | 37.9 | 59 | 29.8 | | | | |
| 8 | G4 KL | IGF-II/-I or IGF-II/-I-KLH | 209 | | | | | 121 | 57.9 | 42 | 20.1 |
| | | | 683 | 111 Cut-off 40% | 16.3 IgG2 | 71 | 10.4 | 232 | 34.0 IgG4 | 90 | 13.2 |

Example 5

High Antigen and Limited Antigen Elisas

In order to determine the relative affinities among the 161 hybridoma lines selected in Example 4, as well as the concentration of antibody in the supernatants of each line, high antigen (HA) and limited antigen (LA) ELISA assays were carried out. In the HA quantitation assay, the high antigen concentration and overnight incubation limit the effect of antibody affinity, allowing for quantitation of the relative amount of antigen-specific antibody present in each sample. The low antigen concentration in the LA assay limits the effect of antibody concentration and results in a ranking of antibodies based on their relative affinity.

High Antigen Quantitation Assay

ELISA plates were coated with relatively large amounts of either IGF-I or IGF-II antigen (R&D Systems, Inc., Minneapolis, Minn. Cat. No. 291-G1 and 292-G2 respectively) at 500 ng/ml (67 nM). Antibody-containing hybridoma supernatants were titrated over a dilution range of 1:50 to 1:12200. A control of a known IGF-specific antibody (R&D Systems, Inc., Minneapolis, Minn. Cat. No. MAB291 and MAB292 respectively) was used to define the linear range of the assay. Data within the linear range were then used to derive the relative concentration of the IGF-specific antibody in each titrated sample.

Limited Antigen Assay

Microtiter plates were coated with low concentrations of antigen. Fifty microliters (50 µL) of IGF-I or IGF-II at 64, 32, 16, 8, 4, and 2 ng/ml (covering a range of 8.5 nM to 0.26 nM) in 1% skim milk/1×PBS pH 7.4/0.5% azide was added to each well. The plate was incubated for 30 minutes.

Plates were washed four times (4×) with water, and 50 µL of hybridoma supernatant containing test antibodies diluted 1:25 in 1% skim milk/1×PBS pH 7.4/0.5% azide were added to the wells. Plates were wrapped tightly with plastic wrap or paraffin film, and incubated overnight with shaking at room temperature.

On the following day, all plates were washed five times (5×) and 50 µL goat anti-Human IgG Fc HRP polyclonal antibody at a concentration of 0.5 ug/ml in 1% milk, 1×PBS pH 7.4 was added to each well. The plates were incubated for 1 hour at room temperature.

Plates were washed at least five times (5× with tap water). Fifty microliters (50) µL of HPR substrate TMB was added to each well, and the plate were incubated for 30 minutes. The HRP-TMB reaction was stopped by adding 50 µL of 1M phosphoric acid to each well. Optical density (absorbance) at 450 nm was measured for each well of the plate.

Data Analysis

OD values of test antibodies were averaged and the range was calculated. Antibodies with the highest signal and acceptably low standard deviation were selected as antibodies having a higher affinity for the antigen than did a reference antibody.

An analysis was then made to select top antibodies based on either neutralization (Example 4), potency (low antibody concentration as determined by HA ELISA and high inhibition of ligand binding), affinity (LA ELISA), or all three criteria. From this analysis, a list of 25 antibodies was generated. A separate analysis based on average % inhibition of IGF-I and -II binding and affinity for both IGF-I and IGF-II generated a second list of 25 antibodies. Sixteen antibodies were common to both lists, resulting in a final list of 40 antibodies. The LA and HA results for these 40 antibodies are summarized in Table 5. These 40 lines were selected for cloning, of which 33 were successfully cloned.

TABLE 5

RESULTS OF HIGH AND LIMITED ANTIGEN ELISA FOR TOP 40 ANTIBODIES

| | IGF1 HA | | IGF2 HA | | IGF1 | IGF2 | IGF1 | IGF2 |
|---|---|---|---|---|---|---|---|---|
| Line ID | Avg (ug/ml) HA1 | Std. Dev HA1 | Avg (ug/ml) HA2 | Std. Dev HA2 | LA IGF1 2 ng/ml | LA IGF2 2 ng/ml | IGF1 4 ng/ml | IGF2 4 ng/ml |
| 4.121 | 1.16 | 0.16 | 3.56 | 1.34 | 0.56 | 0.53 | 1.14 | 0.90 |
| 4.141 | 1.99 | 0.22 | 1.99 | 0.21 | 0.57 | 0.79 | 1.25 | 1.52 |

TABLE 5-continued

RESULTS OF HIGH AND LIMITED ANTIGEN ELISA FOR TOP 40 ANTIBODIES

| Line ID | IGF1 HA Avg (ug/ml) HA1 | IGF1 HA Std. Dev HA1 | IGF2 HA Avg (ug/ml) HA2 | IGF2 HA Std. Dev HA2 | IGF1 LA IGF1 2 ng/ml | IGF2 LA IGF2 2 ng/ml | IGF1 LA IGF1 4 ng/ml | IGF2 LA IGF2 4 ng/ml |
|---|---|---|---|---|---|---|---|---|
| 4.142 | 4.70 | 0.21 | 3.65 | 0.31 | 0.78 | 1.00 | 1.76 | 1.78 |
| 4.143 | 1.74 | 0.17 | 2.03 | 0.41 | 0.60 | 0.99 | 1.20 | 1.91 |
| 4.25 | 1.26 | 0.23 | 1.48 | 0.36 | 0.71 | 0.81 | 1.31 | 1.54 |
| 4.69 | 7.17 | 1.16 | 6.50 | 0.53 | 0.80 | 0.80 | 1.50 | 1.54 |
| 4.90 | 1.15 | 0.12 | 3.68 | 0.77 | 0.58 | 0.48 | 1.04 | 0.89 |
| 7.118 | 10.34 | 1.26 | 10.32 | 1.90 | 0.81 | 0.85 | 1.56 | 1.44 |
| 7.123 | 13.4 | 3.2 | 12.0 | 2.8 | 1.0 | 1.7 | 1.66 | 2.58 |
| 7.127 | 7.28 | 0.44 | 6.59 | 1.55 | 1.19 | 1.37 | 2.29 | 2.40 |
| 7.130 | 4.32 | 0.32 | 3.51 | 1.34 | 0.64 | 1.17 | 1.36 | 1.98 |
| 7.146 | 12.04 | 0.98 | 9.63 | 0.6 | 0.2 | 0.86 | 0.29 | 1.58 |
| 7.158 | 9.29 | 0.49 | 7.1 | 0.56 | 1.71 | 1.42 | 3.00 | 2.46 |
| 7.159 | 16.53 | 1.83 | 41.1 | | 0.56 | 1.65 | 0.98 | 2.47 |
| 7.160 | 4.9 | 0.5 | 5.1 | 0.2 | 1.7 | 2.2 | 3.14 | 3.30 |
| 7.175 | 8.46 | 0.49 | 6.21 | 1.22 | 0.13 | 0.34 | 0.14 | 0.62 |
| 7.202 | 11.94 | 1.98 | 15.24 | 1.72 | 1.11 | 1.68 | 2.28 | 2.69 |
| 7.212 | 11.30 | 1.90 | 10.86 | 1.26 | 0.97 | 0.93 | 2.22 | 1.54 |
| 7.215 | 10.11 | 2.05 | 10.94 | 1.39 | 1.01 | 1.09 | 2.25 | 1.93 |
| 7.23 | 4.30 | 0.26 | 3.99 | 0.29 | 0.55 | 1.22 | 1.40 | 2.17 |
| 7.234 | 4.7 | 1.4 | 3.1 | 0.4 | 0.7 | 1.4 | 1.79 | 2.44 |
| 7.251 | 3 | 0.41 | 1.93 | 0.17 | 1.09 | 1.02 | 1.31 | 1.53 |
| 7.252 | 8.25 | 0.51 | 5.55 | 1.68 | 1.22 | 1.23 | 2.53 | 2.09 |
| 7.268 | 7.58 | 0.42 | 5.07 | 0.92 | 1.47 | 1.37 | 3.06 | 2.42 |
| 7.29 | 12.5 | 1.24 | 23.53 | 4.7 | 0.18 | 0.39 | 0.27 | 0.49 |
| 7.3 | 13.18 | 2.12 | 8.83 | 0.58 | 0.81 | 1.28 | 2.07 | 1.96 |
| 7.34 | 12.54 | 1.99 | 14.67 | 3.05 | 0.21 | 1.07 | 0.44 | 1.84 |
| 7.41 | 3.69 | 0.19 | 4.97 | 0.8 | 1.02 | 1.53 | 2.21 | 2.32 |
| 7.56 | 14.6 | 2.0 | 21.7 | 3.7 | 1.3 | 1.4 | 2.38 | 2.46 |
| 7.58 | 17.52 | 0.01 | 27.54 | 6.22 | 0.21 | 1.15 | 0.47 | 1.82 |
| 7.66 | 6.02 | 0.81 | 6.18 | 0.71 | 0.49 | 0.97 | 1.42 | 1.53 |
| 7.77 | 8.42 | 0.18 | 7.25 | 1.12 | 0.64 | 0.46 | 1.50 | 1.00 |
| 7.85 | 22.67 | 0.68 | 23.63 | 0.93 | 0.1 | 0.33 | 0.16 | 0.51 |
| 7.99 | 7.9 | 0.2 | 5.9 | 1.6 | 0.9 | 1.0 | 1.87 | 1.65 |
| 8.119 | 1.26 | 0.00 | 0.77 | 0.16 | 2.37 | 0.79 | 3.77 | 1.36 |
| 8.141 | 5.96 | 0.50 | 4.12 | 0.61 | 1.80 | 0.61 | 3.02 | 1.08 |
| 8.146 | 4.03 | 0.45 | 2.55 | 0.74 | 0.97 | 1.06 | 2.13 | 1.98 |
| 8.287 | 4.8 | 0.1 | 2.8 | 0.8 | 2.2 | 1.6 | 3.80 | 2.91 |
| 8.8 | 2.00 | 0.17 | 1.45 | 0.25 | 1.72 | 0.77 | 3.13 | 1.46 |
| 8.86 | 3.15 | 0.19 | 2.36 | 0.24 | 0.92 | 1.35 | 1.76 | 2.18 |

Example 6

Binding of Antibodies to IGF-I and IGF-II Bound to IGFBP-3

IGF-I and -II circulate in serum mostly bound to IGF-binding proteins (IGFBPs). One aim was to identify antibodies that do not recognize IGFs in complex with IGFBPs, in order to avoid in vivo depletion of anti-IGF antibodies. The following assay format was developed for the characterization of antibodies that recognize IGF-I or IGF-II when these growth factors are complexed with IGFBP-3. Specifically, this assay tested the ability of IGF in IGF/anti-IGF antibody complexes to bind IGFBP-3.

Antibody-Mediated Block of Capture of IGF by IGFBP-3

An assay was developed wherein complexes were preformed between IGF-I or IGF-II and IGF-specific antibodies from the aforementioned examples. The ability of these complexes to bind to IGFBP-3 was tested using AlphaScreen assay technology (PerkinElmer). In a 384-well plate, 10 µL 1:20 diluted hybridoma supernatants were mixed with 10 µL of 3 nM biotinylated IGF-I or IGF-II and incubated at room temperature for 2 hours. Streptavidin-coated AlphaScreen donor beads and IGFBP-3-coupled AlphaScreen acceptor beads (10 uL of a mixture, for a 1/60 final dilution of the hybridoma supernatants) were added, and the incubation was continued for another hour. Samples were then read in a Packard Fusion plate reader.

Three commercially available anti-IGF monoclonal antibodies M23 (Cell Sciences), 05-172 (Upstate) and MAB291 (R&D Systems) showed different abilities to inhibit IGF binding to IGFBP with IC50 values ranging from low ng/mL to 100 ng/mL. No inhibition of IGF-I binding to the IGFBP-3 was observed with irrelevant mouse IgG and human IgG up to 10 µg/mL, suggesting that the anti-IGF-I effect is specific. Commercially available monoclonal antibodies 05-166 (Upstate) and MAB292 (R&D) showed a significant difference in affinity for inhibition of IGF-II/IGFBP-3 interactions. These experiments show that anti-IGF mAbs can block the binding of IGF to IGFBP-3, giving an assay that could be used for screening purified antibodies from hybridoma lines. The next step was to evaluate the effects of exhausted hybridoma medium on the assay signal.

Serial dilutions of the hybridoma medium and anti-KLH hybridoma exhaust supernatants were tested in the assay system. When hybridoma supernatants were diluted 1:10 in preparation for preincubation with IGFI/II (final dilution in the assay was 1:60), there was almost no effect of the medium on the assay results. Based on these data, hybridoma supernatants were diluted for preincubation with IGF, providing the preferred 1/60 dilution final dilution in the assay.

Six hundred eighty-three exhaust supernatants positive for IGF-I and IGF-II binding were examined for their ability to inhibit binding of IGF to IGFBP-3. Inhibition above 50% for IGF-I and above 60% for IGF-II were used as cut-off criteria. The summary results of the screen using these cut-offs are shown in Table 6.

TABLE 6

NUMBERS OF POSITIVE HITS IDENTIFIED IN THE SCREEN

| Samples | Inhibition-> | IGF-I >50% | IGF-II >60% | IGF-I/II |
|---|---|---|---|---|
| 376 | (plates 1–4) | 48 | 51 | 19 |
| 307 | (plates 5–8) | 39 | 78 | 32 |
| 683 | Total | 87 | 129 | 51 |

The IGFBP competition assay using the AlphaScreen assay identified 87 samples inhibiting IGF-I binding to IGFBP-3 and 129 samples inhibiting IGF-II binding to IGFBP-3 among 683 tested supernatants. Fifty-one samples demonstrated dual competition of IGF-I and IGF-II. However, in order to more carefully reproduce the function or behavior of the antibodies in vivo, where the IGF and the IGFBP complex would be largely preformed, additional assays, as described in example 8 were performed.

Example 7

Determination of Anti-IGF-I and IGF-II Antibody Affinity Using Biacore Analysis (Low Resolution Screen)

Low Resolution Screen of 34 Purified Monoclonal Antibodies

The label-free surface plasmon resonance (SPR), or Biacore, was utilized to measure the antibody affinity to the antigen. For this purpose, a high-density goat anti-human antibody surface over a CM5 Biacore chip was prepared using routine amine coupling. All the mAbs were diluted to approximately 20 μg/ml in HBS-P running buffer containing 100 μg/ml BSA. Each mAb was captured on a separate surface using a 30-second contact time at 10 μL/min., and a 5-minute wash for stabilization of the mAb baseline.

IGF-I was injected at 335.3 nM over all surfaces at 23° C. for 120 seconds, followed by a 5-minute dissociation, using a flow rate of 100 μL/min. The samples were prepared in the HBS-P running buffer described above. The surfaces were regenerated after every capture/injection cycle with one 15-second pulse of 146 mM phosphoric acid (pH 1.5). The same capture/injection cycles were repeated for each antibody with 114.7 nM IGF-II. Drift-corrected binding data for the 34 mAbs was prepared by subtracting the signal from a control flow cell and subtracting the baseline drift of a buffer injected just prior to each antigen injection. Data were fit globally to a 1:1 interaction model using CLAMP to determine the binding kinetics (David G. Myszka and Thomas Morton (1998) "CLAMP©: a biosensor kinetic data analysis program," TIBS 23, 149-150). A mass transport coefficient was used in fitting the data. The kinetic analysis results of IGF-I and IGF-II binding at 25° C. are listed in Table 7 below. The mAbs are ranked from highest to lowest affinity.

IGF-I Binding Data

Most mAbs fit a 1:1 model reasonably well. MAbs 4.90.2 and 4.141.1 were characterized by extremely complex data. These mAbs were listed with an asterisk in Table 7 because no meaningful kinetic constants could be estimated from the 1:1 model fit. The latter off-rate phase appears to be very slow for both of these mAbs (at least $1 \times 10^{-5}$ sec$^{-1}$), which might make these two mAbs useful as therapeutic compounds.

IGF-II Binding Data

Most mAbs fit a 1:1 model reasonably well. The off-rate for mAb 7.159.2 was held constant at $1 \times 10^{-5}$ sec$^{-1}$ because there was not enough decay data to adequately estimate $k_d$.

The low-resolution Biacore studies in this example are designed as a semi-quantitative ranking approach. In order to acquire more accurate information regarding the characteristic rate constants and affinities of individual mAbs, high-resolution Biacore studies were carried out as described in Example 8.

Example 8

Determination of Anti-IGF-I and IGF-II Antibody Affinity Using Biacore Analysis (High Resolution Screen)

A high resolution Biacore analysis was performed to further measure the antibody affinity to the antigen. mAbs 7.159.2, 7.234.2, 7.34.1, 7.251.3, and 7.160.2 were each cap-

TABLE 7

IGF-I AND IGF-II LOW RESOLUTION BIACORE SCREEN OF 34 MONOCLONAL ANTIBODIES

| Sample | IGF-II | | | IGF-I | | |
|---|---|---|---|---|---|---|
| | $k_a$ (M$^{-1}$s$^{-1}$) | $k_d$ (s$^{-1}$) | $K_D$ (pM) | $k_a$ (M$^{-1}$s$^{-1}$) | $k_d$ (s$^{-1}$) | $K_D$ (pM) |
| 7.159.2 | $3.5 \times 10^6$ | $1.0 \times 10^{-5}$* | 2.9 | $4.3 \times 10^6$ | $9.3 \times 10^{-4}$ | 216.0 |
| 8.86.1 | $6.1 \times 10^6$ | $2.4 \times 10^{-4}$ | 39.3 | $3.4 \times 10^6$ | $1.3 \times 10^{-2}$ | 3823.0 |
| 4.25.1 | $9.3 \times 10^6$ | $4.1 \times 10^{-4}$ | 44.1 | $5.1 \times 10^6$ | $6.9 \times 10^{-3}$ | 1353.0 |
| 7.234.2 | $6.4 \times 10^6$ | $2.9 \times 10^{-4}$ | 45.3 | $6.7 \times 10^6$ | $2.2 \times 10^{-3}$ | 328.0 |
| 7.160.2 | $4.6 \times 10^6$ | $2.5 \times 10^{-4}$ | 54.3 | $5.6 \times 10^6$ | $3.3 \times 10^{-3}$ | 589.0 |
| 7.146.3 | $3.2 \times 10^6$ | $1.8 \times 10^{-4}$ | 56.2 | $3.8 \times 10^6$ | $8.7 \times 10^{-3}$ | 2289.0 |
| 7.34.1 | $3.0 \times 10^6$ | $1.8 \times 10^{-4}$ | 60.0 | $5.2 \times 10^6$ | $3.2 \times 10^{-3}$ | 615.0 |
| 7.123.1 | $4.0 \times 10^6$ | $3.4 \times 10^{-4}$ | 85.0 | $4.3 \times 10^6$ | $9.0 \times 10^{-3}$ | 2093.0 |
| 7.202.3 | $1.8 \times 10^6$ | $1.7 \times 10^{-4}$ | 94.4 | $1.2 \times 10^6$ | $5.4 \times 10^{-3}$ | 4500.0 |
| 4.141.1 | $4.9 \times 10^6$ | $4.7 \times 10^{-4}$ | 95.9 | * | * | * |
| 7.215.2 | $3.2 \times 10^6$ | $3.3 \times 10^{-4}$ | 103.0 | $3.6 \times 10^6$ | $2.6 \times 10^{-2}$ | 7222.0 |
| 8.287.2 | $2.4 \times 10^6$ | $2.5 \times 10^{-4}$ | 104.0 | $7.7 \times 10^5$ | $1.3 \times 10^{-3}$ | 1688.0 |
| 8.146.2 | $7.7 \times 10^6$ | $8.0 \times 10^{-4}$ | 104.0 | $2.4 \times 10^6$ | $1.3 \times 10^{-2}$ | 5417.0 |
| 4.143.2 | $1.1 \times 10^7$ | $1.2 \times 10^{-3}$ | 109.0 | $6.4 \times 10^6$ | $1.9 \times 10^{-2}$ | 2969.0 |
| 7.251.3 | $3.5 \times 10^6$ | $4.3 \times 10^{-4}$ | 123.0 | $4.6 \times 10^6$ | $4.3 \times 10^{-3}$ | 935.0 |
| 7.99.1 | $6.9 \times 10^6$ | $9.9 \times 10^{-4}$ | 143.0 | $6.0 \times 10^6$ | $4.8 \times 10^{-3}$ | 800.0 |
| 4.142.2 | $5.3 \times 10^6$ | $8.5 \times 10^{-4}$ | 160.0 | $8.5 \times 10^6$ | $1.9 \times 10^{-2}$ | 2235.0 |
| 7.41.3 | $3.2 \times 10^6$ | $5.5 \times 10^{-4}$ | 172.0 | $5.2 \times 10^6$ | $2.9 \times 10^{-3}$ | 558.0 |
| 7.56.3 | $3.3 \times 10^6$ | $6.0 \times 10^{-4}$ | 182.0 | $4.8 \times 10^6$ | $3.1 \times 10^{-3}$ | 646.0 |
| 7.127.1 | $4.1 \times 10^6$ | $7.6 \times 10^{-4}$ | 185.0 | $4.9 \times 10^6$ | $3.5 \times 10^{-3}$ | 714.0 |
| 8.8.3 | $4.0 \times 10^6$ | $7.8 \times 10^{-4}$ | 195.0 | $3.1 \times 10^6$ | $8.2 \times 10^{-4}$ | 264.0 |
| 7.158.2 | $3.4 \times 10^6$ | $6.7 \times 10^{-4}$ | 197.0 | $4.4 \times 10^6$ | $2.2 \times 10^{-3}$ | 500.0 |
| 7.23.3 | $3.3 \times 10^6$ | $6.5 \times 10^{-4}$ | 197.0 | $4.1 \times 10^6$ | $5.8 \times 10^{-3}$ | 1415.0 |
| 7.252.1 | $3.2 \times 10^6$ | $6.5 \times 10^{-4}$ | 203.0 | $2.3 \times 10^6$ | $2.1 \times 10^{-3}$ | 913.0 |
| 7.66.1 | $3.6 \times 10^6$ | $7.7 \times 10^{-4}$ | 214.0 | $2.0 \times 10^6$ | $2.5 \times 10^{-3}$ | 1250.0 |
| 7.130.1 | $4.2 \times 10^6$ | $1.0 \times 10^{-3}$ | 238.0 | $4.6 \times 10^6$ | $1.8 \times 10^{-2}$ | 3913.0 |
| 4.90.2 | $4.9 \times 10^6$ | $1.2 \times 10^{-3}$ | 245.0 | * | * | * |
| 7.3.3 | $3.2 \times 10^6$ | $8.8 \times 10^{-4}$ | 275.0 | $4.1 \times 10^6$ | $3.9 \times 10^{-3}$ | 951.0 |
| 7.118.1 | $4.6 \times 10^6$ | $1.5 \times 10^{-3}$ | 326.0 | $5.6 \times 10^6$ | $5.1 \times 10^{-3}$ | 911.0 |
| 7.212.1 | $4.2 \times 10^6$ | $1.6 \times 10^{-3}$ | 381.0 | $3.1 \times 10^6$ | $6.0 \times 10^{-3}$ | 1935.0 |
| 7.175.2 | $1.3 \times 10^6$ | $7.4 \times 10^{-4}$ | 569.0 | $1.8 \times 10^6$ | $2.0 \times 10^{-2}$ | 11111.0 |
| 4.121.1 | $5.5 \times 10^6$* | $3.2 \times 10^{-3}$* | 582.0* | $1.5 \times 10^6$ | $2.1 \times 10^{-3}$ | 1400.0 |
| 7.85.2 | $1.9 \times 10^6$ | $1.3 \times 10^{-3}$ | 684.0 | $2.2 \times 10^6$ | $2.9 \times 10^{-2}$ | 13182.0 |
| 7.58.3 | $8.9 \times 10^6$ | $7.9 \times 10^{-3}$ | 888.0 | $7.2 \times 10^6$ | $3.2 \times 10^{-2}$ | 4444.0 | tured and the IGF-I and IGF-II antigens were each injected over a range of concentrations. The resulting binding constants are listed in Table 8.

TABLE 8

ANTI-IGF ANTIBODY AFFINITY DETERMINED BY LOW- AND HIGH-RESOLUTION BIACORE ANALYSIS

|  | Low resolution $K_D$ (pM) | | High Resolution $K_D$ (pM) | |
| --- | --- | --- | --- | --- |
| mAb | IGF-I | IGF-II | IGF-I | IGF-II |
| 7.159.2 | 216.0 | 2.9 | 294.0 | 1.9 |
| 7.234.2 | 328.0 | 45.3 | 3760.0 | 295.0 |
| 7.34.1 | 615.0 | 60.0 | 436.0 | 164.0 |
|  |  |  | 421.0 | 162.0 |
| 7.251.3 | 935.0 | 123.0 | 452.0 | 47.4 |
| 7.160.2 | 589.0 | 54.3 | 2800.0 | 237.0 |

Thus, embodiments of the invention can include an antibody that will preferentially bind to IGF-II, but that will cross-react with IGF-I, binding to IGF-II with higher affinity than to IGF-I. For example, the antibody can bind to IGF-II with 2.5 times greater affinity than to IGF-I. In certain embodiments, the antibody can bind to IGF-II with at least 5, at least 10, at least 25, at least 50 or at least 150 times greater affinity than to IGF-I.

Screening of Preformed IGF-I/GFBP-3 Complexes

The IGFBP competition assay described in Example 6 identified 87 samples inhibiting IGF-I binding to IGFBP-3 and 129 samples inhibiting IGF-II binding to IGFBP-3 among 683 tested supernatants. Fifty-one samples demonstrated dual competition of IGF-I and IGF-II. However, in order to more carefully reproduce the function or behavior of the antibodies in vivo, where the IGF and the IGFBP complex would be largely preformed, the following Biacore assays were performed on selected antibodies.

Six selected antibodies were screened to determine whether they bind IGF-I or IGF-II in complex with IGFBP. All six of the selected mAbs (7.159.2, 7.146.3, 7.34.1, 7.251.3, 7.58.3, and unrelated control antibody ABX-MA1) were covalently immobilized to a high surface capacity (5,400-12,800 RUs) on two CM5 Biacore chips using routine amine coupling with a Biacore 2000 instrument. One flow cell on each CM5 chip was activated and blocked (no mAb immobilized) for use as a control surface.

Next, IGF-I and IGFBP-3 were mixed together in Hepes buffered saline, pH 7.4, 0.005% P-20, 100 µg/ml BSA (HBS-P), to make a final solution of 193 nM and 454 nM, respectively. IGF-II and IGFBP-3 were mixed together to make a final solution of 192 nM and 455 nM, respectively. Under these conditions, IGF-I and IGF-II were 99.97% complexed by IGFBP-3. Equilibrium was reached within minutes under these conditions. Solutions of complexed IGF-I/IGFBP-3 and IGF-II/IGFBP-3 were flowed across the various mAb surfaces at 40 µL/min and 23° C., for 180 seconds and dissociation was followed for 120 seconds. Uncomplexed IGF-I and IGF-II were then flowed across each surface at 193 nM and 192 nM, respectively, and IGFBP-3 was flowed across each surface at 454 nM. The surfaces were regenerated with a 20 second pulse of 10 mM glycine, pH 2.0.

The sensorgrams were processed using the program Scrubber by subtracting the bulk refractive index change and any nonspecific binding signal of the analyte to the blank surface from the binding signal from surfaces with mAb immobilized. After blank correction subtraction, the sensorgrams were referenced a second time by subtracting an average sensorgram for buffer injections over a specific flow cell. This "double reference" corrected the mAb binding sensorgrams for any systematic errors present on a particular flow cell.

Complexed and uncomplexed IGF-I/IGFBP-3 and IGF-II/IGFBP-3 bound fairly weakly to the bound antibodies, with a rough estimate of the nonspecific binding interaction being a $K_D>1$ µM for all six mAbs, including negative control ABX-MA1 (See Table 9). However, with ABX-MA1 the IGF-I/II binding was weak and indicated nonspecific binding interactions occurred with all these three analytes. Apparently, the IGF/IGFBP-3 complexes bind slightly stronger to all these mAbs than IGFBP-3 does alone. However, because both IGF-I, IGF-II and IGBP-3 appear to bind nonspecifically to these mAbs themselves, when they are both bound together, this results in an even "stickier" nonspecific binding protein complex, which explains the greater binding signal for the complex. The IGF-I/II/IGFBP-3 complexes and IGFBP-3 bound to the control surface significantly also indicating the non-specificity of these two proteins. However, in the sensorgrams below this background binding is subtracted out in the first reference during data processing, as described above.

This experiment suggests that although 51 of the samples were previously shown to inhibit binding of IGF-I/II to IGFBP3 (Example 6), the antibodies may also bind to the IGF/IGFBP complex in vitro.

TABLE 9

BINDING SUMMARY FOR IGF-I/IGFBP-3 AND IGF-II/IGFBP-3 BINDING TO SIX MABS.

| mAb | IGF-I/IGFBP-3 complex | IGF-II/IGFBP-3 complex | IGFBP-3 | IGF-I (or II) |
| --- | --- | --- | --- | --- |
| 7.159.2 | + | + | + | +++ |
| 7.146.3 | + | ++ | + | +++ |
| 7.34.1 | + | ++ | + | +++ |
| 7.251.3 | ++ | ++ | ++ | +++ |
| 7.58.3 | ++ | ++ | ++ | +++ |
| ABX-MA1 | + | + | + | + |

+, slight binding relative to IGF-I or IGF-II to the mAb
++, medium binding relative to IGF-I or IGF-II to the mAb
+++, strong binding relative to IGF-I or IGF-II binding to the mAb
*These ratings DO NOT indicate the $K_D$ for these interactions.

Example 9

Determination of Anti-Insulin Antibody Affinity Using Biacore Analysis (Low Resolution Screen)

The cross-reactivity of antibodies to IGF-I/II was further investigated by measuring the affinity of the mAbs to human insulin. IGF-I/II antibodies were immobilized to the CM5 Biacore chips, and insulin in solution was injected for the determination of the on-rate and off-rate. Five mAbs, including 7.234.2, 7.34.1, 7.159.2, 7.160.2, and 7.251.3, were tested in this experiment. Insulin diluted to 502 nM in the running buffer was injected over all capture surfaces.

No insulin binding to any of the mAbs was observed at 502 nM insulin. These results suggest that there is no apparent cross-reactivity of the IGF-I/II mAbs with insulin.

Example 10

Binding of Antibodies

Epitope binning was performed to determine which of the anti-IGF-I/II antibodies would cross compete with one another, and thus were likely to bind to the same epitope on IGF-I/II. The binning process is described in U.S. Patent Application 20030175760, also described in Jia et al., J. Immunol. Methods, (2004) 288:91-98, both of which are incorporated by reference in entirety. Briefly, Luminex beads were coupled with mouse anti-huIgG (Pharmingen #555784) following the protein coupling protocol provided on the Luminex website. Pre-coupled beads were prepared for coupling to primary unknown antibody using the following procedure, protecting the beads from light. Individual tubes were used for each unknown supernatant. The volume of supernatant needed was calculated using the following formula: (n×2+10)×50 μl (where n=total number of samples). A concentration of 0.1 μg/ml was used in this assay. The bead stock was gently vortexed, and diluted in supernatant to a concentration of 2500 of each bead in 50 μl per well or $0.5 \times 10^5$ beads/ml.

Samples were incubated on a shaker in the dark at room temperature overnight.

The filter plate was pre-wetted by adding 200 μl wash buffer per well, which was then aspirated. 50 μl of each bead was added to each well of the filter plate. Samples were washed once by adding 100 μl/well wash buffer and aspirating. Antigen and controls were added to the filter plate at 50 μl/well. The plate was covered, incubated in the dark for 1 hour on a shaker, and then samples were washed 3 times. A secondary unknown antibody was then added at 50 μl/well. A concentration of 0.1 μg/ml was used for the primary antibody. The plate was then incubated in the dark for 2 hours at room temperature on a shaker, and then samples were washed 3 times. 50 μl/well of biotinylated mouse anti-human IgG (Pharmingen #555785) diluted at 1:500 was added, and samples were incubated in the dark for 1 hour with shaking at room temperature.

Samples were washed 3 times. 50 μl/well Streptavidin-PE at a 1:1000 dilution was added, and samples were incubated in the dark for 15 minutes with shaking at room temperature. After running two wash cycles on the Luminex100, samples were washed 3 times. Contents in each well were resuspended in 80 μl blocking buffer. Samples were carefully mixed with pipetting several times to resuspend the beads. Samples were then analyzed on the Luminex100. Results are presented below in Table 10.

Example 11

Structural Analysis of Anti-IGF-I/II Antibodies

The variable heavy chains and the variable light chains of several antibodies were sequenced to determine their DNA sequences. The complete sequence information for the anti-IGF-I/II antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations.

The alignment of the sequences of these antibodies to their germline genes are shown in the following tables. Table 11 is a table comparing the antibody heavy chain regions to their cognate germ line heavy chain region. Table 12 is a table comparing the antibody kappa light chain regions to their cognate germ line light chain region. Identity is shown as "-" and mutations away from germline are shown as the new amino acid.

The variable (V) regions of immunoglobulin chains are encoded by multiple germ line DNA segments, which are joined into functional variable regions ($V_H DJ_H$ or $V_K J_K$) during B-cell ontogeny. The molecular and genetic diversity of the antibody response to IGF-I/II was studied in detail. These assays revealed several points specific to anti-IGF-I/II antibodies.

Analysis of five individual antibodies specific to IGF-I/II resulted in the determination that the antibodies were derived from three different germline VH genes, four of them from the VH4 family, with 2 antibodies being derived from the VH4-39 gene segment. Tables 11 and 12 show the results of this analysis.

It should be appreciated that amino acid sequences among the sister clones collected from each hybridoma are identical.

TABLE 10

BINS FOR TOP 34 IGF-I/II ANTIBODIES POSITIVE IN FUNCTIONAL ASSAY

| IGF-I Bin 1 | Bin 2 | Bin 3 | No Bin | IGF-II Bin 1 | Bin 2 | Bin 3 | No Bin |
|---|---|---|---|---|---|---|---|
| 7.3.3 | 7.58.3 | 7.175.2 | 7.215.2 | 7.3.3 | 7.158.2 | 7.175.2 | 7.215.2 |
| 7.23.3 | 8.287.2 | 7.85.2 | | 7.127.1 | 8.146.2 | 4.90.2 | |
| 7.66.1 | | 4.90.2 | | 7.99.1 | 7.252.1 | 4.141.1 | |
| 7.56.3 | | 4.141.1 | | 7.123.1 | 8.86.1 | 7.85.2 | |
| 7.160.2 | | 7.146.3 | | 7.212.1 | | 7.251.3 | |
| 7.41.3 | | 7.34.1 | | 7.234.2 | | 7.159.2 | |
| 4.121.1 | | 7.159.2 | | 7.130.1 | | 7.146.3 | |
| 8.146.2 | | 7.251.3 | | 7.118.1 | | 7.34.1 | |
| 7.252.1 | | | | 8.287.2 | | | |
| 7.123.1 | | | | 7.58.3 | | | |
| 7.212.1 | | | | 7.66.1 | | | |
| 7.234.2 | | | | 7.41.3 | | | |
| 7.99.1 | | | | 7.56.3 | | | |
| 7.127.1 | | | | 7.160.2 | | | |
| 4.25.1 | | | | 7.202.3 | | | |
| 8.8.3 | | | | 8.8.3 | | | |
| 7.158.2 | | | | 4.25.1 | | | |
| 7.202.3 | | | | 7.23.3 | | | |
| 7.130.1 | | | | 4.142.2 | | | |
| 8.86.1 | | | | 4.143.2 | | | |
| 4.142.2 | | | | 4.121.1 | | | |
| 7.118.1 | | | | | | | |
| 4.143.2 | | | | | | | |

For example, the heavy chain and light chain sequences for mAb 7.159.2 are identical to the sequences shown in Tables 11 and 12 for mAb 7.159.1.

The heavy chain CDR1s of the antibodies of the invention have a sequence as disclosed in Table 11. The CDR1s disclosed in Table 11 are of the Kabat definition. Alternatively, the CDR1s can be defined using an alternative definition so as to include the last five residues of the FR1 sequence. For example, for antibody 7.159.1 the FR1 sequence is QVQLVQSGAEVKKPGASVKVSCKAS (SEQ ID NO.: 93) and the CDR1 sequence is GYTFTSYDIN (SEQ ID NO.: 94); for antibody 7.158.1 the FR1 sequence is QLQLQESGPGLVKPSETLSLTCTVS (SEQ ID NO.: 95) and the CDR1 sequence is GGSIRSSSYYWG (SEQ ID NO.: 96); for antibody 7.234.1 the FR1 sequence is QLQLQESGPGLVKPSETLSLTCTVS (SEQ ID NO.: 97) and the CDR1 sequence is GGSINSSSNYWG (SEQ ID NO.: 98); for antibody 7.34.1 the FR1 sequence is QVQLQESGPGLVKPSETLSLTCTVS (SEQ ID NO.: 99) and the CDR1 sequence is GGSISSYYWS (SEQ ID NO.: 100); and for antibody 7.251.3 the FR1 sequence is QVQLQESGPGLVKPSETLSLTCTVS (SEQ ID NO.: 101) and the CDR1 sequence is GGSISSYYWS (SEQ ID NO.: 102).

It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 12 shows that the light chain sequence of mAb 7.34.1 (SEQ ID NO.: 12) differs from the corresponding germline sequence (SEQ ID NO.:80) through a Pro to Ala mutation (mutation 1) in the FR1 region, and via a Phe to Leu mutation (mutation 2) in the FR2 region. Thus, the amino acid or nucleotide sequence encoding the light chain of mAb 7.34.1 can be modified to change mutation 1 to yield the germline sequence at the site of mutation 1. Further, the amino acid or nucleotide sequence encoding the light chain of mAb 7.34.1 can be modified to change mutation 2 to yield the germline sequence at the site of mutation 2. Still further, the amino acid or nucleotide sequence encoding the light chain of mAb 7.34.1 can be modified to change both mutation 1 and mutation 2 to yield the germline sequence at the sites of both mutations 1 and 2.

TABLE 11

HEAVY CHAIN ANALYSIS

| Chain Name | SEQ ID NO. | V | D | J | FR1 | CDR1 | FR2 |
|---|---|---|---|---|---|---|---|
| Germline | 75 | VH1-8 | N.A. | JH6B | QVQLVQSGAEVKKPGASVKVSCKASGYTFT | SYDIN | WVRQATGQGLEWMG |
| 7_159_1 | 6 | " | " | " | QVQLVQSGAEVKKPGASVKVSCKASGYTFT | SYDIN | WVRQATGQGLEWMG |
| Germline | 77 | VH4-39 | D6-19 | JH2 | QLQLQESGPGLVKPSETLSLTCTVSGGSIS | SSSYYWG | WIRQPPGKGLEWIG |
| 7_158_1 | 2 | " | " | " | QLQLQESGPGLVKPSETLSLTCTVSGGSIR | SSSYYWG | WIRQPPGKGLEWIG |
| 7_234_1 | 18 | " | " | " | QLQLQESGPGLVKPSETLSLTCTVSGGSIN | SSSNYWG | WIRQPPGKGLAWIG |
| Germline | 79 | VH4-59 | D1-20 | JH6B | QVQLQESGPGLVKPSETLSLTCTVSGGSIS | SYYWS | WIRQPPGKGLEWIG |
| 7_34_1 | 10 | " | " | " | QVQLQESGPGLVKPSETLSLTCTVSGGSIS | SYYWS | WIRQPPGRGLEWIG |
| 7_251_3 | 14 | " | " | " | QVQLQESGPGLVKPSETLSLTCTVSGGSIS | SYYWS | WIRQPPGKGLEWIG |

| Chain Name | CDR2 | FR3 | CDR3 | FR4 |
|---|---|---|---|---|
| Germline | WMNPNSGNTGYAQKFQG | RVTMTRNTSISTAYMELSSLRSEDTAVYYCAR | ##YYYYYGMDV | WGQGTTVTVSSA |
| 7_159_1 | WMNPNSGNTGYAQKFQG | RVTMTRNTSISTAYMELSSLRSEDTAVYYCAR | DPYYYYYGMDV | WGQGTTVTVSSA |
| Germline | SIYYSGSTYYNPSLKS | RVTISVDTSKNQFSLKLSSVTAADTAVYYCAR | ####SS##WYFDL | WGRGTLVTVSSA |
| 7_158_1 | GIYYSGSTYYNPSLKS | RVTMSVDTSKNQFSLKLSSVTAADTAVYYCAR | QRGHSSGWWYFDL | WGRGTLVTVSSA |
| 7_234_1 | GIYYSGSTYYNPSLRS | RVTMSVDTSKNQFSLKLSSVTAADTAVYYCAR | QRGHSSGWWYFDL | WGRGTLVTVSSA |
| Germline | YIYYSGSTNYNPSLKS | RVTISVDTSKNQFSLKLSSVTAADTAVYYCA#R | ITGT###GMDV | WGQGTTVTVSSA |
| 7_34_1 | YFFYSGYTNYNPSLKS | RVTMSVDTSKNQFSLKLSSVTAADTAVYYCAC | ITGTTKGGMDV | WGQGATVTVSSA |
| 7_251_3 | YFFYSGYTNYNPSLKS | RVTISVDTSKNQFSLKLSSVTAADTAVYYCAC | ITGTTKGGMDV | WGQGTTVTVSSA |

*The hatch designation (#) indicates a space in the germline and is used to show a proper alignment with the antibody sequences shown in the table.
**The germline sequences shown in the above table are for alignment purposes, and it should be realized that each individual antibody region exists in its own location within the variable regions of immunoglobulin germline DNA segments *in vivo*.

TABLE 12

LIGHT CHAIN ANALYSIS

| Chain Name | SEQ ID NO. | V | J | FR1 | CDR1 | FR2 |
|---|---|---|---|---|---|---|
| Germline | 76 | V1-19 | JL2 | QSVLTQPPSVSA APGQKVTISC | SGSSSNI GNNYVS | WYQQLPGT APKLLIY |
| 7_159_1 | 8 | " | " | QSVLTQPPSVSA APGQKVTISC | SGSSSNI ENNHVS | WYQQLPGT APKLLIY |
| Germline | 78 | L5 | JK3 | DIQMTQSPSSVS ASVGDRVTITC | RASQGIS SWLA | WYQQKPGK APKLLIY |
| 7_158_1 | 4 | " | " | DIQMTQSPSSVS ASVGDSVTITC | RASQGIS SYLA | WYQQKPGK APKLLIY |
| 7_234_1 | 20 | " | " | DIQMTQSPSSVS ASVGDRVTITC | RASRGIS SWLA | WYQQRPGK APKLLIY |
| Germline | 80 | V1-13 | JL2 | QSVLTQPPSVSG APGQRVTISC | TGSSSNI GAGYDVH | WYQQLPGT APKLLIY |
| 7_34_1 | 12 | " | " | QSVLTQAPSVSG APGQRVTISC | TGRSSNI GAGYDVH | WYQQFPGT APKLLIY |
| 7_251_3 | 16 | " | " | QSVLTQPPSVSG APGQRVTISC | TGSSSNI GAGYDVH | WYQQLPGT APKLLIY |

| Chain Name | CDR2 | FR3 | CDR3 | FR4 |
|---|---|---|---|---|
| Germline | DNNKRPS | GIPDRFSGSKSGTSAT LGITGLQTGDEADYYC | GTWDSSL SA##V | FGGGTK LTVLG |
| 7_159_1 | DNNKRPS | GIPDRFSGSKSGTSAT LGITGLQTGDEADYYC | ETWDTSL SAGRV | FGGGTK LTVLG |
| Germline | AASSLQS | GVPSRFSGSGSGTDFT LTISSLQPEDFATYYC | QQANSFP FT | FGPGTK VDIKR |
| 7_158_1 | AASSLQS | GVPSRFSGNGSGTDFT LTISSLQPEDFATYYC | QQANNFP FT | FGPGTK VDIKR |
| 7_234_1 | TASSLQS | GVPSRFSGSGSGTDFT LTISSLQPEDFATYYC | QQANSFP FT | FGPGTK VDIKR |
| Germline | GNSNRPS | GVPDRFSGSKSGTSAS LAITGLQAEDEADYYC | QSYDSSL SGSV | FGGGTK LTVLG |
| 7_34_1 | GNSNRPS | GVPDRFSGSKSGTSAS LAITGLQAEDEADYYC | QSYDSSL SGSV | FGGGTK LTVLG |
| 7_251_3 | GNNNRPS | GVPDRFSGSKSGTSAS LAITGLQADDEADYYC | QSFDSSL SGSV | FGGGTK LTVLG |

*The hatch designation (#) indicates a space in the germline and is used to show a proper alignment with the antibody sequences shown in the table.
**The germline sequences shown in the above table are for alignment purposes, and it should be realized that each individual antibody region exists in its own location within the variable regions of immunoglobulin germline DNA segments *in vivo*.

Example 12

Inhibition of IGF-I and IGF-II-Induced Phosphorylation of hIGF-IR Ectopically Expressed in NIH3T3 Cells IGF ligands exert their proliferation and anti-apoptosis functions by activating receptor tyrosine kinase activity in the IGF-IR receptor. In order to evaluate the anti IGF-I/II antibodies for their ability to inhibit IGF-induced phosphorylation of IGF-IR, NIH3T3 cells ectopically expressing hIGF-IR, were used in the following assay.

NIH3T3 cells ectopically expressing the human IGF-IR were seeded in a 96-well plate at a density of 10,000 cells per well and incubated overnight in starvation media (1% charcoal stripped FBS). The following day, the growth medium was discarded, the wells were gently washed twice with PBS, and 100 μL of serum-free medium (0% FBS) was added to starve the cells. After 1-2 hours, 100 μl of serum-free medium with 0.05% BSA containing either IGF-I (10 nM) or IGF-II (10 nM) that was pre-incubated for 60 minutes at 37° C. with various antibody concentrations, was added to the cells in triplicate. The stimulation was allowed to occur for 10 minutes at 37° C., after stimulation, media removed and 100 uL 3.7% fromaldehyde in PBS/3% BSA added to each well and incubated at RT for 20 min. The cells were then washed 2× with PBS and 100 uL permeabilization buffer (0.1% Triton-X in 3% BSA/PBS) was added to each well. This was allowed to incubate at RT for 10 min, discarded and 100 ul of 0.6% hydrogen peroxide in PBS/3% BSA was added to inactivate any endogenous peroxidase activity. After a 20 min RT incubation, the cells were washed 3× with PBS/0.1% Tween-20 and blocked by adding 100 uL 10% FBS in PBS/0.1% Tween-20 at RT for 1 hr. The Blocking Buffer was then removed and 50 uL anti-phospho IGFIR antibody at 1 ug/ml (cat#44-804, BioSource) was added to each well in 10% FBS/PBS-T. After a 2 hr RT incubation cells were washed 3× with PBST soaking for 5 minutes between each wash. After the washes 50 ul/well of a Goat anti Rabbit IgGFc-HRP secondary antibody diluted 1:250 in Blocking Buffer was added to each of the well. After a 1 hour RT incubation the cells were washed 3× for 5 minutes with PBST as before and tapped dry. 50 ul of ECL reagent (DuoLux) was then added and RLUs was read immediately.

Thirty-two (32) antibody lines were screened, and two independent assays were performed for each antigen. The results for the top ten antibodies are summarized in Table 13 below.

TABLE 13

SUMMARY OF INHIBITION OF IGF-DEPENDENT IGF-IR PHOSPHORYLATION IN NIH3T3 CELLS

| | IGF-I pTYR Results (n = 2) | | | | IGF-II pTYR Results (n = 2) | | | |
|---|---|---|---|---|---|---|---|---|
| | % MAX Activation | | EC50 (nM)* | | % MAX Activation | | EC50 (nM)* | |
| mAb ID | Mean | SD | Mean | SD | Mean | SD | Mean | SD |
| 7.159.2 | 16.5% | 6.6% | 7.4 | 0.8 | 28.6% | 5.4% | 3.1 | 0.2 |
| 7.34.1 | 14.2% | 1.8% | 9.4 | 0.8 | 21.5% | 3.9% | 2.5 | 0.1 |

TABLE 13-continued

SUMMARY OF INHIBITION OF IGF-DEPENDENT IGF-IR PHOSPHORYLATION IN NIH3T3 CELLS

| | IGF-I pTYR Results (n = 2) | | | | IGF-II pTYR Results (n = 2) | | | |
|---|---|---|---|---|---|---|---|---|
| | % MAX Activation | | EC50 (nM)* | | % MAX Activation | | EC50 (nM)* | |
| mAb ID | Mean | SD | Mean | SD | Mean | SD | Mean | SD |
| 7.146.3 | 19.5% | 3.9% | 19.0 | 5.7 | 23.6% | 2.1% | 3.6 | 0.2 |
| 7.251.3 | 16.9% | 5.4% | 14.5 | 0.7 | 15.9% | 1.5% | 3.0 | 0.9 |
| 7.234.2 | 21.1% | 3.0% | 24.3 | 1.0 | 21.1% | 0.1% | 7.7 | 0.1 |
| 7.160.2 | 33.6% | 6.4% | 22.9 | 0.1 | 21.5% | 0.6% | 4.7 | 0.2 |
| 7.158.2 | 22.7% | 0.9% | 28.3 | 0.5 | 33.7% | 2.4% | 11.3 | 3.2 |
| 7.56.3 | 31.3% | 2.2% | 25.1 | 4.3 | 21.2% | 0.2% | 6.3 | 0.5 |
| 7.118.1 | 24.1% | 5.2% | 40.8 | 2.6 | 21.8% | 3.2% | 13.9 | 5.3 |
| 7.41.3 | 33.1% | 6.1% | 47.1 | 7.0 | 29.5% | 4.4% | 3.5 | 4.0 |

*These assays may have been run under antigen limiting conditions given the mAb KD for IGF-I and IGF-II.

Example 13

Inhibition of IGF-I and IGF-II-Induced Proliferation of NIH3T3 Cells Transfected with HIGF-IR As discussed above, one of the criteria for neutralizing IGF-I/II antibodies is the ability to inhibit IGF-induced proliferation. In order to evaluate the antibodies for their ability to inhibit IGF-induced proliferation, NIH3T3 cells ectopically expressing hIGF-IR, were used in the following assay.

NIH3T3 cells ectopically expressing hIGF-IR were seeded in a 96-well plate at a density of 5000 cells per well and cultured overnight in starvation medium (1% charcoal stripped FBS). The following day, the growth medium was discarded, the wells were gently washed twice in medium without serum, and 100 µL of serum-free medium was added to starve the cells. 100 µL of starvation media containing 15 ng/ml IGFI or 50 ng/ml IGFII pre-incubated for 30 min at 37° C. with various antibody concentrations was added to the cells in duplicate or triplicate. Following a 20 hr incubation cells are pulsed with BrdU for 2 hrs and the degree of incorporation (proliferation) was quantitated using the Cell Proliferation ELISA kit from Roche (Roche, Cat#1 647 229).

A total of 32 antibody lines were screened, and two or three independent assays were performed for each antigen. The results for the top 10 antibodies are summarized in Table 14 below.

TABLE 14

SUMMARY OF INHIBITION OF IGF-DEPENDENT PROLIFERATION OF NIH3T3/hIGF-IR CELLS

| | IGF-I Proliferation Assay | | | | IGF-II Proliferation Assay | | | |
|---|---|---|---|---|---|---|---|---|
| | % Inhibition | | EC50 (nM)* | | % Inhibition | | EC50 (nM)* | |
| mAb ID | Mean (n = 3) | SD | Mean (n = 3) | SD | Mean (n = 2) | SD | Mean (n = 2) | SD |
| 7.159.2 | 77.0% | 9.6% | 24.1 | 5.9 | 99.3% | 0.6% | 7.6 | 2.5 |
| 7.34.1 | 72.6% | 5.6% | 23.4 | 8.1 | 73.6% | 11.8% | 16.3 | 0.4 |
| 7.146.3 | 65.3% | 5.5% | 37.2 | 4.5 | 82.0% | 6.9% | 15.9 | 3.4 |
| 7.251.3 | 72.4% | 15.3% | 38.9 | 4.3 | 79.2% | 7.8% | 22.0 | 3.7 |
| 7.234.2 | 67.3% | 6.9% | 40.6 | 4.6 | 62.1% | 17.2% | 24.3 | 2.4 |
| 7.160.2 | 62.8% | 5.7% | 47.6 | 10.7 | 45.9% | 0.8% | 24.7 | 2.8 |
| 7.158.2 | 57.4% | 19.5% | 42.8 | 1.7 | 54.6% | 6.6% | 36.0 | 4.2 |
| 7.56.3 | 50.2% | 7.8% | 65.7 | 31.9 | 48.0% | 10.9% | 38.3 | 7.5 |
| 7.118.1 | 59.4% | 14.5% | 1626.6 | 2714.5 | 68.3% | 0.8% | 49.9 | 3.8 |
| 7.41.3 | 29.5% | 14.7% | 76.3 | 35.9 | 51.9% | 13.7% | 61.9 | 23.7 |

*These assays may have been run under antigen limiting conditions given the mAb KD for IGF-I and IGF-II.

Example 14

Inhibition of IGF-I and IGF-II-Induced Phosphorylation of hIGF-IR Expressed in BxPC3 Human Pancreatic Tumor Cells IGF-I/II exert their proliferation and anti-apoptosis functions by activating receptor tyrosine kinase activity in the IGF-IR receptor. In order to evaluate the antibodies for their ability to inhibit IGF-induced phosphorylation of IGF-IR, BxPC3 human pancreatic tumor cells, which express endogenous hIGF-IR, were used in the following assay.

BxPC3 cells were seeded in a 96-well plate at a density of 55,000 cells per well and incubated overnight in regular growth medium. The following day, the growth medium was discarded, the wells were gently washed twice in medium without serum, and 100 µL of serum-free medium was added to starve the cells. After 24 hours, the medium was discarded, and the cells were gently washed once in medium without serum. Serum-free medium with 0.05% BSA containing either IGF-I (20 ng/ml) or IGF-II (75 ng/ml) was pre-incubated for 30 minutes at 37° C. with various antibody concentrations, and 100 µL was then added to the cells in triplicate. The plates were incubated for 15 minutes at 37° C., and were subsequently rinsed with cold PBS. 100 µL of lysis buffer was added to the wells and the plates were incubated for 30 minutes at 4° C. The lysates were spun down at 2000 rpm for 10 minutes at 4° C., and the supernatant was collected. IGF-IR phosphorylation was quantitated using the Duoset human phosphor-IGF-IR ELISA kit (R&D Systems, Cat. No. DYC1770).

Ten antibody lines were screened, and two independent assays were performed for each antigen. The results are summarized in Table 15 below.

TABLE 15

SUMMARY OF INHIBITION OF IGF-DEPENDENT IGF-IR PHOSPHORYLATION

| | IGF-I pTYR Results (n = 2) | | | | IGF-II pTYR Results (n = 2) | | | |
|---|---|---|---|---|---|---|---|---|
| | n = 1 | | n = 2 | | n = 1 | | n = 2 | |
| mAb ID | Max % Inhibition (333.3 nM) | EC50 (nM) | Max % Inhibition (333.3 nM) | EC50 (nM) | Max % Inhibition (333.3 nM) | EC50 (nM) | *Max % Inhibition (133.3 nM) | EC50 (nM) |
| 7.159.2 | 100.0 | 3.3 | 100.0 | 1.6 | 100.0 | 1.6 | 91.2 | 1.7 |
| 7.34.1 | 100.0 | 5.9 | 98.5 | 3.8 | 100.0 | 2.0 | 89.7 | 1.9 |
| 7.146.3 | 96.4 | 16.1 | 94.2 | 10.7 | 100.0 | 2.0 | 87.9 | 2.0 |
| 7.251.3 | 95.7 | 7.5 | 95.2 | 5.3 | 100.0 | N.D. | 91.3 | 2.6 |
| 7.234.2 | 97.3 | 5.1 | 91.5 | 2.9 | 98.5 | 1.9 | 77.3 | 2.3 |
| 7.160.2 | 93.4 | 5.3 | 89.2 | 3.1 | 88.6 | 1.7 | 73.2 | 2.5 |
| 7.158.2 | 92.9 | 4.5 | 89.4 | 3.6 | 92.4 | N.D. | 74.0 | 4.2 |
| 7.56.3 | 84.9 | N.D. | 88.7 | 6.5 | 91.4 | 10.1 | 66.2 | 5.1 |
| 7.118.1 | 90.5 | 13.1 | 90.6 | 11.8 | 95.7 | 17.9 | 78.0 | 13.1 |
| 7.41.3 | 88.6 | 6.5 | 86.5 | 6.5 | 88.6 | 4.5 | 70.6 | 3.1 |

*333 nM for the last 3 antibodies.
N.D.: Not Determined

Example 15

Inhibition of IGF-I and IGF-II-Induced Proliferation of BxPC3 Human Pancreatic Tumor Cells As discussed above, one of the criteria for neutralizing IGF antibodies is the ability to inhibit IGF-induced proliferation. In order to evaluate the antibodies for their ability to inhibit IGF-induced proliferation, BxPC3 human pancreatic tumor cells, which express endogenous hIGF-IR, were used in the following assay.

BxPC3 cells were seeded in a 96-well plate at a density of 2000 cells per well and cultured overnight in regular growth medium. The following day, the growth medium was discarded, the wells were gently washed twice in medium without serum, and 100 μL of serum-free medium with 10 μg/ml transferrin and 0.1% BSA (assay medium) was added to starve the cells. After 24 hours, the medium was discarded, the cells were gently washed once in medium without serum, and 100 μL of assay medium containing 20 ng/ml IGF pre-incubated for 30 min at 37° C. with various antibody concentrations was added to the cells in duplicate or triplicate. The plates were incubated for 3 days, and proliferation was quantitated using the CellTiter-Glo reagent (Promega).

Ten antibody lines were screened, and two or three independent assays were performed for each antigen. The results are summarized in Table 16 below. Based on the functional data below and the data from the Example 14, the four best antibodies were selected. IGF-I-induced proliferation assay data.was excluded from the selection criteria because of the high assay variability observed.

TABLE 16

SUMMARY OF INHIBITION OF IGF-DEPENDENT PROLIFERATION OF BxPC3 HUMAN PANCREATIC TUMOR CELLS

| | IGF-II Proliferation Results (n = 2) | | | |
|---|---|---|---|---|
| | n = 1 | | n = 2 | |
| MAb ID | Max % Inhibition (333.3 nM) | EC50 (nM) | *Max % Inhibition (133.3 nM) | EC50 (nM) |
| 7.159.2 | 120.0 | 0.8 | 118.3 | 0.9 |
| 7.34.1 | 117.0 | 0.5 | 109.0 | 6.7 |
| 7.146.3 | 128.7 | 3.0 | 119.5 | 7.3 |

TABLE 16-continued

SUMMARY OF INHIBITION OF IGF-DEPENDENT PROLIFERATION OF BxPC3 HUMAN PANCREATIC TUMOR CELLS

| | IGF-II Proliferation Results (n = 2) | | | |
|---|---|---|---|---|
| | n = 1 | | n = 2 | |
| MAb ID | Max % Inhibition (333.3 nM) | EC50 (nM) | *Max % Inhibition (133.3 nM) | EC50 (nM) |
| 7.251.3 | 128.5 | 0.5 | 105.3 | 4.4 |
| 7.234.2 | 111.7 | N.D. | 200.7 | 2.6 |
| 7.160.2 | 79.7 | 1.1 | 155.7 | N.D. |
| 7.158.2 | 86.3 | 0.0013 | 148.3 | N.D. |
| 7.56.3 | 87.0 | N.D. | 112.3 | 102.0 |
| 7.118.1 | 114.0 | 34.0 | 137.0 | 54.7 |
| 7.41.3 | 102.0 | N.D. | 73.0 | N.D. |

*333 nM for the last 3 antibodies
N.D.: Not Determined

Example 16

Determination of Cross-Reactivity with Mouse IGF-I, IGF-II and Insulin

One objective was to develop antibodies that were specific to IGF-I and IGF-II but that have no cross-reactivity with insulin. In order to perform later experiments in animals, the antibodies should also cross-react with murine IGF-I/II but not murine insulin. Accordingly, ELISA assays were performed to determine whether selected antibodies were able to cross-react with murine IGFs or insulin.

As shown in Table 17, five of the top ten antibodies were tested for cross-reactivity with mouse or rat insulin by ELISA. The ELISAs showed that these antibodies had no cross-reactivity with mouse or rat insulin, compared to negative control antibody PK16.3.1 and in contrast to positive control anti-rat insulin antibody.

TABLE 17

CROSS-REACTIVITY WITH MOUSE INSULIN

| | OD 450 with different Ag | | |
|---|---|---|---|
| Antibodies | mouse Insulin | Rat Insulin | No Ag |
| 7.159.2 | 0.52 | 0.52 | 0.56 |
| 7.160.2 | 0.60 | 0.57 | 0.62 |
| 7.34.1 | 0.48 | 0.47 | 0.55 |
| 7.251.3 | 0.55 | 0.53 | 0.56 |
| 7.234.2 | 0.51 | 0.49 | 0.66 |
| Serum | 1.28 | 1.23 | 1.34 |
| anti Rat Insulin | 2.52 | 3.06 | 0.10 |
| PK16.3.1 | 0.58 | 0.58 | 0.62 |

TABLE 18

| INHIBITION OF MOUSE IGF-INDUCED PHOSPFIORYLATION OF hIGF-IR | | | | |
|---|---|---|---|---|
| | Mouse IGF-I EC50 (nM) | | Mouse IGF-II EC50 (nM) | |
| mAb ID | n = 1 | n = 2 | n = 1 | n = 2 |
| 7.159.2 | 2.8 | 5.7 | 3.1 | 5.0 |
| 7.34.1 | 6.0 | 10.2 | 4.0 | 9.7 |
| 7.251.3 | 6.7 | 10.6 | 5.4 | 8.7 |
| 7.234.2 | 46.0 | | 36.1 | |
| 7.160.2 | 49.5 | | 225.2 | |

Example 17

Inhibition of Mouse IGF-I and IGF-II-Induced Phosphorylation of Human IGF-IR Ectopically Expressed in NIH3T3 Cells The monoclonal antibodies with cross-reactivity with mouse IGF-I and IGF-II were further tested in order to determine the extent they inhibit IGF-induced phosphorylation of the IGF-IR. This assay was performed as previously described using NIH3T3 cells ectopically expressing the hIGF-IR receptor. The results of this assay are summarized in Table 18.

NIH3T3 cells ectopically expressing the human IGF-IR were seeded in a 96-well plate at a density of 10,000 cells per well and incubated overnight in starvation media (1% charcoal stripped FBS). The following day, the growth medium was discarded, the wells were gently washed twice with PBS, and 100 µL of serum-free medium (0% FBS) was added to starve the cells. After 1-2 hours, 100 ul of serum-free medium with 0.05% BSA containing either mouse IGF-I (10 nm) or IGF-II (20 nM) (R&D Systems, Inc., Minneapolis, Minn. Cat. No. 791-MG and 792-MG respectively) that was pre-incubated for 60 minutes at 37° C. with various antibody concentrations, was added to the cells in triplicate. The stimulation was allowed to occur for 10 minutes at 37° C., after stimulation, media removed and 100 uL 3.7% formaldehyde in PBS/3% BSA added to each well and incubated at RT for 20 min. The cells were then washed 2× with PBS and 100 uL permeabilization buffer (0.1% Triton-X in 3% BSA/PBS) was added to each well. This was allowed to incubate at RT for 10 min, discarded and 100 ul of 0.6% hydrogen peroxide in PBS/3% BSA was added to inactivate any endogenous peroxidase activity. After a 20 min RT incubation, the cells were washed 3× with PBS/0.1% Tween-20 and blocked by adding 100 uL 10% FBS in PBS/0.1% Tween-20 at RT for 1 hr. The Blocking Buffer was then removed and 50 uL anti-phospho IGFIR antibody at 1 ug/ml (cat#44-804, BioSource) was added to each well in 10% FBS/PBS-T. After a 2 hr RT incubation cells were washed 3× with PBST soaking for 5 minutes between each wash. After the washes 50 ul/well of a Goat anti Rabbit IgGFc-HRP secondary antibody diluted 1:250 in Blocking Buffer was added to each of the well. After a 1 hour RT incubation the cells were washed 3× for 5 minutes with PBST as before and tapped dry. 50 ul of ECL reagent (DuoLux) was then added and RLUs was read immediately.

Example 18

Inhibition of the Growth of NIH3T3 Cells Expressing IGF-II and IGF-1R In Vivo in Nude Mice In order to evaluate the antibodies for their ability to inhibit IGF-II-induced proliferation in vivo, the following experiments were performed.

Female nude mice 6-8 weeks of age (supplied by Charles River Laboratories, Wilmington, Mass., USA) were implanted subcutaneously with $5 \times 10^6$ Clone 32 cells (NIH3T3 cells ectopically overexpressing human IGF-II and human IGF-1R). The cells were suspended in PBS in a total inoculum volume of 330 µl. The tumors were allowed to grow to 100-200 $mm^3$ prior to treatment with monoclonal antibodies 7.159.2, 7.34.1 and 7.251.3. Antibodies or IgG2 isotype control antibody suspended in PBS were administered intraperitoneally to randomized groups of 9 or 12 mice weekly for 4 weeks at 5 or 50 mg/kg from Day 22. PBS was administered as a vehicle control to a further group of 11 mice weekly for 4 weeks from Day 22. Tumor size and body weight was measured 2-3 times per week. The results are summarized in FIGS. 1 and 2.

Figure 2:
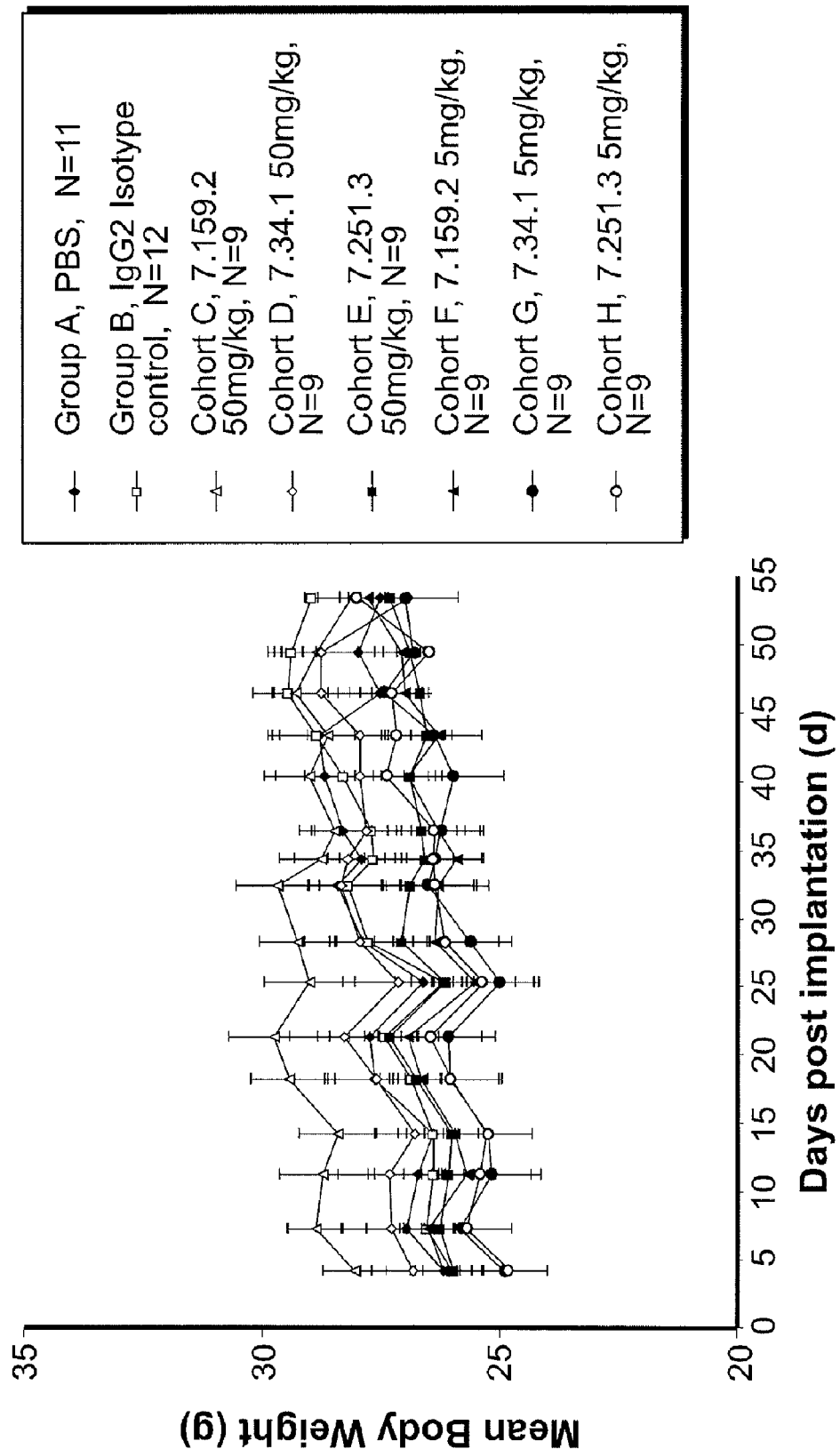
FIG. 2 is a graph showing body weight in Clone 32 xenograft mice treated with mAbs 7.159.2, 7.34.1, 7.251.3 compared to IgG2 and PBS controls. Mean body weight is shown on the y-axis and time after implantation is shown on the x-axis.

Significant tumor growth inhibition was observed (see FIG. 1) with no significant weight loss occurring in any group (see FIG. 2). Antibodies 7.159.2, 7.34.1 and 7.251.3 significantly inhibited the growth of Clone 32 tumors at 5 and 50 mg/kg/week (see FIG. 1).

Example 19

Inhibition of the Growth of NIH3T3 Cells Expressing IGF-I and IGF-1R In Vivo in Nude Mice In the previous example, the antibodies were shown to inhibit IGF-II-induced proliferation in vivo. In order to evaluate the antibodies for their ability to inhibit IGF-I-induced proliferation in vivo, the following experiments were performed.

Female nude mice (Alderley Park strain derived from Swiss nu/nu mice strain, supplied by AstraZeneca) were implanted with $5 \times 10^6$ viable P12 cells [NIH3T3 cells ectopically overexpressing human IGF-I and human IGF-1R (Pietrzkowski et al, Cell Growth & Differentiation, 3, 199-205, 1992)] subcutaneously in the left flank. The cells were suspended in PBS in a total inoculum volume of 0.1 ml. Two groups of animals (each n=10) were dosed twice weekly from day of NIH3T3 cell implant with either mAb 7.159.2 at 1.0 mg per mouse or with an equivalent volume of PBS vehicle (0.3 ml) for the same schedule. All doses were given intraperitoneally via the (i.p.) route. Animal body weights were measured daily and, once established, tumor measurements were taken twice weekly using calipers. The volume for all measurable tumors was calculated from the caliper measurements assuming an ovoid shape. The results are summarized in FIG. 3.

Figure 3:
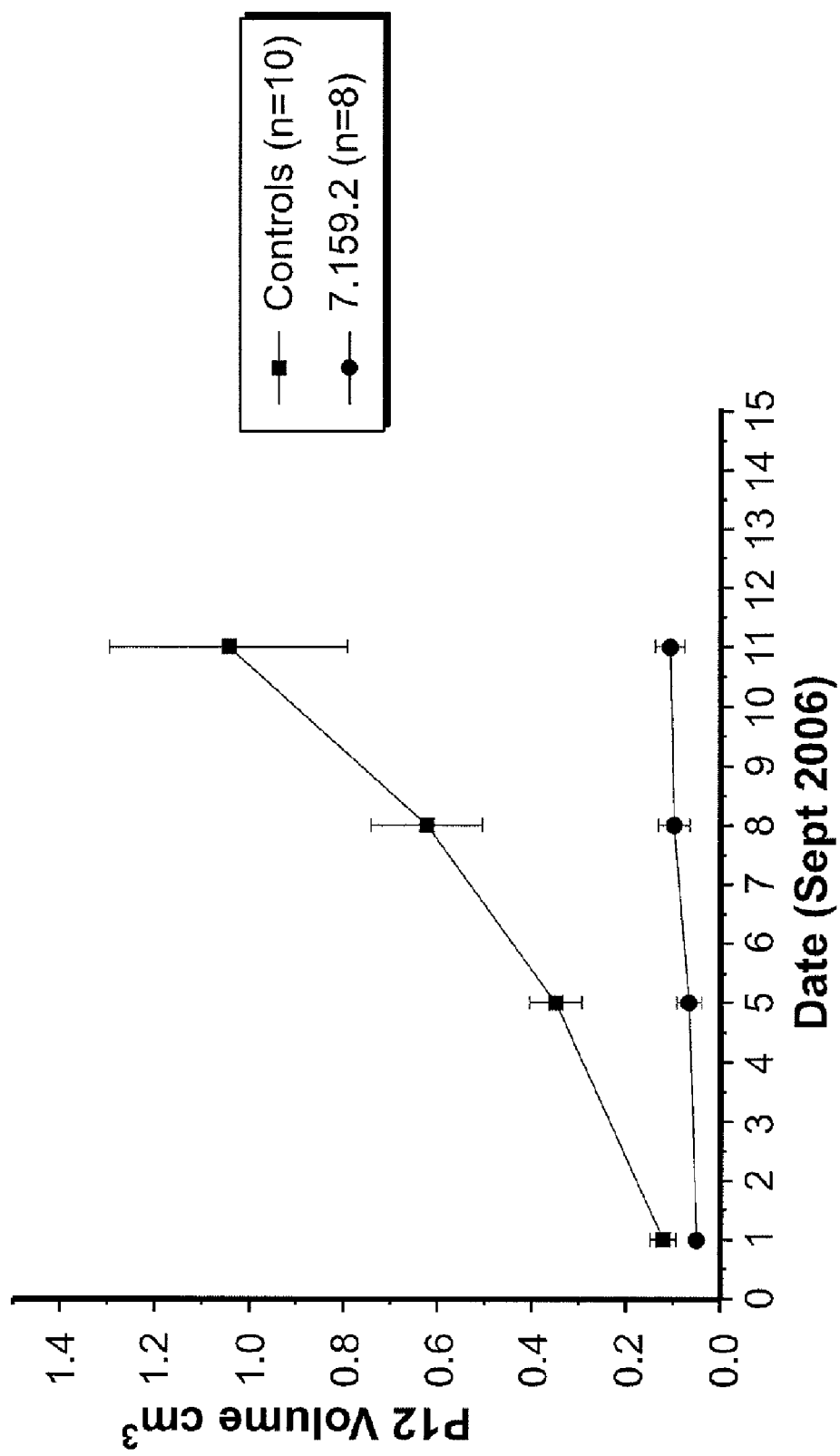
FIG. 3 is a graph showing inhibition of xenograft tumor growth in nude mice of NIH3T3 cells expressing IGF-I and IGF-IR (P12 cells) with mAb 7.159.2 compared to PBS control. Mean tumor volume is shown on the y-axis and time after implantation (indicated by date) is shown on the x-axis.

As shown in FIG. 3, significant tumor growth inhibition was observed with mAb 7.159.2 following twice weekly i.p. administration of 1.0 mg antibody/mouse. No significant weight loss was observed in any of the groups of animals.

Example 20

Inhibition of Tumor Cell Growth in Human Patients

A group of human cancer patients diagnosed with pancreatic cancer is randomized into treatment groups. Each patient group is treated with weekly intravenous injections of mAb 7.159.2, 7.34.1 or 7.251.3 described herein. Each patient is dosed with an effective amount of the antibody ranging from 50 mg/kg to 2,250 mg/kg for 4-8 weeks. A control group is given only the standard chemotherapeutic regimen.

At periodic times during and after the treatment regimen, tumor burden is assessed by magnetic resonance imaging (MRI). It is found that the patients who have received weekly antibody treatment with mAb 7.159.2, 7.34.1 or 7.251.3 show significant reductions in tumor size, compared to patients that do not receive antibody treatment. In some treated patients, the tumors are no longer detectable. In contrast, tumor size increases or remains substantially the same in the control group.

Example 21

Inhibition of Tumor Cell Growth in a Human Patient

A human patient is diagnosed with a malignant tumor. The patient is treated with weekly intravenous injections of mAb 7.159.2 for 8 weeks. At periodic times during and after the treatment regimen, tumor burden is assessed by magnetic resonance imaging (MRI). Significant reductions in tumor size are found.

Example 22

Treatment of Acromegaly in a Human Patient

An adult male is diagnosed with acromegaly. The patient is treated with bi-weekly intravenous injections of mAb 7.34.1 over a period of 2 years. As a result, the patient experiences a significant reduction in the symptoms of acromegaly.

Example 23

Treatment of Psoriasis in a Human Patient

An adult female is diagnosed with severe psoriasis. The patient is treated with bi-weekly intravenous injections of mAb 7.251.3 over a period of 3 weeks. As a result, the patient experiences a significant reduction in the symptoms of psoriasis.

Example 24

Treatment of Osteoporosis in a Human Patient

An adult female is diagnosed with osteoporosis. The patient is treated with bi-weekly intravenous injections of mAb 7.159.2 over a period of a year. As a result, there is a significant reduction in loss of bone density.

Example 25

Treatment of Atherosclerosis in a Human Patient

An adult male is diagnosed with atherosclerosis. The patient is treated with bi-weekly intravenous injections of mAb 7.34.1 over a period of a year. As a result, the patient experiences a reduction in the symptoms of atherosclerosis, such as angina pectoris.

Example 26

Treatment of Restenosis in a Human Patient

An adult male receives angioplasty to relieve a blocked artery. Following the angioplasty procedure, the patient is treated with bi-weekly intravenous injections of mAb 7.251.3 over a period of a year. As a result, the patient does not experience restenosis of the treated artery.

Example 27

Treatment of Diabetes in a Human Patient

An adult female is diagnosed with diabetes. The patient is treated with bi-weekly intravenous injections of mAb 7.159.2 over a period of a year. As a result, the symptoms of diabetes are reduced.

Sequences

The sub-cloned hybridomas were sequenced to determine their primary structure at both the nucleotide and amino acid level for both the variable heavy and the variable light chain genes. The nucleotide and polypeptide sequences of the variable regions of the monoclonal antibodies against IGF-I and IGF-II, as listed in Table 1, are provided in the Sequence Listing.

Incorporation by Reference

All references cited herein, including patents, patent applications, papers, text books, and the like, and the references cited therein, to the extent that they are not already, are hereby incorporated herein by reference in their entirety.

Equivalents

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. An isolated antibody, or binding fragment thereof, that preferentially binds to insulin-like growth factor-II (IGF-II) with cross-reactivity to insulin-like growth factor I (IGF-I), wherein said antibody has the amino acid sequence of the antibody produced by hybridoma cell line 7.159.2 (ATCC Accession Number PTA-7424).

2. An isolated antibody, or binding fragment thereof, that preferentially binds to insulin-like growth factor-II (IGF-II) with cross-reactivity to insulin-like growth factor I (IGF-I), wherein said antibody comprises a heavy chain polypeptide comprising the sequence of SEQ ID NO.: 6 and a light chain polypeptide.

3. The antibody of claim 2, wherein the light chain polypeptide comprises the sequence of SEQ ID NO.: 8.

4. The antibody of claim 1 or claim 2, wherein said antibody does not bind specifically to IGF-II or IGF-I proteins when said proteins are bound to Insulin Growth Factor Binding Protein-3.

5. An isolated antibody, or binding fragment thereof, that preferentially binds to insulin-like growth factor-II (IGF-II) with cross-reactivity to insulin-like growth factor I (IGF-I), wherein said antibody comprises:

a heavy chain complementarity determining region 1 (CDR1) comprising the amino acid sequence of "Ser Tyr Asp Ile Asn" (SEQ ID NO: 33);

a heavy chain complementarity determining region 2 (CDR2) comprising the amino acid sequence of "Trp Met Asn Pro Asn Ser Gly Asn Thr Gly Tyr Ala Gln Lys Phe Gln Gly" (SEQ ID NO: 34);

a heavy chain complementarity determining region 3 (CDR3) comprising the amino acid sequence of "Asp Pro Tyr Tyr Tyr Tyr Tyr Gly Met Asp Val" (SEQ ID NO: 35);

a light chain complementarity determining region 1 (CDR1) comprising the amino acid sequence of "Ser Gly Ser Ser Ser Asn Ile Glu Asn Asn His Val Ser" (SEQ ID NO: 36);

a light chain complementarity determining region 2 (CDR2) comprising the amino acid sequence of "Asp Asn Asn Lys Arg Pro Ser" (SEQ ID NO: 37); and a light chain complementarity determining region 3 (CDR3) comprising the amino acid sequence of "Glu Thr Trp Asp Thr Ser Leu Ser Ala Gly Arg Val" (SEQ ID NO: 38).

6. The antibody of claim 2, wherein the antibody is a monoclonal antibody.

7. The antibody of claim 6, wherein the antibody is a fully human monoclonal antibody.

8. The antibody of claim 5, wherein the antibody is a monoclonal antibody.

9. The antibody of claim 8, wherein the antibody is a fully human monoclonal antibody.

10. A composition comprising the antibody, or antibody binding fragment, of any one of claims 1, 2, or 5-9.

11. The composition of claim 10, further comprising a pharmaceutically acceptable carrier.

12. An isolated antibody, or binding fragment thereof, that preferentially binds to insulin-like growth factor-II (IGF-II) with cross-reactivity to insulin-like growth factor I (IGF-I), wherein said antibody comprises a light chain polypeptide comprising the sequence of SEQ ID NO.: 8 and a heavy chain polypeptide.

13. The antibody of claim 12, wherein the heavy chain polypeptide comprises the sequence of SEQ ID NO.: 6.

14. The antibody of any one of claims 1, 2 or 5 in a mixture with a pharmaceutically acceptable carrier.

15. A conjugate comprising the antibody of any one of claims 1, 2 or 5 and a therapeutic agent.

16. The conjugate of claim 15, wherein the therapeutic agent is a toxin.

17. The conjugate of claim 15, wherein the therapeutic agent is a radioisotope.

18. The antibody of any one of claims 12 or 13 in a mixture with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,939,637 B2 | Page 1 of 1 |
| APPLICATION NO. | : 11/608705 | |
| DATED | : May 10, 2011 | |
| INVENTOR(S) | : Raeber et al. | |

It is certified that error appears in the above-identified patent and that said Letters Patent is hereby corrected as shown below:

In the Specification, column 1, line 11, "Feb. 17, 2005" should read -- Feb. 17, 2006--.

Signed and Sealed this
Twenty-third Day of August, 2011

David J. Kappos
*Director of the United States Patent and Trademark Office*